(12) United States Patent
Martin et al.

(10) Patent No.: US 9,746,354 B2
(45) Date of Patent: Aug. 29, 2017

(54) ELASTOMER ENCASED MOTION SENSOR PACKAGE

(71) Applicant: BLAST MOTION INC., Burlingame, CA (US)

(72) Inventors: Joshua Martin, San Diego, CA (US); Bhaskar Bose, San Diego, CA (US); Michael Bentley, San Diego, CA (US); Ryan Kaps, Mesa, AZ (US)

(73) Assignee: BLAST MOTION INC., Carlsbad, CA (US)

( * ) Notice: Subject to any disclaimer, the term of this patent is extended or adjusted under 35 U.S.C. 154(b) by 0 days.

(21) Appl. No.: 15/011,100

(22) Filed: Jan. 29, 2016

(65) Prior Publication Data

US 2016/0146643 A1     May 26, 2016

Related U.S. Application Data

(63) Continuation-in-part of application No. 13/688,213, filed on Nov. 29, 2012, which is a
(Continued)

(51) Int. Cl.
*A63B 69/36*     (2006.01)
*A63B 53/00*     (2015.01)
(Continued)

(52) U.S. Cl.
CPC ............ *G01D 11/245* (2013.01); *A63B 60/16* (2015.10); *A63C 11/00* (2013.01); *G01C 19/00* (2013.01);
(Continued)

(58) Field of Classification Search
CPC ......... A63B 60/46; A63B 49/00; A63B 49/08; A63B 53/00; A63B 53/14; A63B 59/20;
(Continued)

(56) References Cited

U.S. PATENT DOCUMENTS

| 1,712,537 A | 5/1925 | White |
| 2,038,840 A | 4/1936 | Hall |

(Continued)

FOREIGN PATENT DOCUMENTS

| CA | 2694123 | 8/2011 |
| KR | 20070120443 | 12/2007 |

(Continued)

OTHER PUBLICATIONS

Armour39 Module & Chest Strap, retrieved from the Internet on Jul. 12, 2013, 6 pages.
(Continued)

*Primary Examiner* — Lawrence Galka
(74) *Attorney, Agent, or Firm* — Arc IP Law, PC; Joseph J. Mayo

(57) ABSTRACT

A motion sensor package with an elastomer layer that encases the sensor electronics, including the sensors, a processor, an antenna, and a battery. The elastomer layer may provide shock isolation and water resistance to protect the enclosed electronics. Embodiments may also include an outer housing into which the elastomer encased package is installed. The outer housing may for example comprise two cylindrical sections that screw together to close the outer housing. In one or more embodiments part of the outer housing may be integrated into an item of sports equipment. Embodiments for golf may also include a golf club grip adapter that is inserted into the top of a grip, and which attaches to the outer housing containing the elastomer enclosed sensor package.

11 Claims, 47 Drawing Sheets

Related U.S. Application Data continuation-in-part of application No. 13/306,869, filed on Nov. 29, 2011, now Pat. No. 9,028,337, which is a continuation-in-part of application No. 13/191,309, filed on Jul. 26, 2011, now Pat. No. 9,033,810, which is a continuation-in-part of application No. 13/048,850, filed on Mar. 15, 2011, now Pat. No. 8,465,376, which is a continuation-in-part of application No. 12/901,806, filed on Oct. 11, 2010, which is a continuation-in-part of application No. 12/868,882, filed on Aug. 26, 2010, now Pat. No. 8,994,826.

(51) Int. Cl.

| | | |
|---|---|---|
| *G01D 11/24* | (2006.01) | |
| *A63C 11/00* | (2006.01) | |
| *G01S 19/19* | (2010.01) | |
| *G01S 19/35* | (2010.01) | |
| *G01C 19/00* | (2013.01) | |
| *G06F 3/01* | (2006.01) | |
| *G06F 3/0346* | (2013.01) | |
| *A63B 60/16* | (2015.01) | |
| *H01Q 9/42* | (2006.01) | |
| *H01Q 13/10* | (2006.01) | |
| *H01Q 21/28* | (2006.01) | |
| *A63B 69/00* | (2006.01) | |
| *A63B 21/072* | (2006.01) | |
| *A63B 49/00* | (2015.01) | |
| *A63B 53/14* | (2015.01) | |
| *G01S 19/36* | (2010.01) | |
| *A63B 21/00* | (2006.01) | |
| *A63B 60/42* | (2015.01) | |
| *A61B 5/11* | (2006.01) | |
| *A63B 71/00* | (2006.01) | |
| *A63B 59/50* | (2015.01) | |

(52) U.S. Cl.
CPC .............. *G01S 19/19* (2013.01); *G01S 19/35* (2013.01); *G06F 3/011* (2013.01); *G06F 3/0346* (2013.01); *H01Q 9/42* (2013.01); *H01Q 13/10* (2013.01); *H01Q 21/28* (2013.01); *A61B 5/1128* (2013.01); *A63B 21/0724* (2013.01); *A63B 21/0726* (2013.01); *A63B 21/4035* (2015.10); *A63B 49/00* (2013.01); *A63B 53/00* (2013.01); *A63B 53/14* (2013.01); *A63B 59/50* (2015.10); *A63B 60/42* (2015.10); *A63B 69/0093* (2013.01); *A63B 69/3632* (2013.01); *A63B 2069/0008* (2013.01); *A63B 2071/0063* (2013.01); *A63B 2209/02* (2013.01); *A63B 2220/12* (2013.01); *A63B 2220/16* (2013.01); *A63B 2220/17* (2013.01); *A63B 2220/30* (2013.01); *A63B 2220/34* (2013.01); *A63B 2220/40* (2013.01); *A63B 2220/44* (2013.01); *A63B 2220/806* (2013.01); *A63B 2220/833* (2013.01); *A63B 2225/15* (2013.01); *A63B 2225/20* (2013.01); *A63B 2225/50* (2013.01); *A63B 2225/54* (2013.01); *A63C 2203/18* (2013.01); *A63C 2203/22* (2013.01); *A63C 2203/24* (2013.01); *G01S 19/36* (2013.01)

(58) Field of Classification Search
CPC ......... A63B 59/40; A63B 59/50; A63B 59/60; A63B 59/70; A63B 59/80; A63B 69/36; A63B 69/3614; A63B 69/3632
See application file for complete search history.

(56) References Cited

U.S. PATENT DOCUMENTS

| | | | |
|---|---|---|---|
| 2,218,268 A | 10/1940 | Reid | |
| 3,182,508 A | 5/1965 | Varju | |
| 3,223,555 A | 12/1965 | Himy et al. | |
| 3,226,704 A | 12/1965 | Petrash | |
| 3,270,564 A | 9/1966 | Evans | |
| 3,606,327 A | 9/1971 | Gorman | |
| 3,788,647 A | 1/1974 | Evans | |
| 3,792,863 A | 2/1974 | Evans | |
| 3,806,131 A | 4/1974 | Evans | |
| 3,945,646 A | 3/1976 | Hammond | |
| 4,088,324 A | 5/1978 | Farmer | |
| 4,261,113 A | 4/1981 | Alderson et al. | |
| D295,207 S | 4/1988 | Mahaffey | |
| 4,759,219 A | 7/1988 | Cobb et al. | |
| 4,898,389 A | 2/1990 | Plutt | |
| 4,910,677 A | 3/1990 | Remedio et al. | |
| 4,912,836 A | 4/1990 | Avetoom | |
| 4,940,236 A | 7/1990 | Allen | |
| 4,991,850 A | 2/1991 | Wilhlem | |
| 5,056,783 A | 10/1991 | Matcovich et al. | |
| 5,086,390 A | 2/1992 | Matthews | |
| 5,111,410 A | 5/1992 | Nakayama et al. | |
| 5,127,044 A | 6/1992 | Bonito et al. | |
| 5,184,295 A | 2/1993 | Mann | |
| 5,230,512 A | 7/1993 | Tattershall | |
| 5,233,544 A | 8/1993 | Kobayashi | |
| 5,249,967 A | 10/1993 | O'Leary et al. | |
| 5,259,620 A | 11/1993 | Marocco | |
| 5,283,733 A | 2/1994 | Colley | |
| 5,298,904 A | 3/1994 | Olich | |
| 5,332,225 A | 7/1994 | Ura | |
| 5,333,061 A | 7/1994 | Nakashima et al. | |
| 5,364,093 A | 11/1994 | Huston et al. | |
| 5,372,365 A | 12/1994 | McTeigue | |
| 5,422,798 A | 6/1995 | Osiecki et al. | |
| 5,441,256 A | 8/1995 | Hackman | |
| 5,441,269 A | 8/1995 | Henwood | |
| 5,460,372 A | 10/1995 | Cook | |
| 5,486,001 A | 1/1996 | Baker | |
| 5,524,081 A | 6/1996 | Paul | |
| 5,542,676 A | 8/1996 | Howe et al. | |
| 5,592,401 A | 1/1997 | Kramer | |
| 5,626,527 A | 5/1997 | Eberlein | |
| 5,632,484 A | 5/1997 | Lambert | |
| 5,638,300 A | 6/1997 | Johnson | |
| 5,665,006 A | 9/1997 | Pellegrini | |
| 5,688,183 A | 11/1997 | Sabatino et al. | |
| 5,694,340 A | 12/1997 | Kim | |
| 5,772,522 A | 6/1998 | Nesbit | |
| 5,779,555 A | 7/1998 | Nomura et al. | |
| 5,792,001 A | 8/1998 | Henwood | |
| 5,800,279 A * | 9/1998 | Densberger et al. | 473/220 |
| D399,282 S | 10/1998 | Jarrett | |
| 5,819,206 A | 10/1998 | Horton | |
| 5,826,578 A | 10/1998 | Curchod | |
| 5,868,578 A | 2/1999 | Baum | |
| 5,904,484 A | 5/1999 | Burns | |
| 5,941,779 A | 8/1999 | Zeiner-Gundersen | |
| 5,973,596 A | 10/1999 | French et al. | |
| 6,007,439 A | 12/1999 | MacKay, Jr. | |
| 6,030,109 A | 2/2000 | Lobsenz | |
| 6,044,704 A | 4/2000 | Sacher | |
| 6,073,086 A | 6/2000 | Marinelli | |
| 6,224,493 B1 | 5/2001 | Lee et al. | |
| 6,244,356 B1 | 6/2001 | Luna | |
| 6,248,021 B1 | 6/2001 | Ognjanovic | |
| 6,293,802 B1 | 9/2001 | Ahlgren | |
| 6,366,205 B1 | 4/2002 | Sutphen | |
| 6,409,616 B1 * | 6/2002 | Lin | A63B 69/38 473/463 |
| 6,441,745 B1 | 8/2002 | Gates | |
| 6,443,860 B1 | 9/2002 | Byrne et al. | |
| 6,456,938 B1 | 9/2002 | Barnard | |
| 6,565,449 B2 * | 5/2003 | Buhler | A63B 24/0021 473/151 |

(56) References Cited

U.S. PATENT DOCUMENTS

| | | |
|---|---|---|
| 6,567,536 B2 | 5/2003 | McNitt |
| 6,582,328 B2 | 6/2003 | Kuta et al. |
| 6,697,761 B2 | 2/2004 | Akatsuka |
| 6,697,820 B1 | 2/2004 | Tarlie |
| 6,705,942 B1 | 3/2004 | Crook et al. |
| 6,709,352 B1 | 3/2004 | Albin |
| 6,746,336 B1 | 6/2004 | Brant et al. |
| 6,757,572 B1 | 6/2004 | Forest |
| 6,774,932 B1 | 8/2004 | Ewing et al. |
| 6,802,772 B1 | 10/2004 | Kunzle et al. |
| 6,826,509 B2 | 11/2004 | Crisco et al. |
| 6,900,759 B1 | 5/2005 | Katayama |
| 6,908,404 B1 | 6/2005 | Gard |
| 6,923,729 B2 | 8/2005 | McGinty et al. |
| 7,004,848 B2 | 2/2006 | Konow |
| 7,021,140 B2 | 4/2006 | Perkins |
| D522,078 S | 5/2006 | Gruccio |
| 7,037,198 B2 | 5/2006 | Hameen-Anttila |
| D523,507 S | 6/2006 | Perry |
| 7,118,498 B2 | 10/2006 | Meadows et al. |
| 7,121,962 B2 | 10/2006 | Reeves |
| 7,143,639 B2 | 12/2006 | Gobush |
| 7,160,200 B2 | 1/2007 | Grober |
| 7,175,177 B2 | 2/2007 | Meifu et al. |
| 7,184,151 B2 | 2/2007 | Clarke |
| 7,204,165 B1 | 4/2007 | Plaga et al. |
| 7,205,894 B1 | 4/2007 | Savage |
| 7,219,033 B2 | 5/2007 | Kolen |
| 7,234,351 B2 | 6/2007 | Perkins |
| 7,264,098 B2 | 9/2007 | McPherson |
| 7,264,554 B2 | 9/2007 | Bentley |
| 7,267,619 B1 | 9/2007 | Pettis |
| 7,433,805 B2 | 10/2008 | Vock et al. |
| 7,457,439 B1 | 11/2008 | Madsen |
| 7,457,724 B2 | 11/2008 | Vock et al. |
| 7,481,716 B1 | 1/2009 | Johnson |
| 7,492,367 B2 | 2/2009 | Mahajan et al. |
| 7,494,236 B2 | 2/2009 | Lim |
| 7,561,989 B2 | 7/2009 | Banks |
| 7,623,987 B2 | 11/2009 | Vock et al. |
| 7,689,378 B2 | 3/2010 | Kolen |
| 7,713,148 B2 | 5/2010 | Sweeney |
| 7,736,242 B2 | 6/2010 | Stites et al. |
| 7,771,263 B2 | 8/2010 | Telford |
| 7,780,450 B2 | 8/2010 | Tarry |
| 7,800,480 B1 | 9/2010 | Joseph et al. |
| 7,813,887 B2 | 10/2010 | Vock et al. |
| 7,831,212 B1 | 11/2010 | Balardeta et al. |
| 7,871,333 B1 | 1/2011 | Davenport |
| 7,966,154 B2 | 6/2011 | Vock et al. |
| 7,983,876 B2 | 7/2011 | Vock et al. |
| 8,036,826 B2 | 10/2011 | MacIntosh et al. |
| 8,117,888 B2 | 2/2012 | Chan et al. |
| 8,172,722 B2 | 5/2012 | Molyneux et al. |
| 8,231,506 B2 | 7/2012 | Molyneux et al. |
| 8,249,831 B2 | 8/2012 | Vock et al. |
| 8,257,191 B2 | 9/2012 | Stites et al. |
| 8,348,783 B2 | 1/2013 | Soracco et al. |
| 8,355,529 B2 | 1/2013 | Wu et al. |
| 8,425,292 B2 | 4/2013 | Lui et al. |
| 8,840,483 B1 | 9/2014 | Steusloff et al. |
| 2001/0029207 A1 | 10/2001 | Cameron et al. |
| 2001/0035880 A1 | 11/2001 | Musatov et al. |
| 2001/0045904 A1 | 11/2001 | Silzer, Jr. |
| 2002/0004723 A1 | 1/2002 | Meifu et al. |
| 2002/0019677 A1 | 2/2002 | Lee |
| 2002/0049507 A1 | 4/2002 | Hameen-Anttila |
| 2002/0052750 A1 | 5/2002 | Hirooka |
| 2002/0064764 A1 | 5/2002 | Fishman |
| 2002/0072815 A1 | 6/2002 | McDonough et al. |
| 2002/0077189 A1 | 6/2002 | Tuer et al. |
| 2002/0082775 A1 | 6/2002 | Meadows et al. |
| 2002/0150873 A1* | 10/2002 | Smith .................... 434/252 |
| 2002/0151994 A1 | 10/2002 | Sisco |
| 2002/0173364 A1 | 11/2002 | Boscha |
| 2002/0177490 A1 | 11/2002 | Yong et al. |
| 2002/0186132 A1 | 12/2002 | Kruger |
| 2002/0188359 A1 | 12/2002 | Morse |
| 2003/0008722 A1 | 1/2003 | Konow |
| 2003/0063292 A1 | 4/2003 | Mostafavi |
| 2004/0147329 A1 | 7/2004 | Meadows et al. |
| 2004/0224787 A1 | 11/2004 | Lindner |
| 2004/0248676 A1 | 12/2004 | Taylor et al. |
| 2005/0032582 A1 | 2/2005 | Mahajan et al. |
| 2005/0054457 A1 | 3/2005 | Eyestone et al. |
| 2005/0177929 A1 | 8/2005 | Greenwald et al. |
| 2005/0215340 A1 | 9/2005 | Stites et al. |
| 2005/0227775 A1 | 10/2005 | Cassady et al. |
| 2005/0261073 A1 | 11/2005 | Farrington, Jr. et al. |
| 2005/0268704 A1 | 12/2005 | Bissonnette et al. |
| 2005/0272516 A1 | 12/2005 | Gobush |
| 2005/0282650 A1 | 12/2005 | Miettinen et al. |
| 2006/0025229 A1 | 2/2006 | Mahajan et al. |
| 2006/0063600 A1 | 3/2006 | Grober |
| 2006/0084516 A1 | 4/2006 | Eyestone et al. |
| 2006/0109116 A1 | 5/2006 | Keays |
| 2006/0122002 A1 | 6/2006 | Konow |
| 2006/0166738 A1 | 7/2006 | Eyestone et al. |
| 2006/0199659 A1 | 9/2006 | Caldwell |
| 2006/0270450 A1 | 11/2006 | Garratt et al. |
| 2006/0276256 A1 | 12/2006 | Storek |
| 2007/0081695 A1 | 4/2007 | Foxlin et al. |
| 2007/0087866 A1 | 4/2007 | Meadows et al. |
| 2007/0099715 A1 | 5/2007 | Jones et al. |
| 2007/0111811 A1 | 5/2007 | Grober |
| 2007/0129178 A1 | 6/2007 | Reeves |
| 2007/0135225 A1 | 6/2007 | Nieminen |
| 2007/0135237 A1 | 6/2007 | Reeves |
| 2007/0270214 A1 | 11/2007 | Bentley |
| 2007/0298896 A1 | 12/2007 | Nusbaum |
| 2008/0305895 A1* | 12/2008 | Gant .................... 473/453 |
| 2009/0017944 A1 | 1/2009 | Savarese et al. |
| 2009/0036237 A1 | 2/2009 | Nipper et al. |
| 2009/0111602 A1 | 4/2009 | Savarese et al. |
| 2009/0137333 A1 | 5/2009 | Lin et al. |
| 2009/0177097 A1 | 7/2009 | Ma et al. |
| 2009/0209343 A1 | 8/2009 | Foxlin |
| 2009/0209358 A1 | 8/2009 | Niegowski |
| 2009/0233735 A1 | 9/2009 | Savarese et al. |
| 2010/0049468 A1 | 2/2010 | Papadourakis |
| 2010/0063778 A1 | 3/2010 | Schrock et al. |
| 2010/0063779 A1 | 3/2010 | Schrock et al. |
| 2010/0079830 A1 | 4/2010 | Lacoste |
| 2010/0091112 A1 | 4/2010 | Veeser et al. |
| 2010/0093458 A1 | 4/2010 | Davenport et al. |
| 2010/0113174 A1 | 5/2010 | Ahern |
| 2010/0130298 A1 | 5/2010 | Dugan et al. |
| 2010/0144414 A1 | 6/2010 | Edis et al. |
| 2010/0144456 A1* | 6/2010 | Ahern .................... 473/222 |
| 2010/0216564 A1 | 8/2010 | Stites et al. |
| 2010/0222152 A1 | 9/2010 | Jaekel et al. |
| 2010/0308105 A1 | 12/2010 | Savarese et al. |
| 2011/0015005 A1 | 1/2011 | Pfeifer |
| 2011/0037778 A1 | 2/2011 | Deng et al. |
| 2011/0053688 A1 | 3/2011 | Crawford |
| 2011/0075341 A1 | 3/2011 | Lau et al. |
| 2011/0165998 A1 | 7/2011 | Lau et al. |
| 2011/0230273 A1 | 9/2011 | Niegowski et al. |
| 2011/0230274 A1 | 9/2011 | Lafortune et al. |
| 2011/0230985 A1 | 9/2011 | Niegowski et al. |
| 2011/0230986 A1 | 9/2011 | Lafortune |
| 2012/0052972 A1 | 3/2012 | Bentley |
| 2012/0075095 A1 | 3/2012 | Howard et al. |
| 2012/0115682 A1 | 5/2012 | Homsi |
| 2012/0119098 A1 | 5/2012 | Konkle et al. |
| 2012/0120573 A1 | 5/2012 | Bentley |
| 2012/0124720 A1 | 5/2012 | Evans et al. |
| 2012/0157243 A1 | 6/2012 | Gallo |
| 2012/0210498 A1 | 8/2012 | Mack |
| 2012/0277015 A1* | 11/2012 | Boyd et al. .................... 473/223 |
| 2013/0060168 A1 | 3/2013 | Chu et al. |
| 2013/0065703 A1 | 3/2013 | Rose |
| 2013/0073248 A1* | 3/2013 | Perkins et al. .................... 702/141 |
| 2013/0167290 A1 | 7/2013 | Ben Ezra |

(56) References Cited

U.S. PATENT DOCUMENTS

| | | | |
|---|---|---|---|
| 2013/0203517 A1* | 8/2013 | Bolane et al. | 473/223 |
| 2013/0274904 A1* | 10/2013 | Coza et al. | 700/91 |
| 2016/0074714 A1* | 3/2016 | Krysiak | A63B 41/08 473/570 |

FOREIGN PATENT DOCUMENTS

| | | |
|---|---|---|
| KR | 10-1079319 | 6/2011 |
| WO | 94/27683 | 8/1994 |

OTHER PUBLICATIONS

Armour39, Under Armour Guarantee, Getting Started, retrieved from the Internet on Jul. 12, 2013, 7 pages.
Foreman et al. "A Comparative Analysis for the Measurement of Head Accelerations in Ice Hockey Helmets using Non-Accelerometer Based Systems," Nov. 19, 2012, 13 pages.
Gehrig et al, Visual Golf Club Tracking for Enhanced Swing Analysis, Computer Vision Lab, Lausanne, Switzerland, 2003.
Grober, An Accelerometer Based Instrumentation of the Golf Club: Comparative Analysis of Golf Swings, 2009.
International Search Report dated Jul. 18, 2013, 6 pages, PCT Appl. No. PCT/US2013/038694.
International Search Report dated Mar. 29, 2013, 10 pages.
King, The Design and Application of Wireless Mems Inertial Measurement Units for the Measurement and Analysis of Golf Swings, 2008.
Learn how Swingbyte can improve your game, retrieved on Sep. 26, 2012 from http://www.swingbyte.com, 2 pages.
miCoach Pacer User Manual, 31 pages, 2009.
miCoach Speed_Cell TM, User Manual, 23 pages, 2011.
myCaddie, 2009, retrieved on Sep. 26, 2012 from http://www.iMakePars.com, 4 pages.
Nike+iPod, User Guide, 32 pages.
Pocketpro Golf Designs, PocketPro Full Swing Analysis in Your Pocket, www.PocketPro.org , 2011.
SureShotGPS SS9000X, Intelligent Touch, Instruction Manual, 25 pages, 2011.
Swing it See it Fix it, Improve Gold Swing, SwingSmart Golf Analyzer, retrieved on Sep. 26, 2012 from http://www.SwingSmart.com, 2 pages.
The Nike+FuelBand User's Guide, rev 14, 26 pages, 2012.
UP by Jawbone Extended User Guide, 10 pages, 2013.
ActiveReply, "TRACE—The Most Advanced Activity Monitor for Action Sports", http://www.kickstarter.com/projects/activereplay/trace-the-most-advanced-activity-monitor-for-actio, 13 pages, Jul. 31, 2013.
International Search Report and Written Opinion dated Mar. 27, 2014, 7 pages, PCT Appl. No. PCT/US2013/072461.
International Search Report on Patentability dated Jun. 12, 2014.
Partial European Search Report received in PCT2012066915 dated Jul. 31, 2015, 7 pages.
Extended European Search Report received in PCT2012066915 dated Nov. 16, 2015, 13 pages.

* cited by examiner

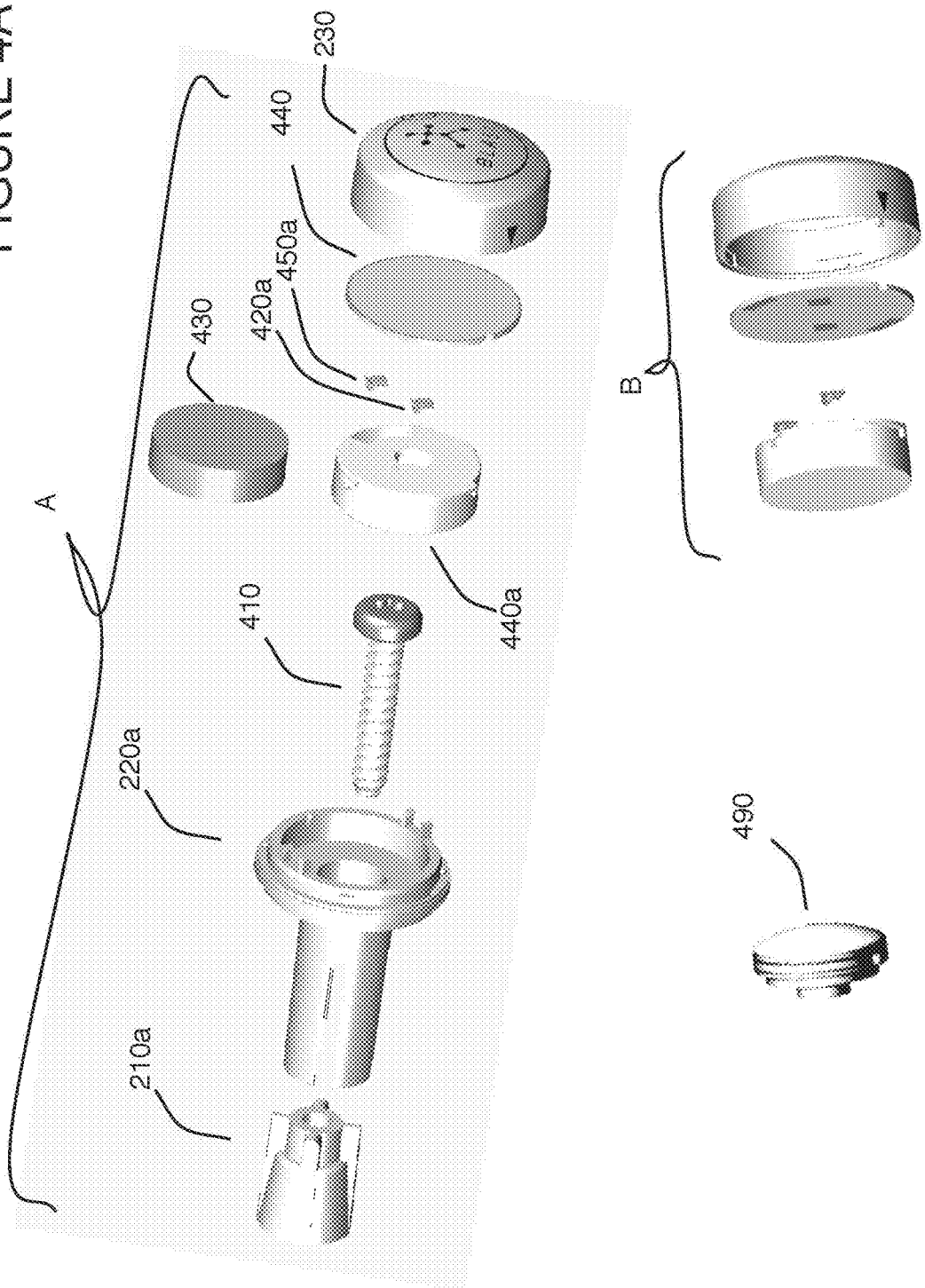

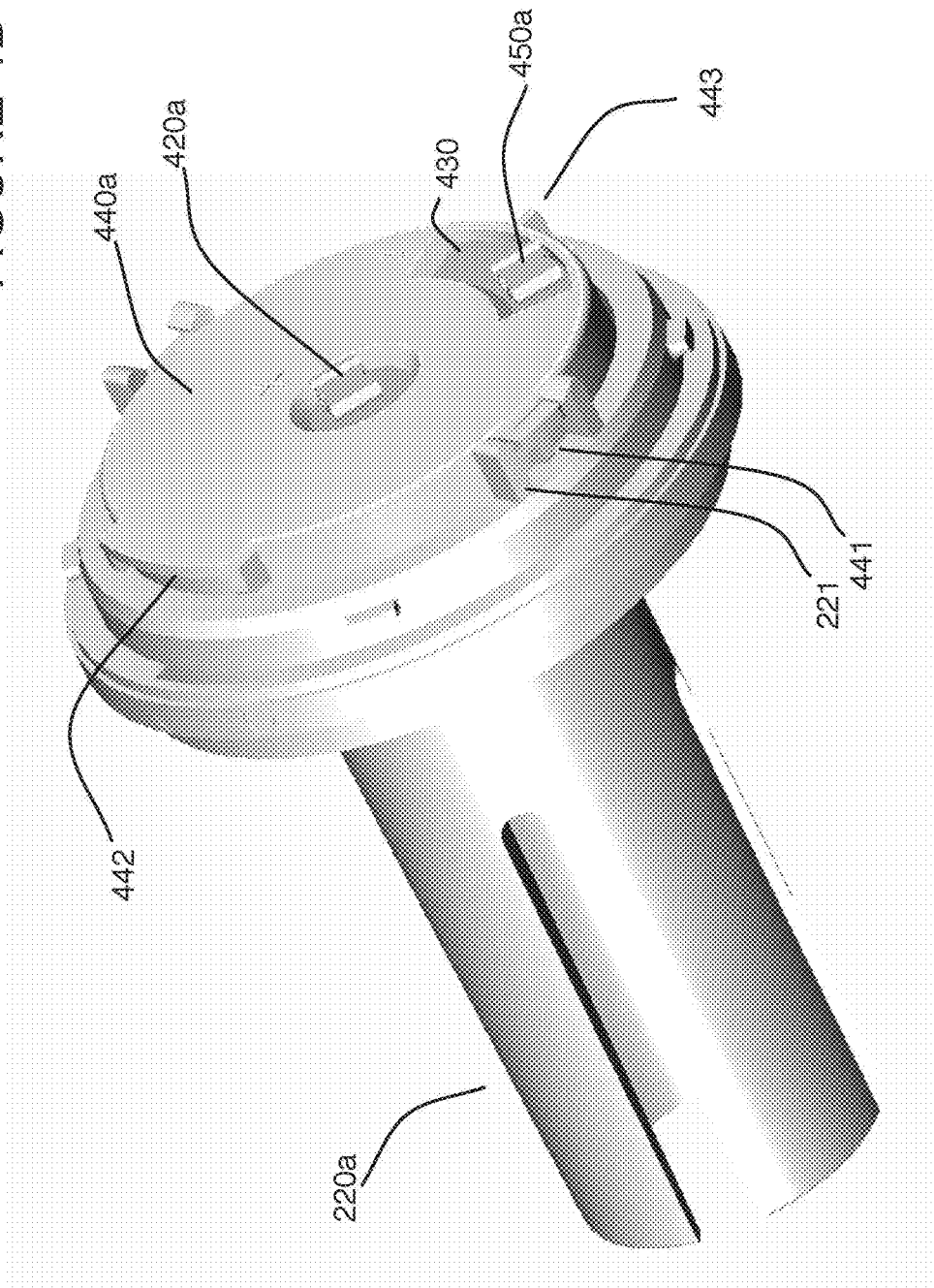

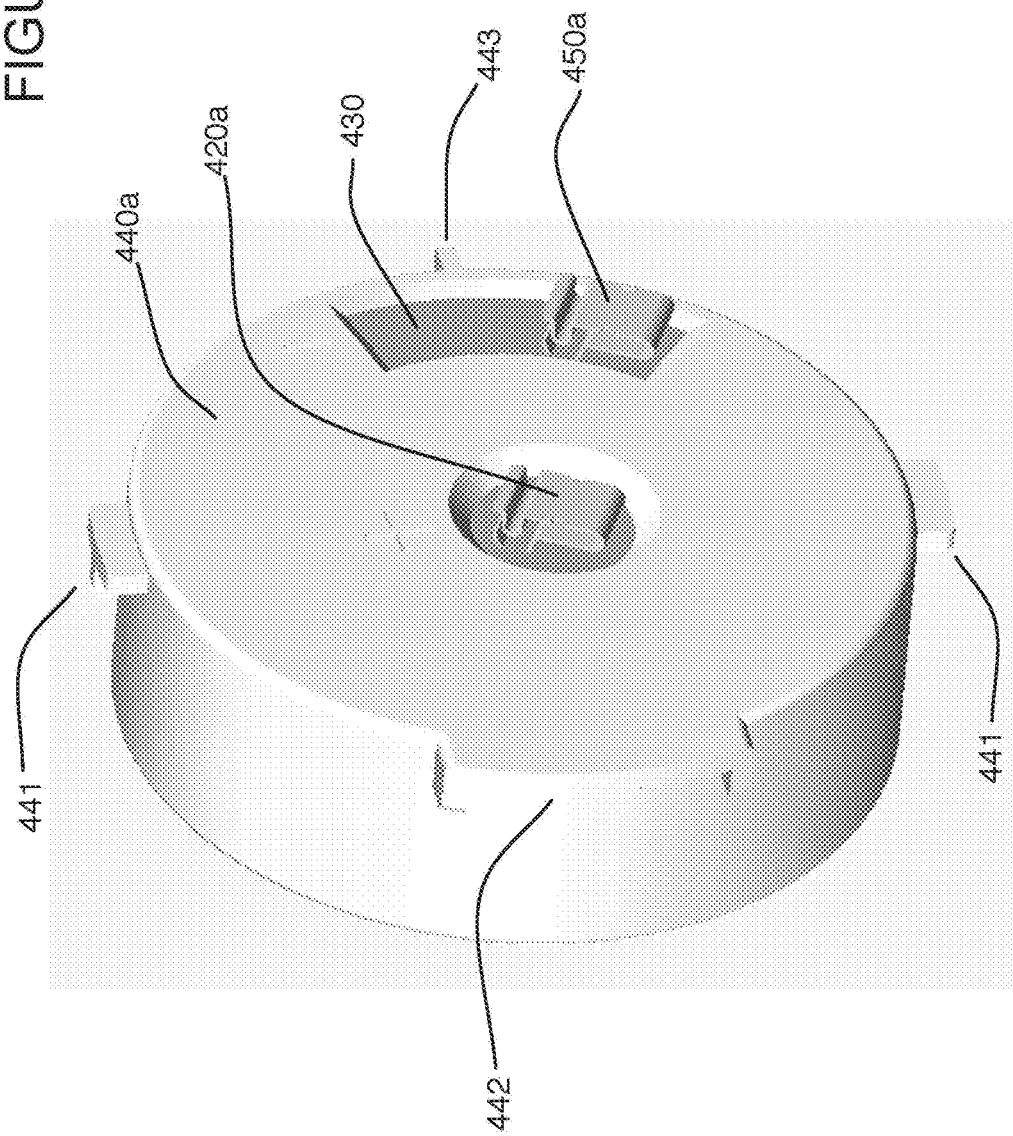

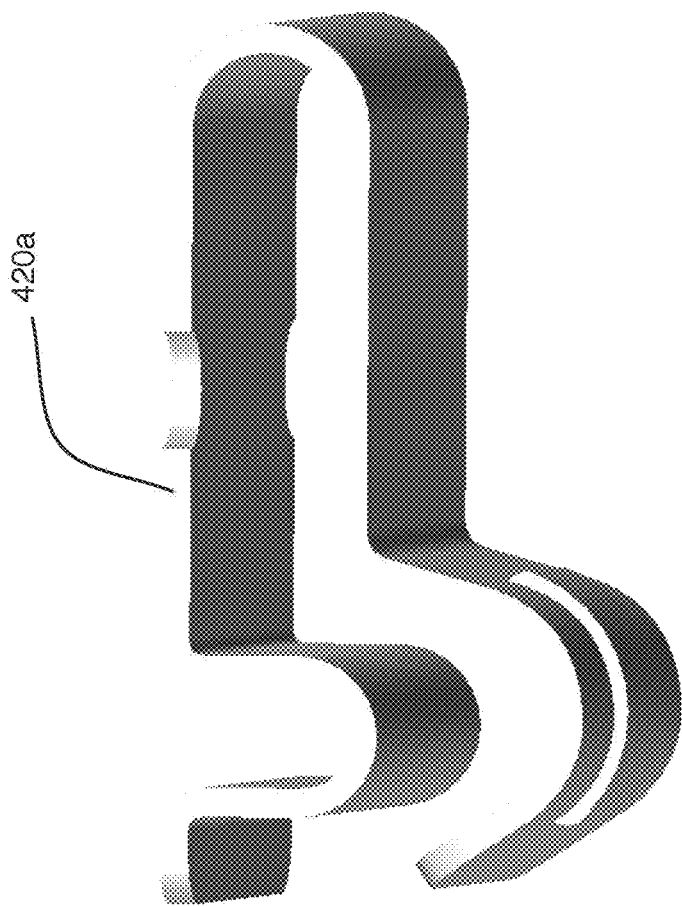

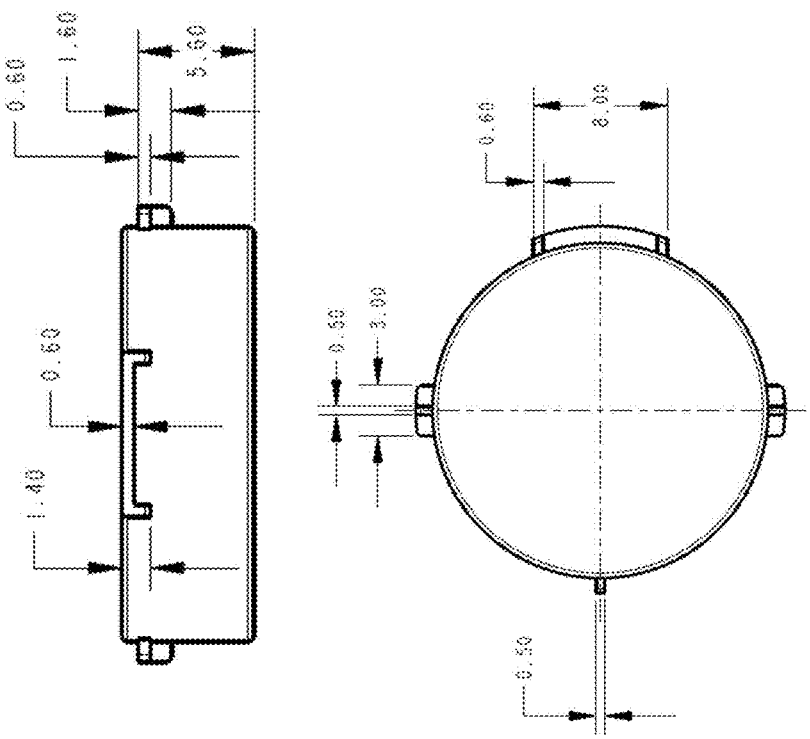
FIGURE 4G
FIGURE 4I
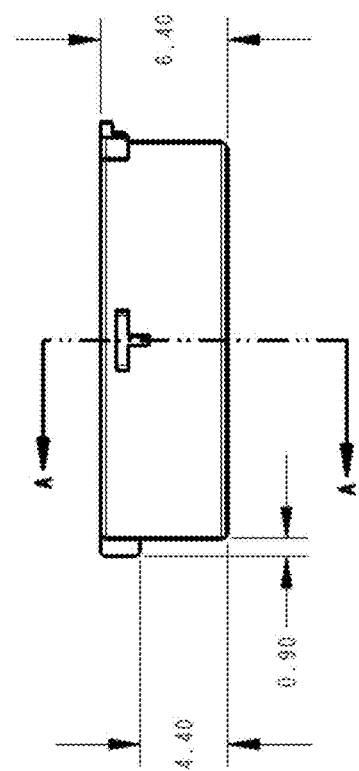
FIGURE 4F
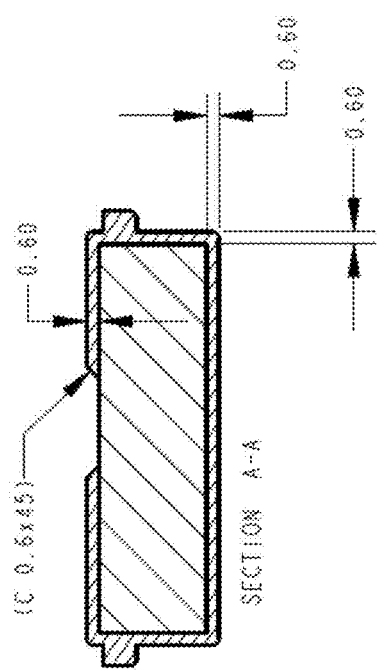
FIGURE 4H

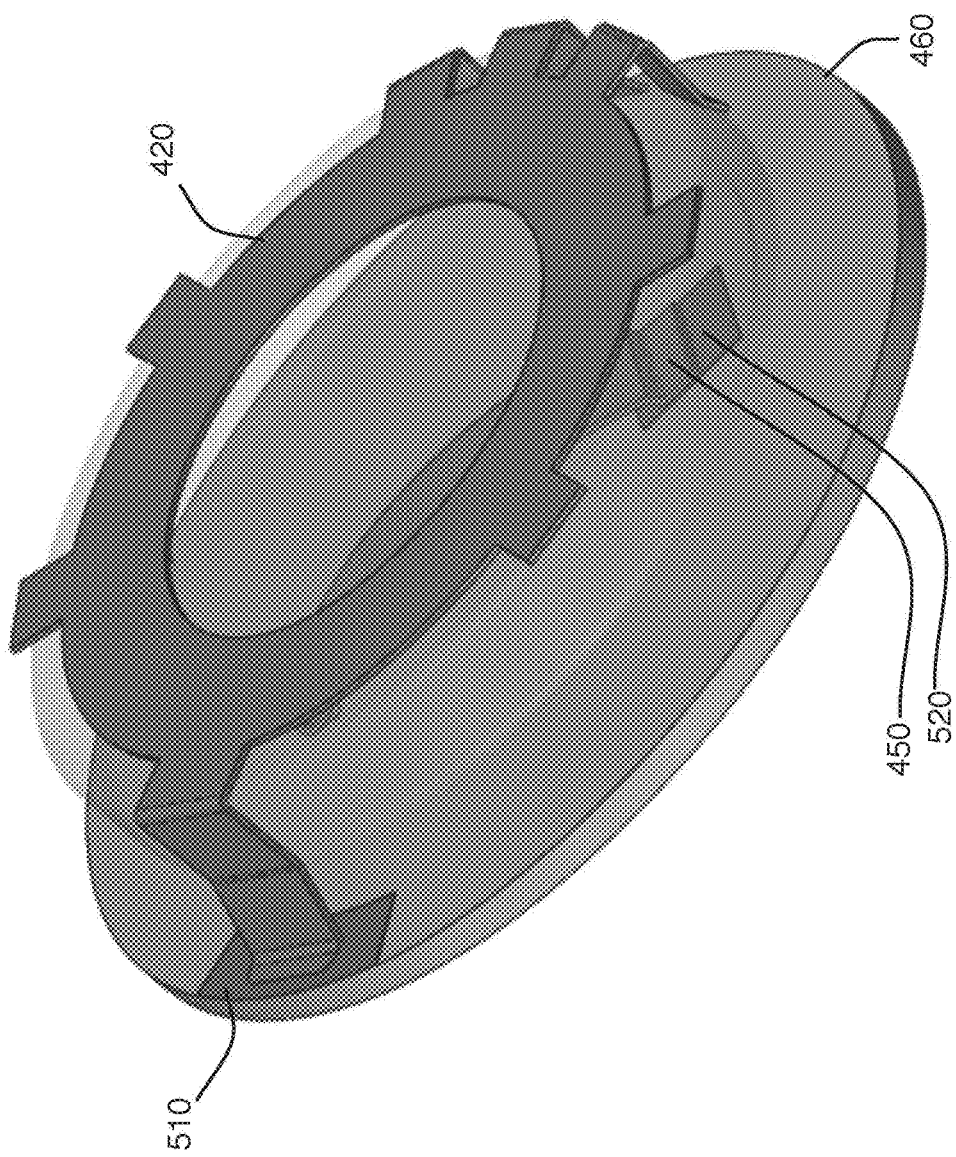

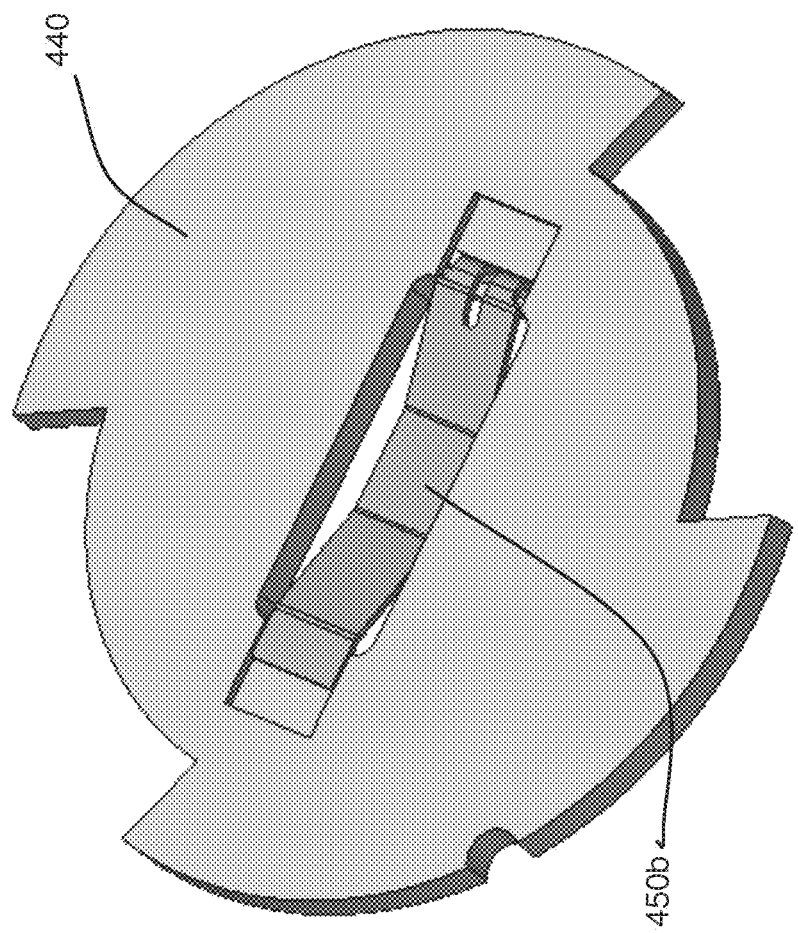

FIG. 34
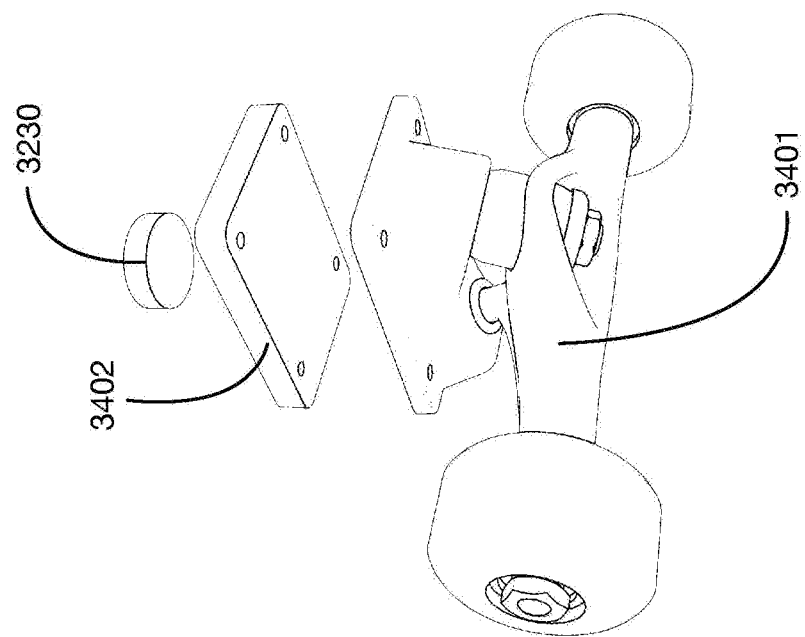
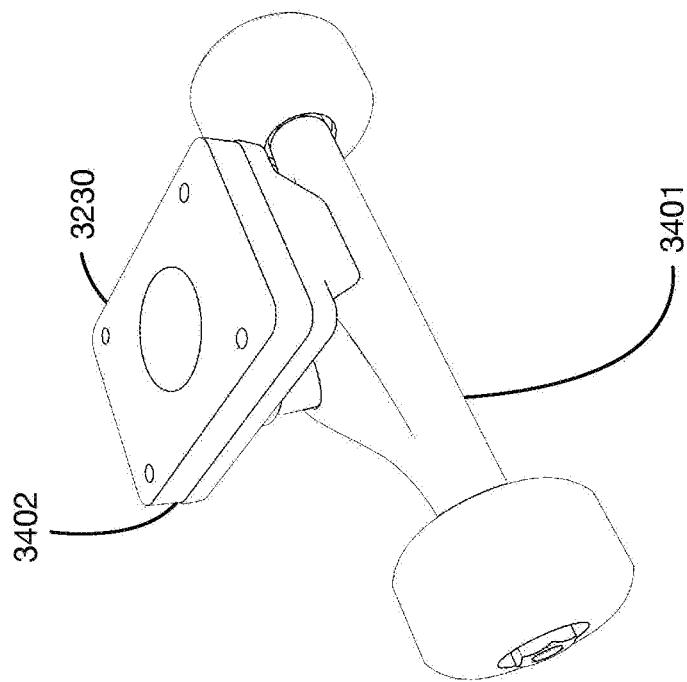

FIG. 38
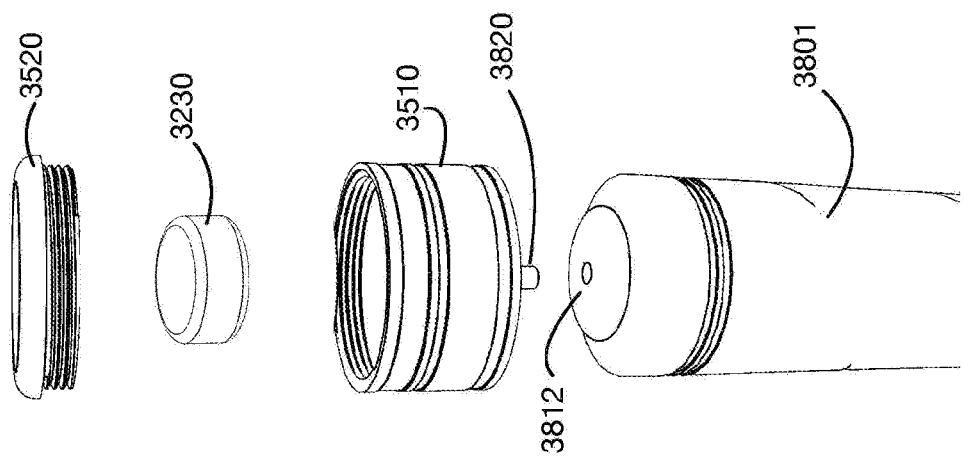
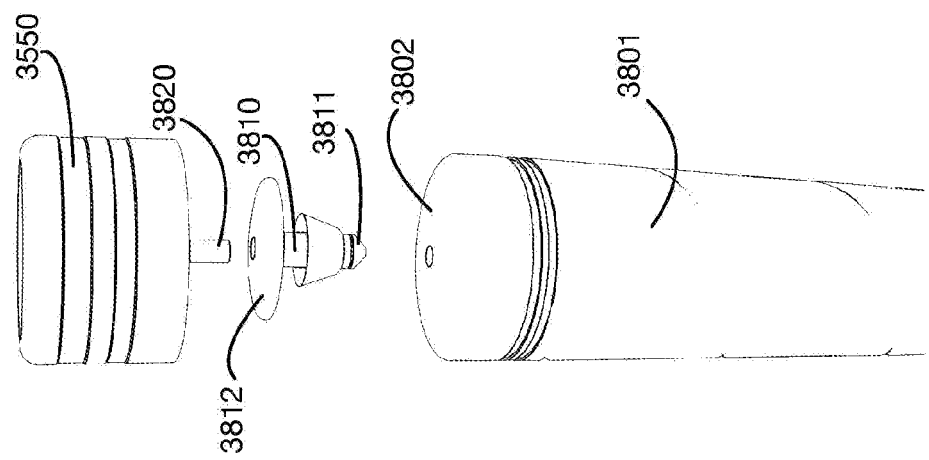

ELASTOMER ENCASED MOTION SENSOR PACKAGE

This application is a continuation-in-part of U.S. Utility patent application Ser. No. 13/688,213 filed 29 Nov. 2012, which is a continuation-in-part of U.S. Utility patent application Ser. No. 13/306,869 filed 29 Nov. 2011, which is a continuation-in-part of U.S. Utility patent application Ser. No. 13/191,309 filed 26 Jul. 2011, which is a continuation-in-part of U.S. Utility patent application Ser. No. 13/048,850 filed 15 Mar. 2011, which is a continuation-in-part of U.S. Utility patent application Ser. No. 12/901,806 filed 11 Oct. 2010, which is a continuation-in-part of U.S. Utility patent application Ser. No. 12/868,882 filed 26 Aug. 2010, the specifications of which are hereby incorporated herein by reference.

BACKGROUND OF THE INVENTION

Field of the Invention

One or more embodiments setting forth the ideas described throughout this disclosure pertain to the field of mounts as utilized in sporting equipment for electronics and visual markers. More particularly, but not by way of limitation, one or more aspects of the disclosure enable an elastomer encased motion sensor package.

Description of the Related Art

Known systems for mounting electronics on sporting equipment include mounts in the shafts of fishing poles, and golf clubs for example. Existing mounts have the following limitations:

- Existing mounts for sporting equipment electronics require alteration of an existing piece of sporting equipment before attaching the mount and hence electronics. For example, known mounts require modification of the shaft of the piece of equipment to include threads.
- Some mounts extend longitudinally away from the normal ending point of the shaft for a distance that is far enough to interfere with or provide a confusing point at which to grasp the club.
- Other mounts combine the electronics on the mount itself in a monolithic package that does not allow for the weight of the club to remain constant with or without electronics installed. For example, in sports with rules against instrumented sporting equipment, the weight of an instrumented piece of sporting equipment differs from the weight of the same non-instrumented piece of sporting equipment that complies with competition rules.
- There are no known systems that include electronics within the shaft of a piece of sporting equipment that are also utilized to provide a visual marker for motion capture. Traditionally, mounts have been used for electronics or visual markers, but not both.
- Existing enclosures and mounts may break or shatter if they experience an impact shock. Upon impact, fragments of the mount, or of the enclosed electronics, may fly away from the enclosure and/or mount towards a user or spectator, posing a safety hazard.
- Existing enclosures and mounts do not provide shock absorption or shock isolation. The enclosed electronics may therefore experience very large shock forces, destroying them or corrupting sensor measurements.
- Existing enclosures and mounts provide limited or no water resistance.

For at least the limitations described above there is a need for an elastomer encased motion sensor package.

BRIEF SUMMARY OF THE INVENTION

Embodiments of the invention enable a motion sensor package that is encased in an elastomer; the elastomer casing may provide shock isolation and water resistance. An elastomeric material such as silicone or rubber may be molded or cast around internal electronics that may include motion sensors, processors, batteries, and antennas.

One or more embodiments incorporate a shatter proof enclosure and mount for a motion capture element that enables a durable, secure, and safe coupling of the motion capture element to a piece of sporting, exercise or medical rehabilitation equipment, for example a baseball bat, hockey stick, lacrosse stick, helmet, skateboard, ski, snowboard, surfboard, golf club, tennis racquet, weight training bar, or any other equipment capable of movement. In addition, embodiments enable existing equipment that was not manufactured originally with a mount for electronics to be retrofitted with an enclosure and mount for motion capture element. The apparatus may be located internal or external to the piece of sporting equipment and may show a visual marker for use in visually obtaining motion in combination with electronically detected motion obtained with the motion capture sensor. For example, the outer portion of the enclosure may display a visual marker on the outer portion while the inner portion of the enclosure may be located on or within a shaft or grip in the handle portion of the equipment for example. In one or more embodiments, the grip may extend beyond the shaft and couple or aid in the coupling of the motion capture element with the shaft. One or more embodiments of the grip may include a grip that may roll down from the sides of a motion capture element to enable the motion capture element to be accessed without removing the grip from the shaft. The mount is configured to hold the enclosure to the piece of equipment wherein the enclosure holds the electronics and/or a visual marker. Embodiments of the invention do not require modifying the equipment, for example the baseball bat, tennis racquet, golf club, or other stick based equipment to include threads within the shaft. The apparatus may be flush mounted with the normal end of the equipment or have any desired length of extension from the end of the equipment. The mount also allows for the battery to be easily removed and replaced, for example without any tools. Other embodiments may make use of micro harvesting of energy to recharge batteries internal to the enclosure.

One or more embodiments of the mount include a shaft enclosure and expander that may be coupled with an attachment element, for example a screw that is aligned along an axis parallel to the axis of the shaft of the handle-based piece of equipment. The shaft enclosure and expander are situated within the handle portion of a handle-based piece of equipment such as a baseball bat, hockey stick, lacrosse stick, or golf club and engage in inner portion of the shaft or grip for example. In one or more embodiments, the screw is then rotated to move the shaft enclosure and expander together, which thus forces legs of the shaft enclosure in a direction orthogonal to the axis of the shaft. The force of the shaft enclosure against the inner wall of the shaft thus couples the shaft enclosure to the shaft non-permanently, for example based on the coefficient of static friction therebetween. After the shaft enclosure and expander are brought close enough together via the attachment element to securely couple the mount to the shaft or inside portion of a grip that is coupled to the shaft, then either the electronics package or a weight element is coupled with the shaft enclosure. In one or more embodiments, the weight element may weigh the same or approximately the same as the motion capture element so that there is no difference in weight to the piece of equipment with or without the motion capture element. In addition, certain sports may not allow the piece of equipment to be instrumented during match play. Embodiments of the weight element require no modification of the equipment. A cap is coupled with the shaft enclosure in either case, which provides a cover for the weight element or electronics package and which may include a visual marker and/or logo on the cap. Any other method or structure that enables a non-permanent mount of the apparatus that requires no modification of the shaft is in keeping with the spirit of the invention. Other embodiments may make use of a spear collet that enables coupling of a motion capture sensor with this type of mount to a stick or handle-based piece of equipment having a small hole in the end of the rubber grip on the handle. Other embodiments may utilize a shock puck that surrounds the enclosure and absorbs sudden shocks to the motion capture sensor within the enclosure, or otherwise dampens vibrations from the piece of equipment. Other embodiments may couple with helmets to obtain concussion related acceleration data, or obtain motion data related to board based sports such as snowboards, surfboards, skateboards as well as skis.

If the electronics package is installed, then generally a positive battery contact, printed circuit board (PCB), an insulator or insulative spacer, with negative electrical contact and battery may be installed between the shaft enclosure and cap. The electronics that may be coupled with the PCB for example may include active motion capture electronics that are battery powered, passive or active shot count components, for example a passive or active radio frequency identification (RFID) tag. Embodiments of the electronics may include motion capture accelerometers and/or gyroscopes and/or an inertial measurement unit along with wireless transmitter/receiver or transceiver components. The RFID tag enables identification of the specific piece of equipment, for example to determine which piece of equipment specific motion capture data is associated with. Identification information for example enables golf shots for each club associated with a golfer to be counted. Golf shots may optionally be counted via an identifier associated with motion capture electronics on the golf club in conjunction with a mobile computer, for example an IPHONE® equipped with an RFID reader that concentrates the processing for golf shot counting on the mobile computer instead of on each golf club. Optionally a wireless antenna may be coupled with the cap or alternatively may be implemented integral to the PCB as desired. In one or more embodiments, the antenna may be implemented as a Bluetooth® antenna embedded in an external portion of the enclosure, for example embedded in epoxy on an outer portion of the enclosure to maximize antenna coverage. One or more embodiments of the invention may also include a Global Positioning System (GPS) antenna. The GPS antenna may be mounted on the printed circuit board or may be located separate from the printed circuit board. One or more embodiments of the invention may also directly or indirectly communicate with any other sensors coupled with the club including motion analysis capture elements, strain gauges or any other type of sensor coupled for example with the golf club head. One or more embodiments of the invention may also utilize a battery coupling that attaches the battery to the shaft enclosure so that when the cap is removed, the battery does not fall out, unless intended. Embodiments may also utilize spring based electrical contacts to prevent loss of electrical conductivity under high acceleration.

As previously stated, one or more embodiments may include a weight element that is interchangeable with the electronic package in the mount. The electronics package may be removed for example to comply with any sporting rules that do not allow instrumented sporting equipment. For example, USGA Rule 14-3 on Artificial Devices prohibits any "unusual device", for example under 14-3(b) "For the purpose of gauging or measuring distance". Any embodiment of the electronics package including a GPS receiver may thus be removed prior to match play for example and replaced with a weight element to minimize the weight difference. For example, the weight element may for example weigh close to or the same as the electronics to minimize overall instrumented versus non-instrumented weight differences of the golf club. In addition, a manufacture may provide the mount on each club with a small weight for example, that is removed when the golfer decides to upgrade the club to include active instrumented electronics or passive shot count elements that weigh the same amount. The net effect on the club dynamics for swing then is negligible. In one embodiment, the plastic portion of the mount weighs 5.7 grams and the battery weighs 3 grams while the screw weighs 1.9 grams. Thus the mounting components have minimal weight and by selecting a weight element of the same weight of the electronics package, or elements within the shaft enclosure and cap that are replaced by the weight element, the golfer feels no change in club weight when upgrading to an instrumented club. The same weight element may be utilized with respect to embodiments of the invention in all other sports and pieces of equipment used in those sports, as one skilled in the art will appreciate.

The visual marker may be mounted on the cap for use with visual motion capture cameras. An equipment number may also be displayed on in a display area of the cap to indicate which type or specific piece of equipment is associated with the motion capture sensor, e.g., a club number is associated with the golf club. Embodiments of the visual marker may be passive or active, meaning that they may either have a visual portion that is visually trackable or may include a light emitting element such as a light emitting diode (LED) that allows for image tracking in low light conditions respectively. This for example may be implemented with a graphical symbol or colored marker at the cap of the mount on the shaft at the end of the handle for example. Motion analysis may be performed externally, for example using a camera and computer system based on the visual marker in any captured images. The visual data may also be utilized in motion analysis in combination with any wireless data from any installed electronics package.

Enclosures and mounts containing motion sensors and other electronics may be susceptible to impact events. For example, in sports applications such as baseball, the equipment may be specifically designed to impact an object such as a ball. While the choice of location of the enclosure and/or mount on the equipment may mitigate the impact risk, it cannot necessarily eliminate it. One or more embodiments therefore contain a protective layer, either surrounding the enclosure or integrated into the enclosure, to protect users and spectators in the event of an impact. The protective layer may for example be designed to maintain its integrity during an impact, and to prevent fragments of the enclosure or the enclosed components from exiting the enclosure after an impact.

In one or more embodiments the protective layer may comprise an elastomer, such as for example silicone rubber or any other flexible material. In one or more embodiments the protective layer may comprise a mesh that for example flexes during impact or otherwise maintains its integrity. A mesh for example may be designed with a sufficiently fine spacing between filaments to prevent fragments of any substantial size from exiting the mesh. A mesh may be for example integrated into the material of the enclosure, or attached around the enclosure. In one or more embodiments the protective layer may comprise a shatter proof or shatter resistant material, such as for example acrylic or polycarbonate. One or more embodiments may provide multiple layers of protective material, such as for example a mesh surrounding a layer of elastomer.

One or more embodiments may encase all electronic components in a layer of elastomer. Components that are encased may include for example motion sensors, such as an accelerometer and a gyro, a microprocessor, a wireless antenna, and a battery. The layer of elastomer may surround and protect all of the electronic components. It may be configured to provide shock isolation for the electronic components, and to provide a water resistant barrier around these components. Any elastomer may be used, including for example, without limitation, silicone, natural rubber, synthetic rubber, and polyurethane.

In one or more embodiments the size and shape of the elastomer layer may match a component of an item of sports equipment; the sensor package may be installed in the sports equipment by replacing the original component with the elastomer encased sensor package. For example, the elastomer layer may be formed to be a skateboard riser. The sensor electronics are then integrated directly into the riser. Installing the sensor package for the skateboard then involves simply replacing the original riser with the sensor package riser.

One or more embodiments may include both an elastomer layer that encases electronic components and an outer housing into which the elastomer encased package is placed. The outer housing may comprise for example a receiver portion with a cavity that holds the elastomer encased package, and a lid portion that fits onto the receiver portion. The closed outer housing may completely surround the elastomer layer. One or more embodiments may have a receiver and lid that are cylindrical and threaded so they can be screwed together to close the housing. One or more embodiments may include an installation and removal tool that is used to screw the lid onto or off of the receiver.

In one or more embodiments the outer housing may have a size and shape that fits into a cavity in an item of sports equipment. Such a cavity may exist in or be created in a surfboard, for example, or in a baseball bat at either the knob end or the tip end. In one or more embodiments the receiver portion or the lid portion of the outer housing may be integrated into an item of sports equipment. For example, a cavity with threads may be machined into the tip of a baseball bat; this cavity then functions as the receiver portion of the outer housing.

One or more embodiments may include a dummy weight that can replace the elastomer enclosed sensor package without substantially changing the overall weight of the item into which the sensor package is installed.

One or more embodiments may include a golf club grip adapter that is used to attach an outer housing to a golf club grip. The adapter may for example have a tube that is inserted through the top of a golf club grip. A protrusion on the receiver portion of the outer housing may fit into the tube of the adapter to attach the sensor package to the club.

BRIEF DESCRIPTION OF THE DRAWINGS

The above and other aspects, features and advantages of the ideas conveyed through this disclosure will be more apparent from the following more particular description thereof, presented in conjunction with the following drawings wherein:

FIG. 4A illustrates an exploded view "A" of the main mount components of a second embodiment of the invention along with the positive and negative battery contact and battery, while view "B" shows a bottom oriented view of the insulator, positive and negative battery contact, electronics package, here a printed circuit board or PCB and cap.

FIG. 4B illustrates a perspective view of the shaft enclosure and insulator of a second embodiment of the invention along with the positive and negative battery contact and battery.

FIG. 4C illustrates a perspective view of the insulator along with the positive and negative battery contact and battery.

FIG. 4D illustrates a perspective close-up view of the positive battery contact.

FIG. 4F illustrates a first side of the embodiment of the insulator of FIG. 4E.

FIG. 4G illustrates a second side of the embodiment of the insulator of FIG. 4E.

FIG. 4H illustrates a cross section view "A" of FIG. 4F.

FIG. 4I illustrates a bottom view of the embodiment of the insulator of FIG. 4E.

FIG. 5 illustrates a close up perspective view of the PCB and associated positive and negative contacts that are configured to make an electrical connection with the positive battery contact and the negative battery contact respectively.

FIG. 6B illustrates the embodiment of FIG. 6A as shown from the top side of the insulator.

FIG. 34 illustrates an elastomer encased motion sensor package integrated into a skateboard riser.

FIG. 38 illustrates an embodiment that includes a golf club grip adapter; the adapter is pushed through the top of the grip and attaches to a protrusion on the outer housing of the sensor package.

DETAILED DESCRIPTION OF THE INVENTION

An elastomer encased motion sensor package will now be described. In the following exemplary description numerous specific details are set forth in order to provide a more thorough understanding of the ideas described throughout this specification. It will be apparent, however, to an artisan of ordinary skill that embodiments of ideas described herein may be practiced without incorporating all aspects of the specific details described herein. In other instances, specific aspects well known to those of ordinary skill in the art have not been described in detail so as not to obscure the disclosure. Readers should note that although examples of the innovative concepts are set forth throughout this disclosure, the claims, and the full scope of any equivalents, are what define the invention. One skilled in the art will recognize that embodiments of the invention may be utilized in any equipment capable of coupling with the apparatus. This includes any piece of sporting, exercise or medical rehabilitation equipment, for example a baseball bat, hockey stick, lacrosse stick, helmet, skateboard, ski, snowboard, surfboard, golf club, tennis racquet, weight training bar, or any other equipment capable of movement. The apparatus may be located internal or external to the piece of sporting equipment and may show a visual marker for use in visually obtaining motion in combination with electronically detected motion obtained with the motion capture sensor. For example, the outer portion of the enclosure may display a visual marker on the outer portion while the inner portion of the enclosure may be located on or within a shaft or grip in the handle portion of the equipment for example.

Figure 1:
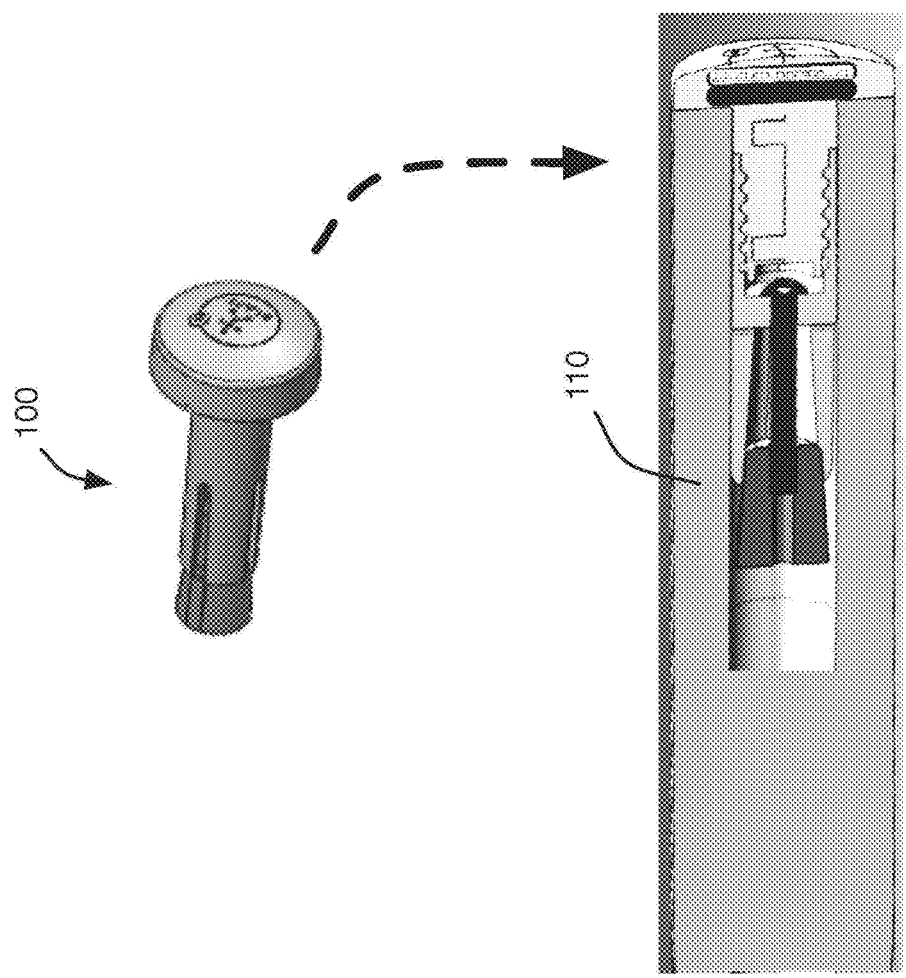
FIG. 1 illustrates an embodiment of the invention alone in perspective view and as mounted in a shaft of a handle-based piece of equipment as shown in cutaway view.

FIG. 1 illustrates an embodiment of the invention 100 alone in perspective view and as mounted in a shaft of a piece of movement equipment, for example a baseball bat, hockey stick, lacrosse stick, golf club, tennis racquet or any piece of equipment having a handle near shaft 110 as shown in cutaway view. Embodiments enable a mount for a new piece of equipment or that can be retrofitted in an existing piece of equipment. The mount may be located in the handle portion of the shaft, or for example within a grip that is to be attached to the shaft, and is configured to hold electronics and/or a visual marker.

Figure 2:
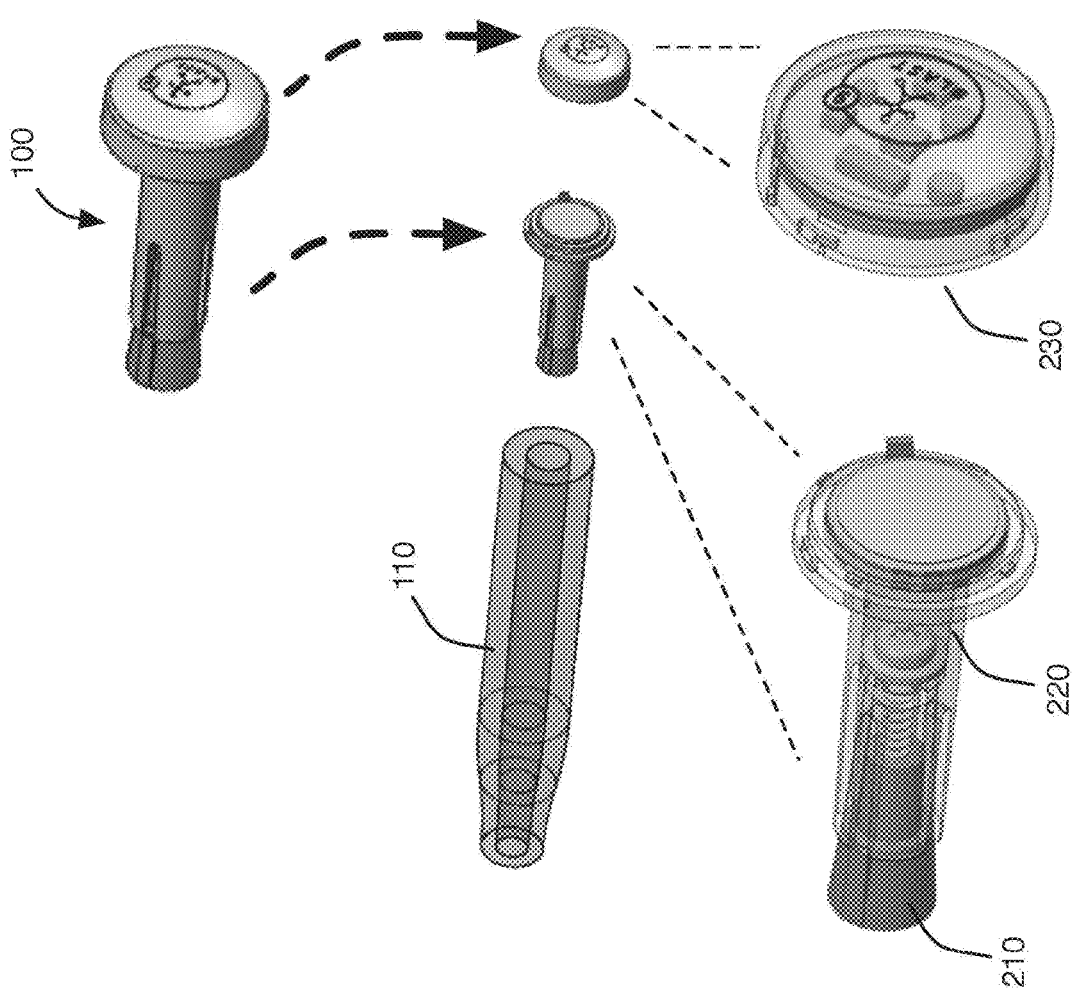
FIG. 2 illustrates an embodiment of the invention broken into an exploded view of the main components along with the shaft handle and blow up views of the major components in transparent shading.

FIG. 2 illustrates an embodiment of the invention broken into an exploded view of the main components along with the shaft handle and blow up views of the major components in transparent shading. One or more embodiments of the mount include enclosure or shaft enclosure 220 and expander 210 that may be coupled with an attachment mechanism, for example a screw aligned along an axis parallel to the axis of the shaft. The shaft enclosure and expander are situated within the handle, i.e., shaft 110. In one or more embodiments, the screw is then rotated to move the shaft enclosure towards the expander, which thus forces legs of the shaft enclosure in a direction orthogonal to the axis of the shaft. The force of the shaft enclosure against the inner wall of the shaft thus couples the shaft enclosure to the shaft based on the coefficient of static friction therebetween. Any other mechanism of coupling the shaft enclosure to a shaft in a non-permanent manner is in keeping with the spirit of the invention. After the shaft enclosure and expander are brought close enough together via the screw to securely couple the mount to the shaft, then either the electronics package or a weight element that may for example weigh the same as the electronics, is coupled with the shaft enclosure. Cap 230 is coupled with the shaft enclosure in either case, which provides a cover for the weight element or electronics package and which may include a visual marker and/or logo on the cap. One or more embodiments of the electronics package are removable to comply with any sporting rules that do not allow instrumented sporting equipment for example. Any other method or structure that enables a non-permanent mount of the apparatus that requires no modification of the shaft is in keeping with the spirit of the invention.

Optionally, an identification element or ID sticker, for example an RFID tag may be mounted within the enclosure, cap, or any other portion of the apparatus, for equipment identification, or shot count functionality. The identification element may also be implemented integral to, or coupled with the PCB in any manner as desired.

If the electronics package is installed, then generally a positive battery contact, printed circuit board or PCB, an insulator or insulative spacer, with negative electrical contact and battery may be installed between the shaft enclosure and cap. Optionally, a wireless antenna and/or GPS antenna may be coupled with the cap or alternatively may be implemented integral to the PCB as desired. Also see FIGS. 3A-C, 4, 4A-D and 9 for more detailed views.

Figure 3:
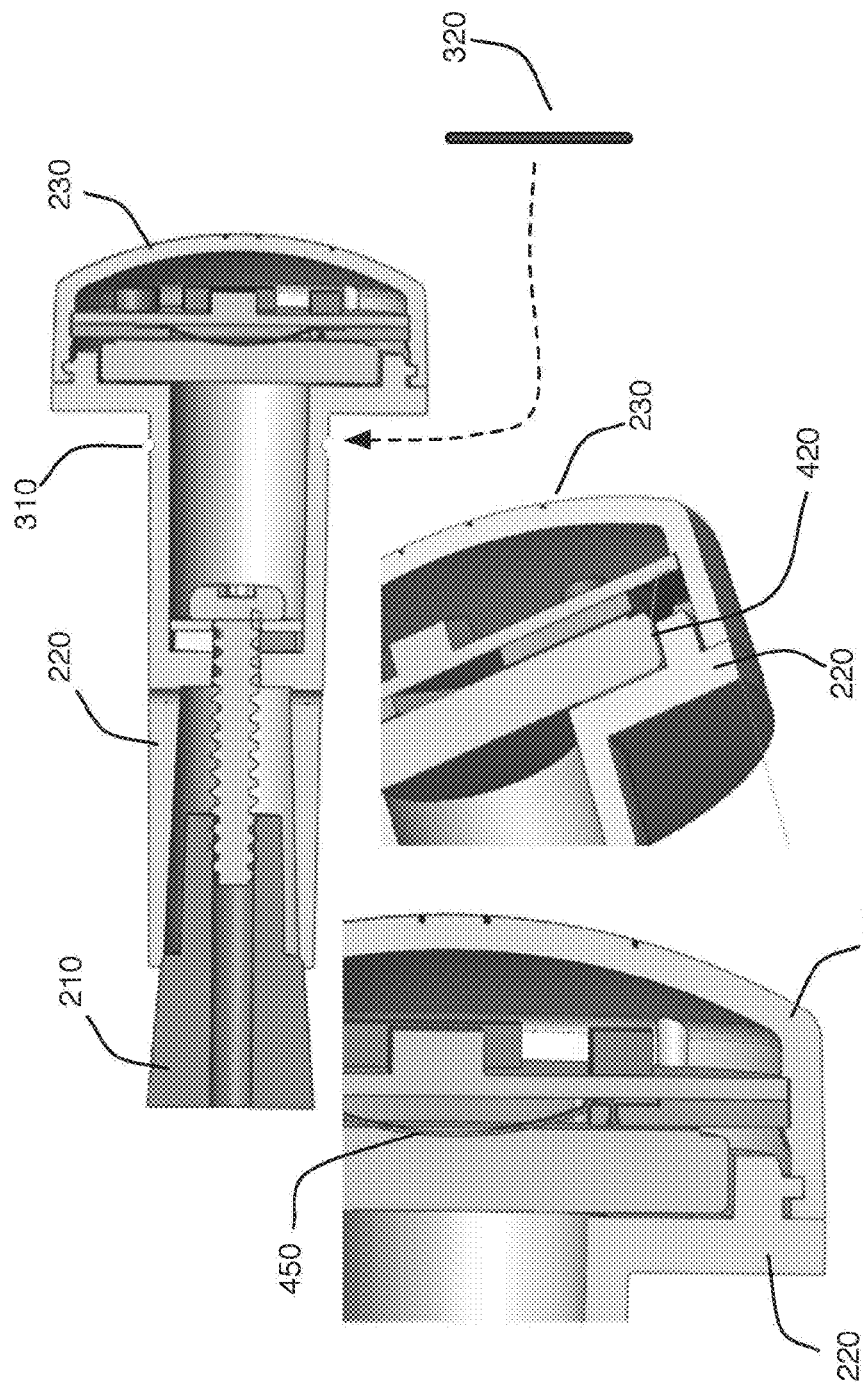
FIG. 3A illustrates a detailed cutaway view of the main components of an embodiment of the invention.
FIG. 3B illustrates a detailed cutaway view showing the negative battery contact, also shown in full in exploded view in FIG. 4.
FIG. 3C illustrates a detailed cutaway view showing the positive battery contact, also shown in full in exploded view in FIG. 4.

FIG. 3A illustrates a detailed cutaway view of the main components of an embodiment of the invention, specifically expander 210, shaft enclosure 220 and cap 230. FIG. 3B illustrates a detailed cutaway view showing negative battery contact 450, also shown in full in exploded view in FIG. 4. FIG. 3C illustrates a detailed cutaway view showing positive battery contact 420, also shown in full in exploded view in FIG. 4. Optional O-ring indentation 310 on shaft enclosure 220 provides a potential well for O-ring 320 to be located. Different size O-rings may be utilized to provide a secure fit on the end of shaft enclosure 220 on the end near cap 230.

Figure 4:
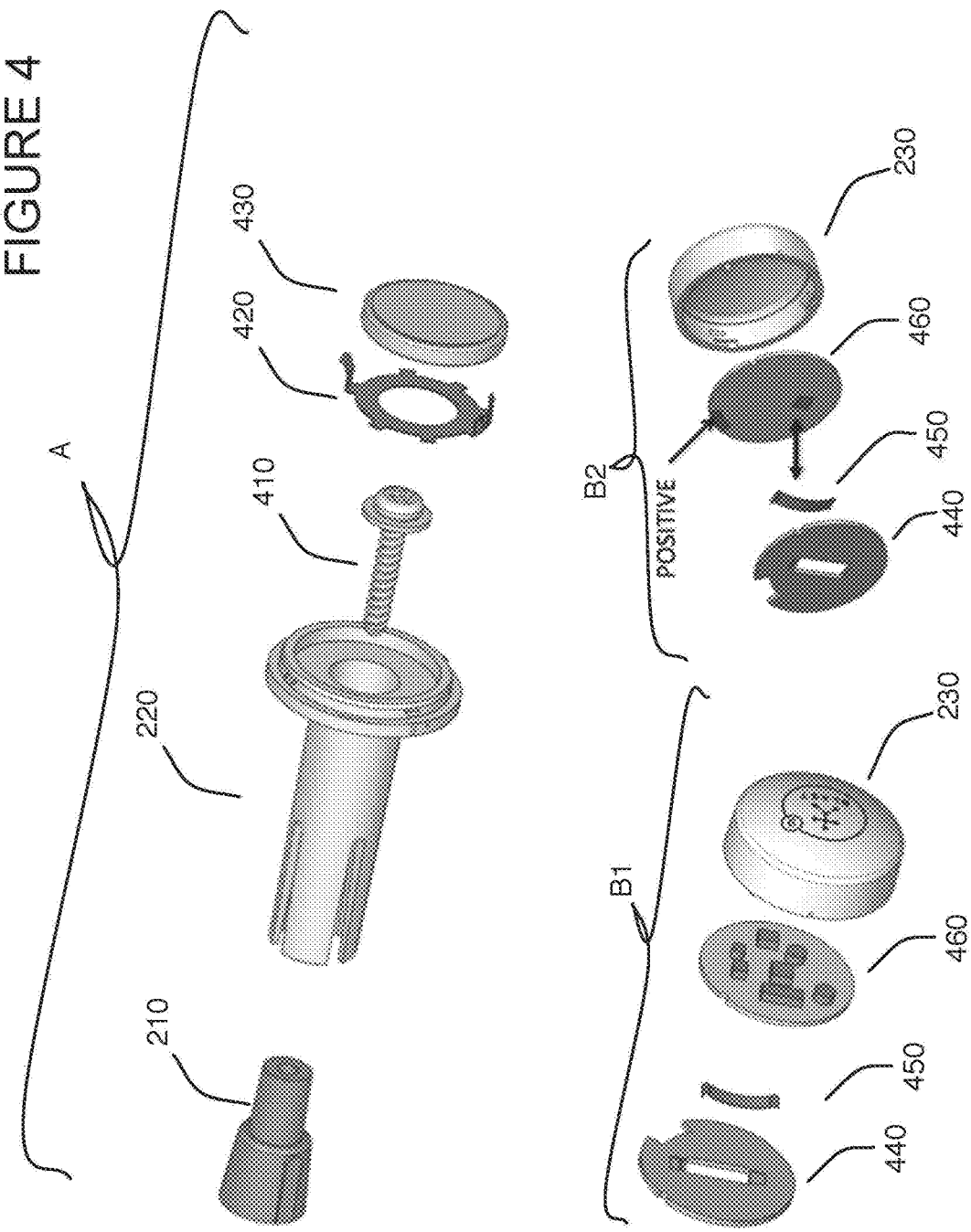
FIG. 4 illustrates an exploded view "A" of the main mount components along with the positive battery contact and battery, while view "B1" shows a top oriented view of the insulator, negative battery contact, electronics package, here a printed circuit board or PCB and cap, while view "B2" shows a bottom oriented view of the same components shown in view "B1".

FIG. 4 illustrates an exploded view "A" of the main mount components, namely expander 210, shaft enclosure 220 along with screw 410, positive battery contact 420 and battery 430, while view "B1" shows a top oriented view of the insulator 440, negative battery contact 450, electronics package 460, here a printed circuit board or PCB and cap 230, while view "B2" shows a bottom oriented view of the same components shown in view "B1". The left portion of shaft enclosure 220 shows extensions or "legs" that allow for the shaft enclosure to radially expand when expander 210 is pulled along the axis shown by screw 410, when screw 410 is rotated. To keep expander 210 from simply rotating when screw 410 is rotated, expander 210 may include a protrusion (shown on the left side of the expander) that aligns in a slot formed by two of the shaft enclosure's legs. In this manner, expander 210 is pulled along the axis of the screw without rotating along that axis. Electronics package 460 for example may include active motion capture electronics that are battery powered, passive or active shot count components, for example a passive or active RFID tag, which for example may be coupled with electronics package 460 or for example coupled with insulator 440. In addition, a GPS antenna may also be coupled with electronics package 460 or cap 230 (see FIG. 9A). Embodiments of the electronics may include motion capture accelerometers and/or gyroscopes and/or an inertial measurement unit along with wireless transmitter/receiver or transceiver components. The RFID tag enables golf shots for each club associated with a golfer to be counted. The RFID tag may be coupled with any component shown as RFID tags are tiny, for example cap 230 or shaft enclosure 220 or electronics package 460, or any other element. Golf shots may optionally be counted via an identifier associated with motion capture electronics on the golf club in conjunction with a mobile computer, for example an IPHONE® equipped with an RFID reader that concentrates the processing for golf shot counting on the mobile computer instead of on each golf club.

The visual marker may be mounted on cap 230, shown as a circle with dots in view B1 may be utilized with visual motion capture cameras. An equipment number, for example a golf club number may also be displayed on in a display area of the cap to indicate which club number is associated with the golf club, which is shown as a small circle with a number in it in view B1. Embodiments of the visual marker may be passive or active, meaning that they may either have a visual portion that is visually trackable or may include a light emitting element such as a light emitting diode (LED) that allows for image tracking in low light conditions respectively. This for example may be implemented with a graphical symbol or colored marker at the cap of the mount on the shaft at the end of the handle for example. Motion analysis may be performed externally, for example using a camera and computer system based on the visual marker in any captured images. The visual data may also be utilized in motion analysis in combination with any wireless data from electronics package 460.

FIG. 4A illustrates an exploded view "A" of the main mount components of a second embodiment of the invention, namely expander 210a, with ribs slightly offset with respect to expander 210 of FIG. 4. In addition, FIG. 4A also shows a second embodiment of shaft enclosure 220a having coupling elements that enable second embodiment of insulator 440a to securely couple to shaft enclosure 220a without falling out if the mount is turned upside down for example. In this embodiment, insulator 440*a* holds battery 430 inside while providing access to the battery so that positive battery contact 420*a* and negative battery contact 450*a* can make electrical contact with battery 430. View "B" shows a bottom-oriented view of the insulator, positive and negative battery contact, electronics package, here a printed circuit board or PCB and cap. Weight element 490 can be any shape so long as weight element 490 fits within, or couples in any direct or indirect manner with shaft enclosure 220 or 220*a* and cap 230 for example. Weight element 490 can be made to weigh as near as desired to the weight of the components that it replaces, for example to comply with any sporting rules that do not allow instrumented sporting equipment, e.g., during competition. Weight element 490 can also be utilized with the embodiment shown in FIG. 4 as one skilled in the art will appreciate.

FIG. 4B illustrates a perspective view of shaft enclosure 220*a* and insulator 440*a* of the second embodiment of the invention of FIG. 4A along with the positive and negative battery contact 420*a* and 450*a* respectively (situated above holes in insulator 440*a*) along with battery 430 that is internally held within insulator 440*a*. Insulator 440*a* includes for example snap components, e.g., coupling elements 441 that couple with coupling elements 221 of shaft enclosure 220*a* so that insulator 440*a* and hence battery 430 do not fall out when the cap is removed. To remove insulator 440*a* and hence battery 430, tab 442 may be engaged with for example a finger, screw driver or other implement to disengage coupling elements 441 from coupling elements 221. Alignment component 443 enables rotational alignment of the insulator with the shaft enclosure.

FIG. 4C illustrates a perspective view of the insulator along with the positive and negative battery contact 420*a* and 450*a* respectively, and battery 430. Coupling elements 441 are shown on the top and bottom in the written page, however any type of coupling element may be utilized in keeping with the spirit of the invention as desired.

FIG. 4D illustrates a perspective close-up view of positive battery contact 420*a*. In one or more embodiments of the invention, the positive and negative battery contacts may utilize the same structure. Any type of positive and negative battery contacts may be utilized so long as they maintain electric connection between the battery and electronics package.

Figure 4E:
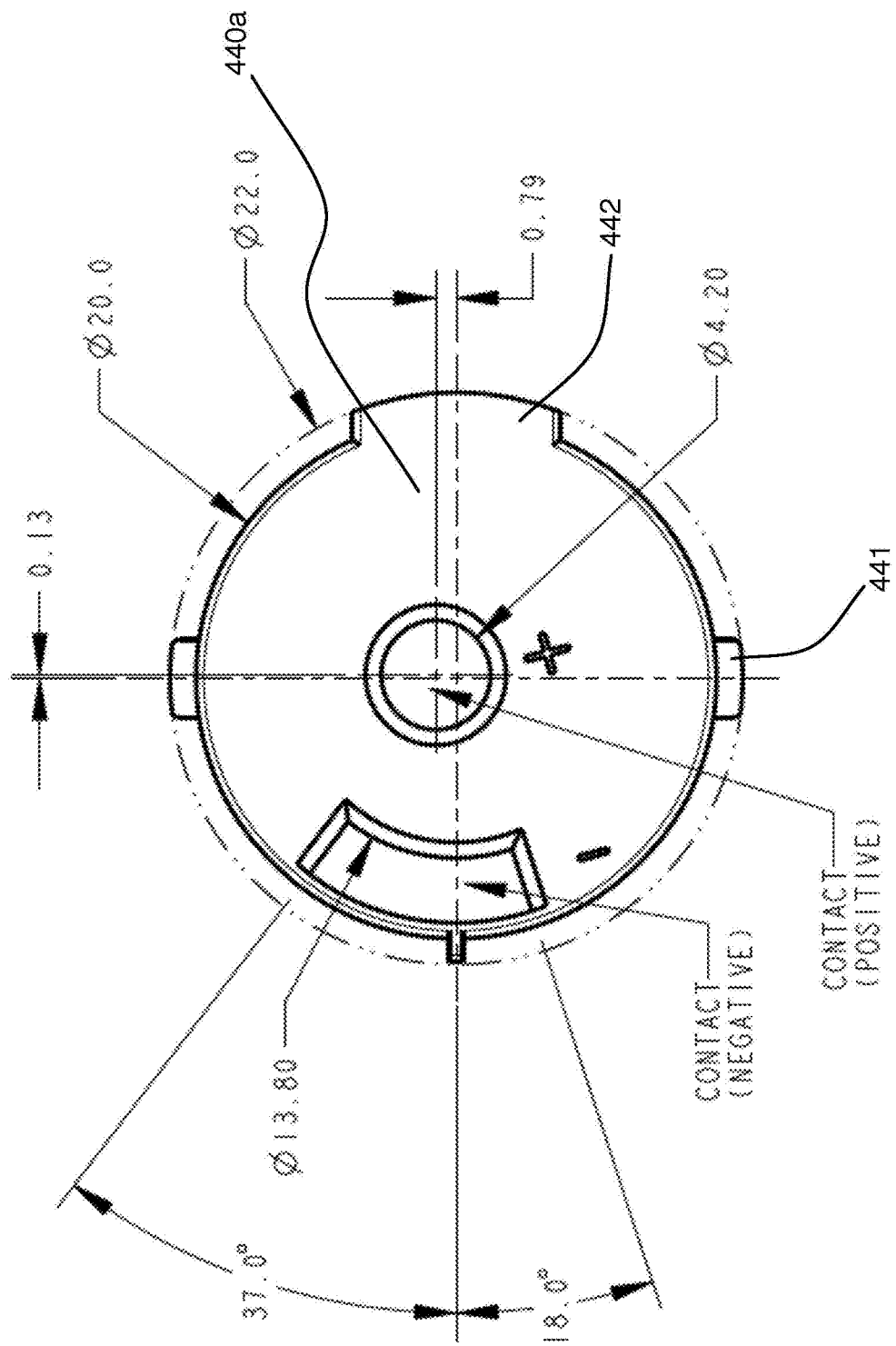
FIG. 4E illustrates a top view of an embodiment of the insulator that is configured to house a battery along with specific exemplary dimensions.

FIG. 4E illustrates a top view of an embodiment of insulator 440*a* that is configured to house a battery along with specific exemplary dimensions. To remove insulator 440*a* and hence the battery within insulator 440*a*, tab 442 may be engaged with for example a finger, screw driver or other implement to disengage coupling elements 441 from the coupling elements shown for example in FIG. 4B. In this figure, the numbers represent millimeters, and angle tolerances are within 2 degrees. As shown, this embodiment of insulator 440*a* is configured to house a 6.4 mm battery. Although not required for distribution in some countries, one or more embodiments of insulator 440*a* may be constructed to be compliant with EU Directive 2002/95/EC (RoHS) and EU Directive 2002/96/EC (WEEE). Embodiments may alternatively be constructed to be compliant with any other electrical or manufacturing standards as desired.

FIG. 4F illustrates a first side of the embodiment of the insulator of FIG. 4E. See also FIG. 4H for the cross section view. FIG. 4G illustrates a second side of the embodiment of the insulator of FIG. 4E. FIG. 4H illustrates a cross section view "A" of FIG. 4F. FIG. 4I illustrates a bottom view of the embodiment of the insulator of FIG. 4E.

FIG. 5 illustrates a close up perspective view of the electronics package 460 or PCB and associated positive contact 510 and negative contact 520 that are configured to make an electrical connection with the positive battery contact 420 and the negative battery contact 450 respectively. See also FIG. 4 for an exploded view of the relative positioning of the components shown in this figure.

Figure 5A:
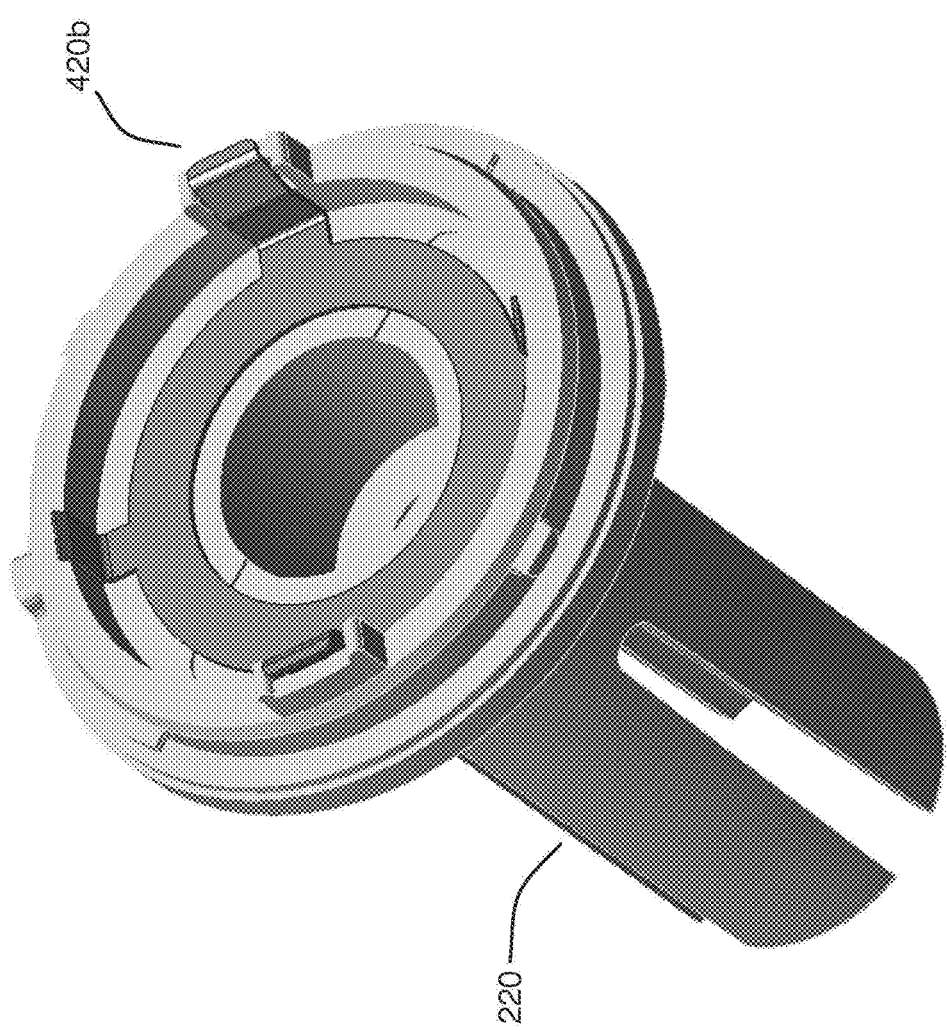
FIG. 5A illustrates a second embodiment of the positive battery contact located in the shaft enclosure.

FIG. 5A illustrates a second embodiment of positive battery contact 420*b* located in the shaft enclosure. This embodiment is symmetrical in that there are two opposing sets of upward projections from the base plane that contacts shaft enclosure 220. One of the opposing sets of upward projections of positive battery contact 420*b* are slightly wider and are positioned within areas on shaft enclosure 220 to allow for radially aligning positive battery contact 420*b* with respect to shaft enclosure 220.

Figure 6:
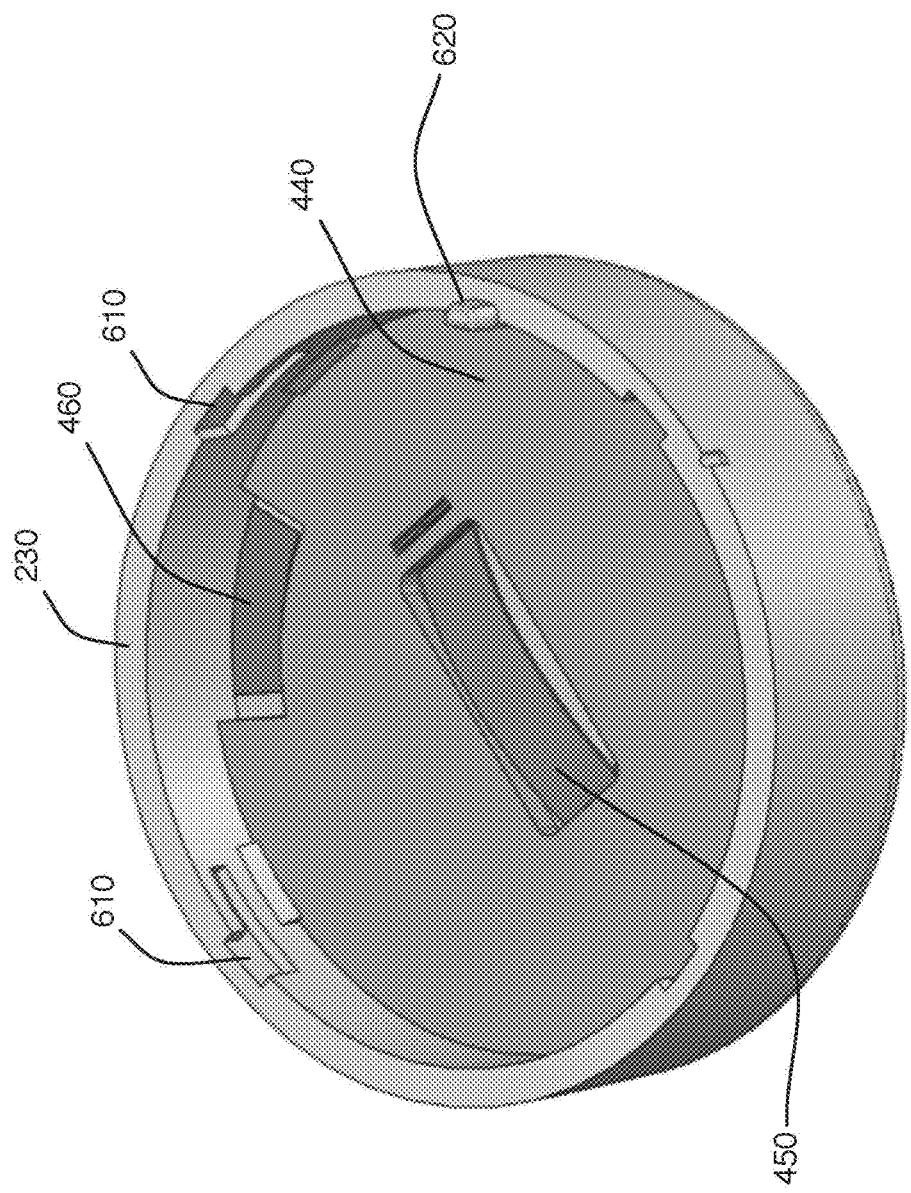
FIG. 6 illustrates a close up perspective view of the cap with PCB and negative battery contact showing along with a coupling element, here four coupling points, and alignment element.

FIG. 6 illustrates a close up perspective view of cap 230 with electronics package 460 or PCB and negative battery contact 450 coupled with insulator 440 showing along with a coupling element, here four coupling points 610 (with only the top two shown with reference number 610 with the inside portions visible, while the opposing two have only the initial slot openings in the cap visible), and alignment element 620.

Figure 6A:
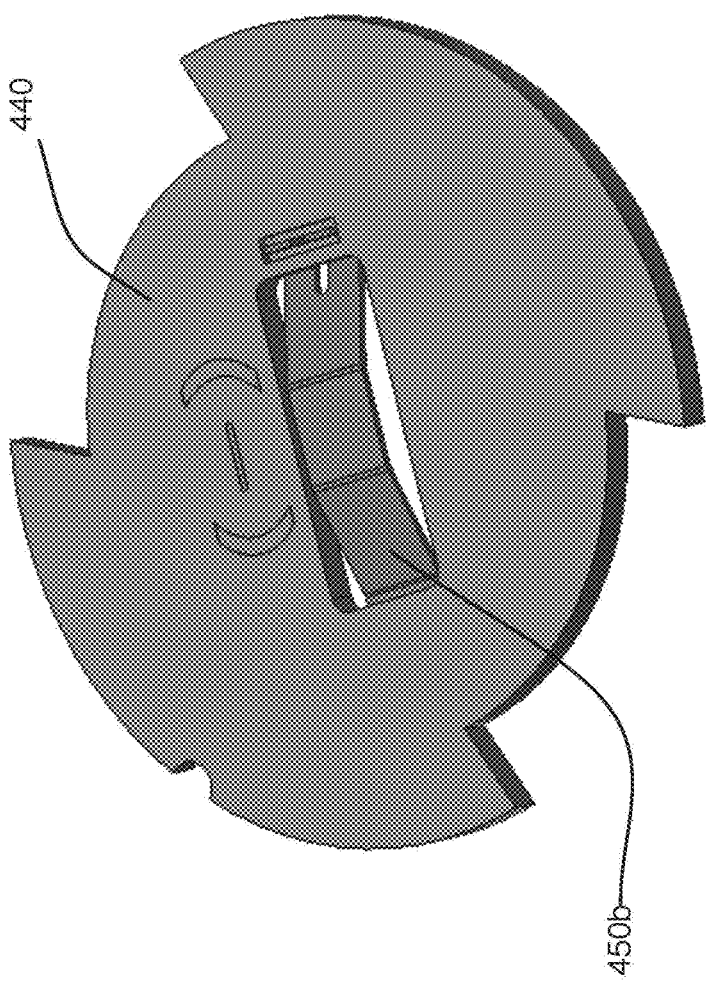
FIG. 6A illustrates a second embodiment of the negative batter contact having faceted surfaces as shown from the bottom side of the insulator.

FIG. 6A illustrates a second embodiment of the negative battery contact 450*b* having faceted surfaces as shown from the bottom side of insulator 440. FIG. 6B illustrates the embodiment of FIG. 6A as shown from the top side of the insulator. The right portion of negative battery contact 450*b* as shown may be folded over to engage insulator 440 while the opposing end of negative battery contact 450*b* may freely travel in a slot provided in insulator 440. The slot allows for the negative battery contact 450*b* to flatten, and hence travel in the slot, based on the force generated by placing the battery against negative battery contact 450*b*.

Figure 7:
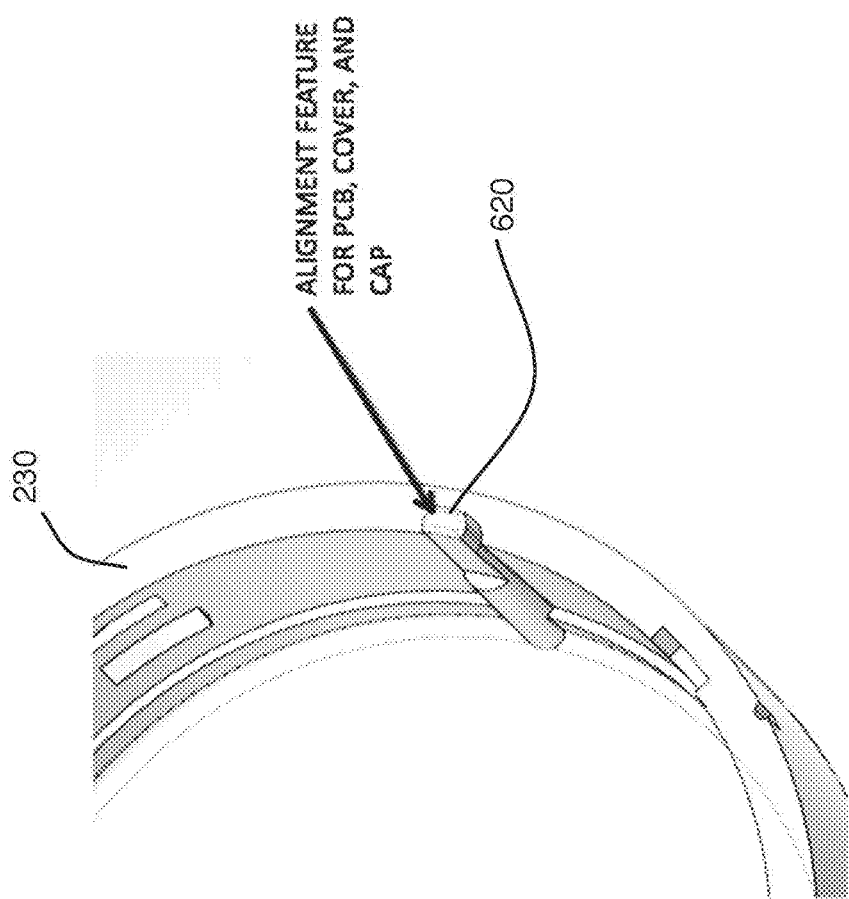
FIG. 7 illustrates a close up perspective view of the cap and alignment element.

FIG. 7 illustrates a close up perspective view of the cap and alignment element. Alignment element 620 allows for the angular alignment of insulator 440, and electronics package 460 that have indents on their sides to engage the alignment element 620. (See FIG. 4). By aligning insulator 440 and electronics package 460 with cap 230, positive battery contact 420 and negative electrical contact 450 are also aligned rotationally since they couple to respective components non-rotationally, for example.

Figure 8:
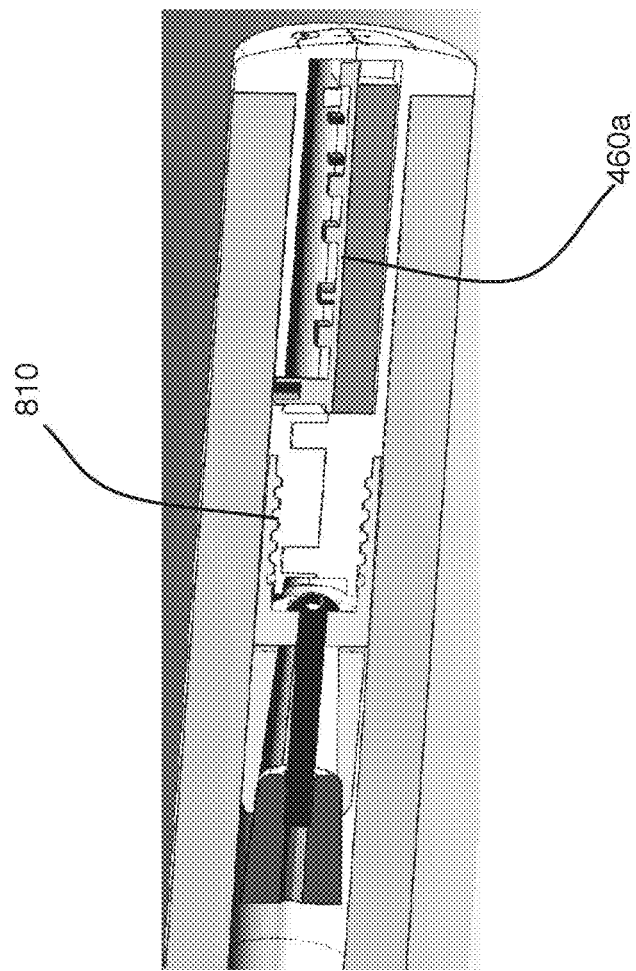
FIG. 8 illustrates a cutaway view of a second embodiment of the electronics package in longitudinal form along with a second embodiment of a coupling element.

FIG. 8 illustrates a cutaway view of a second embodiment of electronics package 460*a* in longitudinal form along with a second embodiment of a coupling element. Any other orientation of electronics is in keeping with the spirit of the invention so long as the mount is configured to hold the desired electronics package. Embodiments of the invention do not require modifying the piece of equipment, for example to include threads within the shaft. Embodiments of the invention also can be flush mounted with the normal end of a shaft or have any desired low profile extension from a non-instrumented club. Embodiments of the invention generally utilize a mount that is separate from the electronics so that the electronics package can be easily removed and replaced, or so that the battery can be easily removed and replaced, for example without any tools. As shown in this embodiment, a different coupling mechanism is used versus coupling points 610, namely threads 810 that engage shaft enclosure 220, which in this embodiment has corresponding threads.

Figure 9:
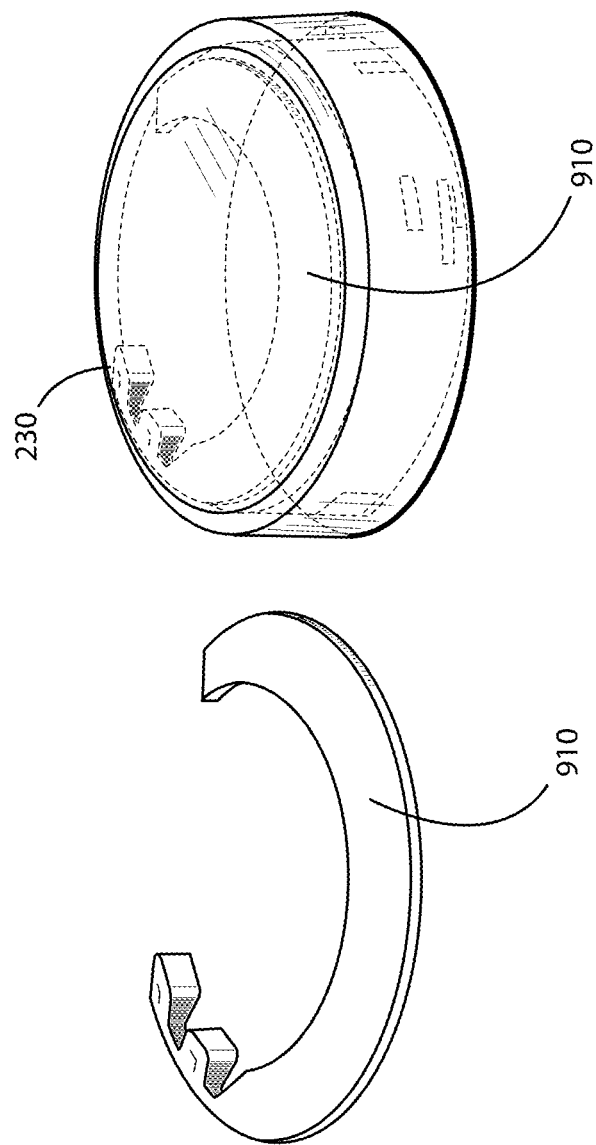
FIG. 9 illustrates an embodiment of a wireless antenna, for example a BLUETOOTH® antenna, configured to mount within the cap.

FIG. 9 illustrates an embodiment of wireless antenna 910, configured to mount within cap 230 as shown in the right portion of the figure. Alternatively, the wireless antenna may be coupled with the electronics package 460 or may include any conductive element in any shape that can radiate electromagnetic energy.

Figure 9A:
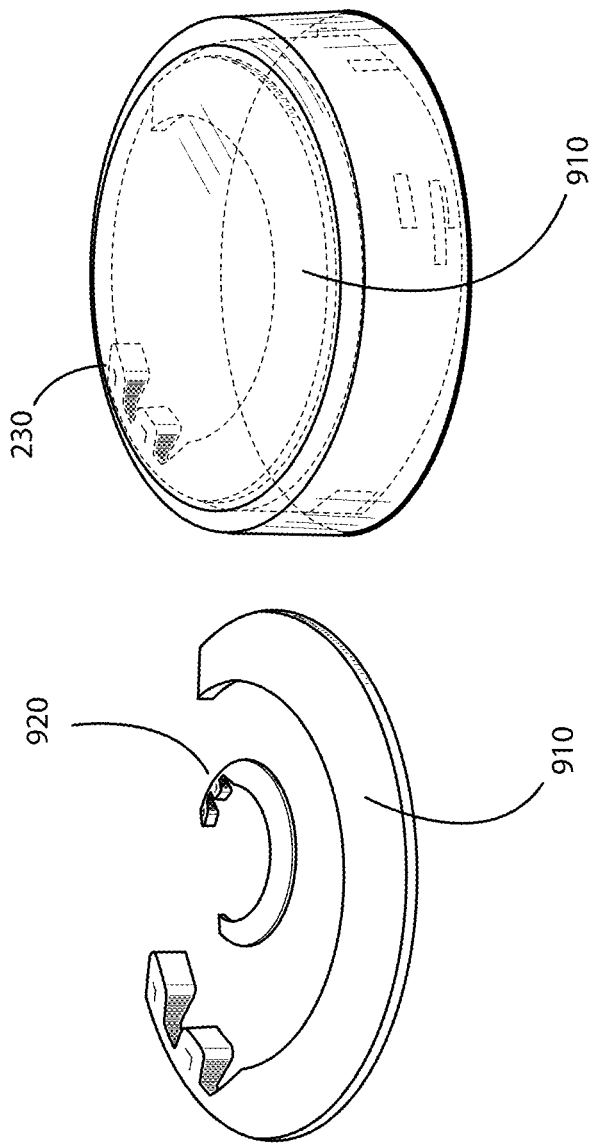
FIG. 9A illustrates an embodiment of the cap having two antennas, a wireless antenna, for example a BLUETOOTH® antenna and a GPS antenna.

FIG. 9A illustrates an embodiment of the cap having two antennas, a wireless antenna, for example a BLUETOOTH® antenna and a GPS antenna 920. The GPS antenna is optional and may be mounted in cap 230 as wireless antenna 910 is, or may be implemented in a different form factor or coupled with the PCB in any direct or indirect manner as one skilled in the art will appreciate. See also FIG. 18 for another embodiment of the antenna configuration.

Figure 10:
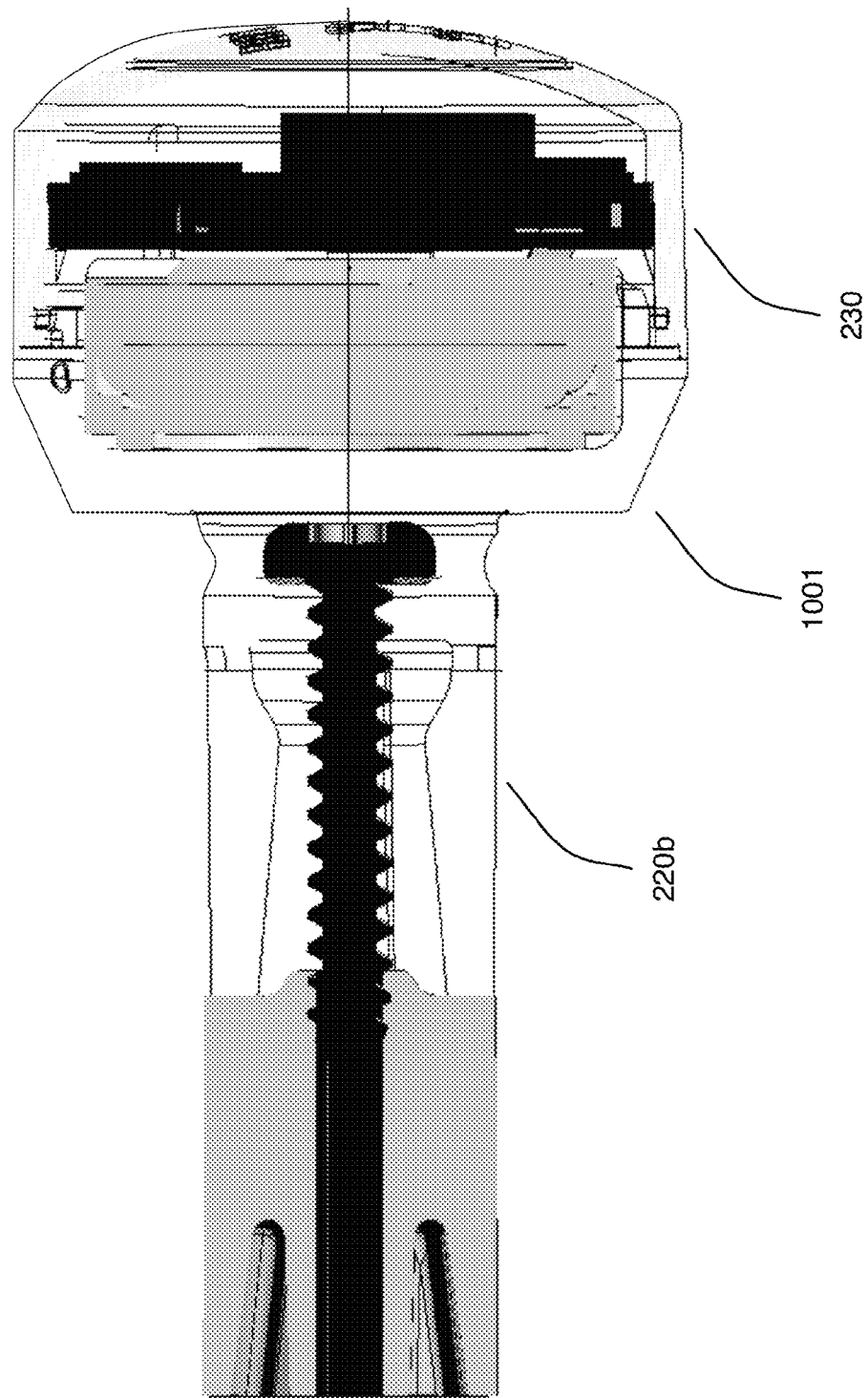
FIG. 10 shows an embodiment of the shaft enclosure having an angled area. The shaft enclosure couples with cap as is shown in the right portion of the figure.

FIG. 10 shows an embodiment of shaft enclosure 220*b* with angled area 1001. Shaft enclosure 220*b* couples with cap 230 as is shown in the right portion of the figure. Any other embodiment of the shaft enclosure detailed herein may be utilized on a shaft having a grip that either includes a hole or that does not include a hole and that wraps partially or fully around the motion capture element.

Figure 11:
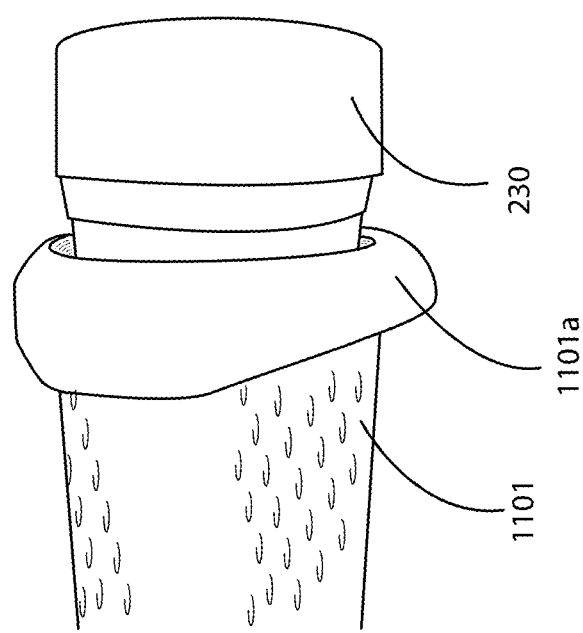
FIG. 11 shows an embodiment of the grip, for example having a hole in the top of the grip that allows for the grip to be rolled down the shaft as is shown and enabling access to the cap without removing the grip from the shaft.

FIG. 11 shows grip 1101, having a hole in the top of the grip that allows for the grip to be rolled down the shaft as is shown at area 1101*a*. This enables cap 230 to be exposed, removed or otherwise accessed without removing the grip from the piece of equipment for example.

Figure 12:
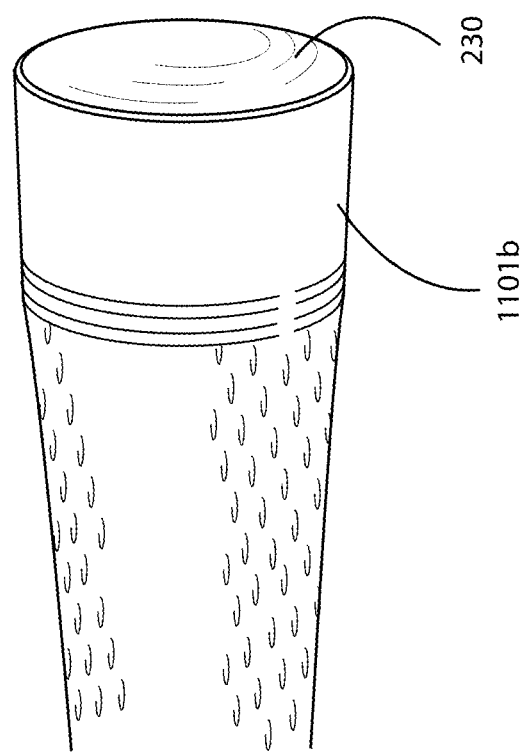
FIG. 12 shows the grip rolled back over the angled area and onto the side portions of the cap. This enables the end of the cap to be seen through the hole in the end of the grip, and enables the grip to provide extra support for the motion capture element.

FIG. 12 shows grip at area 1101*b* rolled back over angled area 1001 and onto the side portions of cap 230. This enables the end of the cap 230 to be seen through the hole in the end of the grip, and enables the grip to provide extra support for the motion capture element.

Figure 13:
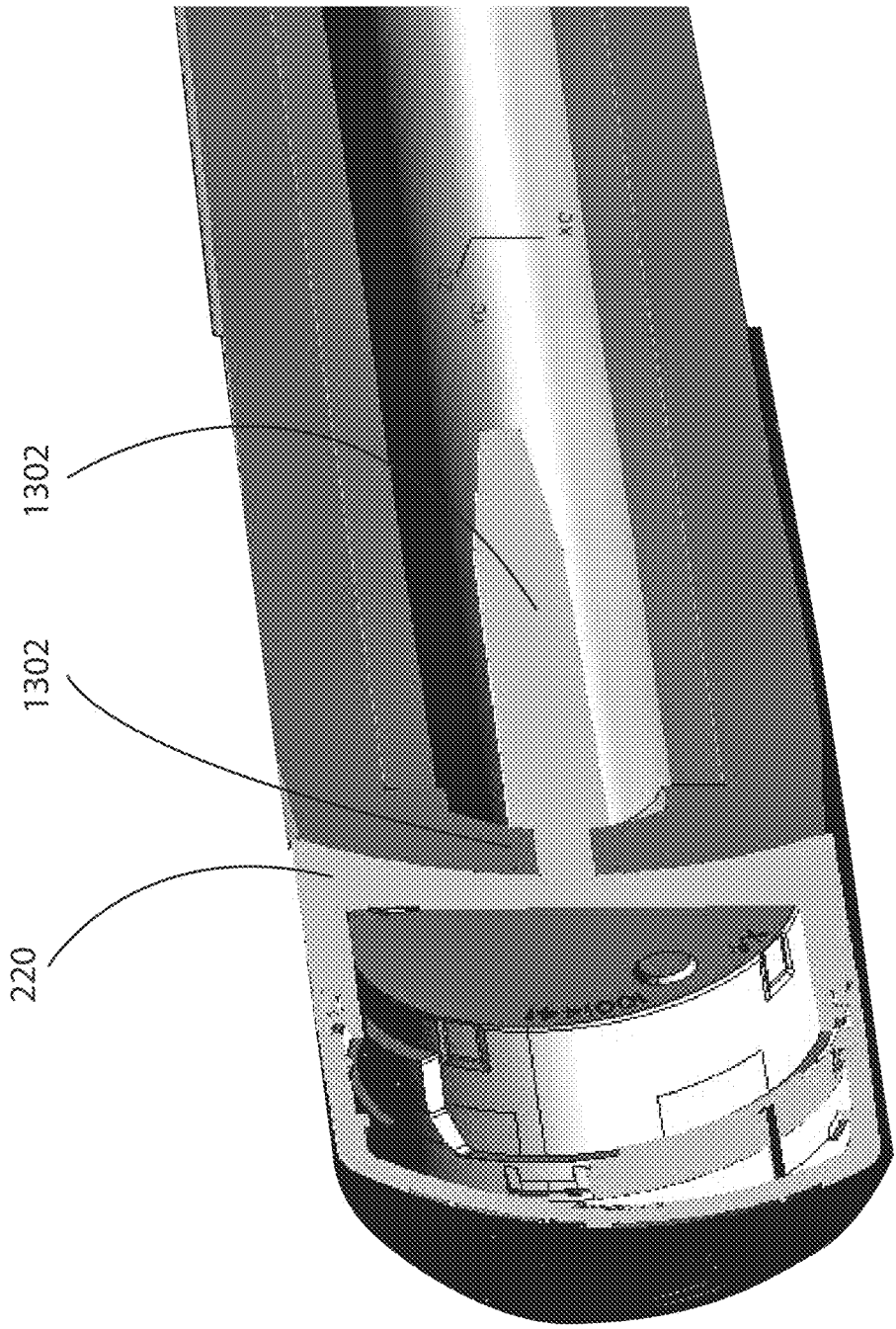
FIG. 13 illustrates a spear collet cutaway view of an embodiment of the invention.

FIG. 13 illustrates a spear collet cutaway view of an embodiment of the invention. Spear 1301 couples enclosure 220 with the hole 1302 in the handle-based piece of equipment. The spear has a narrower portion shown at the hole, but this is not required so long as the spear is capable of holding enclosure 220 to the handle.

Figure 14:
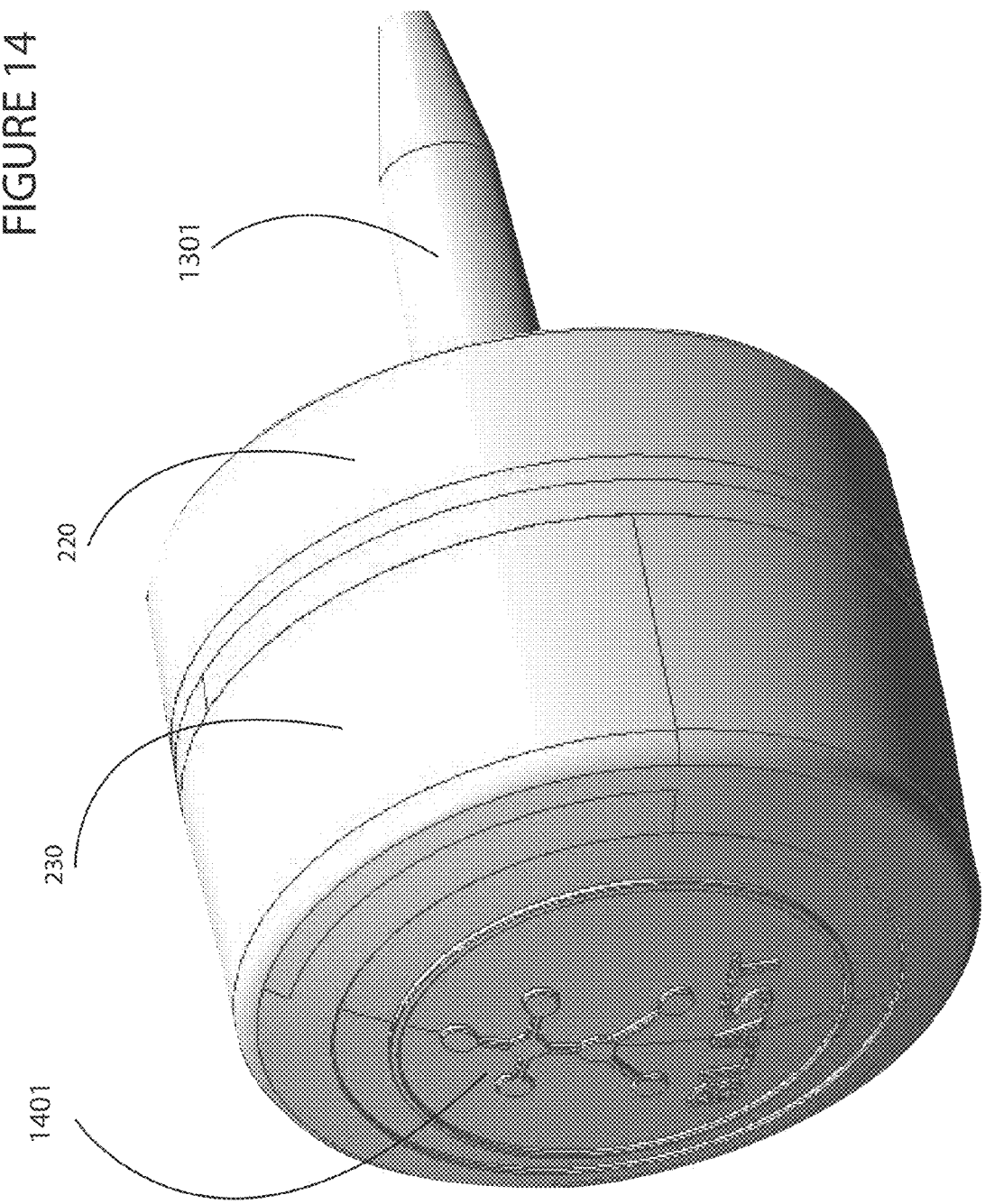
FIG. 14 illustrates a rear perspective view of the embodiment shown in FIG. 13.

FIG. 14 illustrates a rear perspective view of the embodiment shown in FIG. 13. As shown, visual marker 1401 for motion capture detection via visual methods is shown on cap 230 of enclosure 220.

Figure 15:
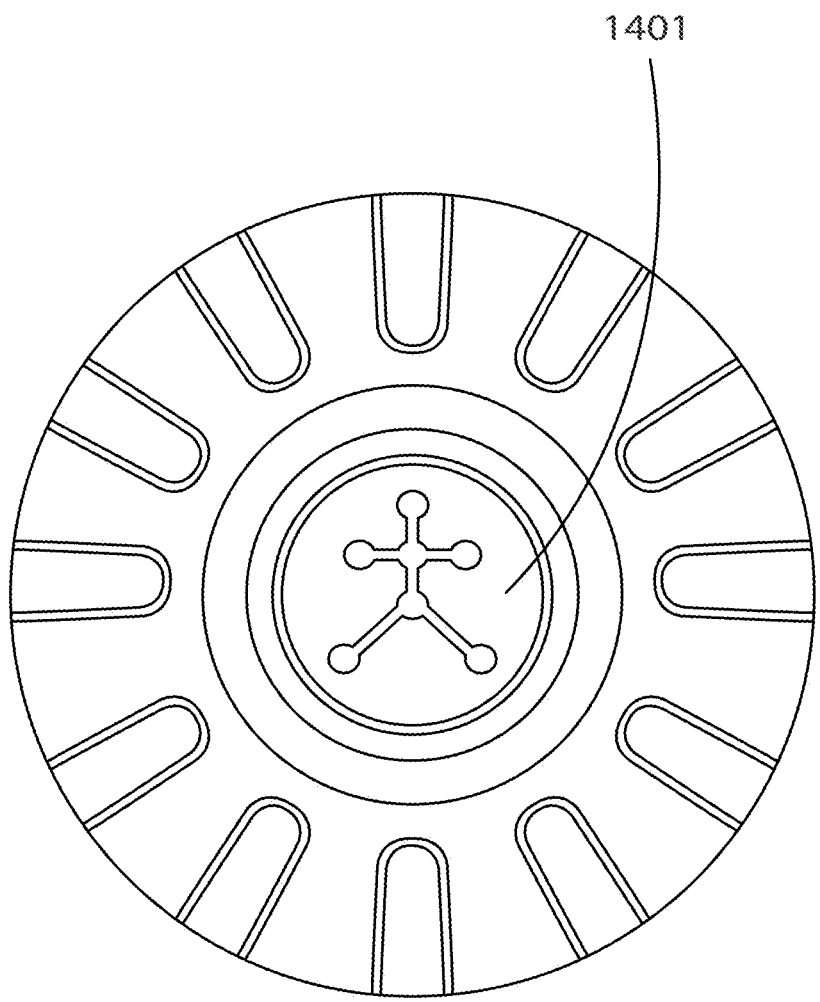
FIG. 15 illustrates a handle-based embodiment of the invention.

FIG. 15 illustrates a handle-based embodiment of the invention. As shown, visual marker 1401 is visible and in one or more embodiment may contain high contrast or active elements to enable easier visual detection of the orientation and/or motion of the motion capture sensor for example with a camera. The embodiment shown may be coupled with a baseball bat or other handle based piece of equipment for example.

Figure 16:
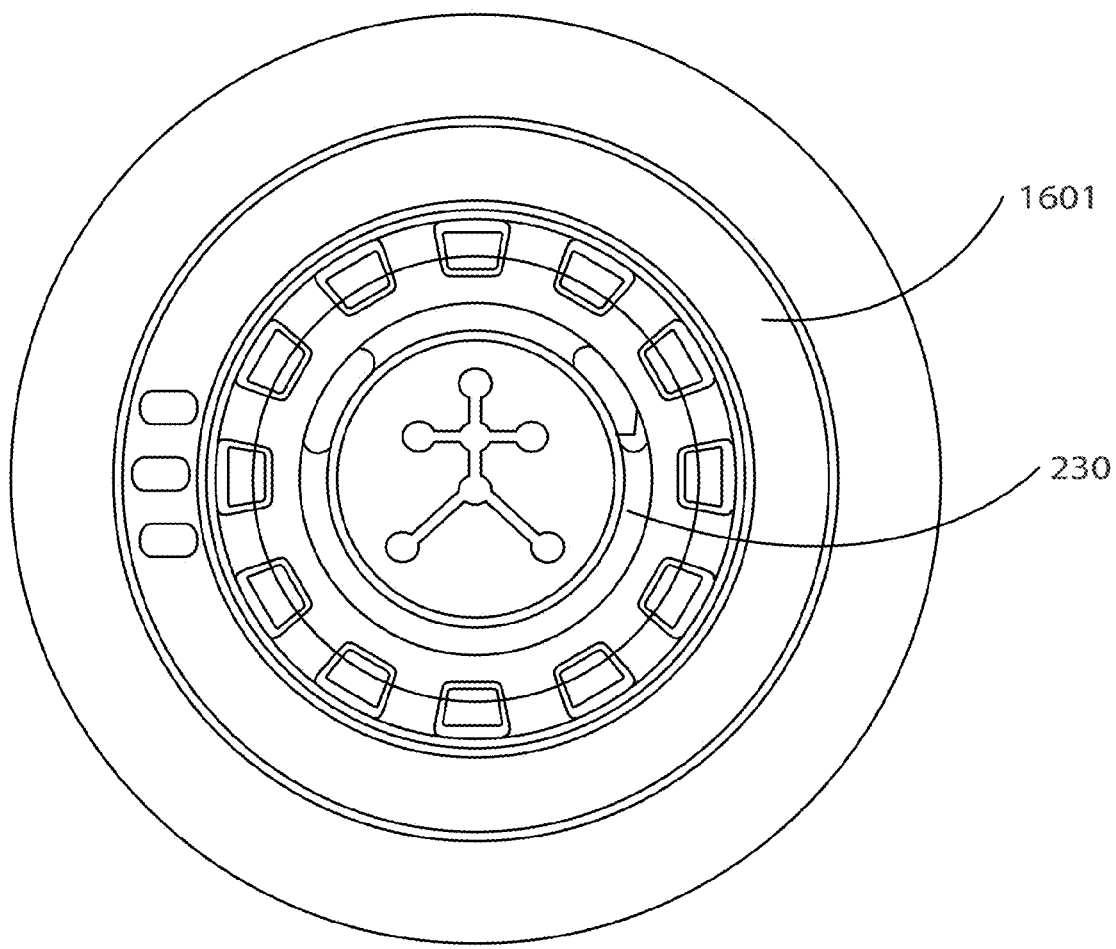
FIG. 16 illustrates a structural view of another handle-based embodiment of the invention.

FIG. 16 illustrates a structural view of another handle-based embodiment of the invention. As shown, cap 230, which covers the enclosure, is isolated from the piece of equipment via shock puck 1601. Shock puck 1601 may include any material that dampens or otherwise limits G-forces from the piece of equipment to assert force on the motion capture sensor.

Figure 17:
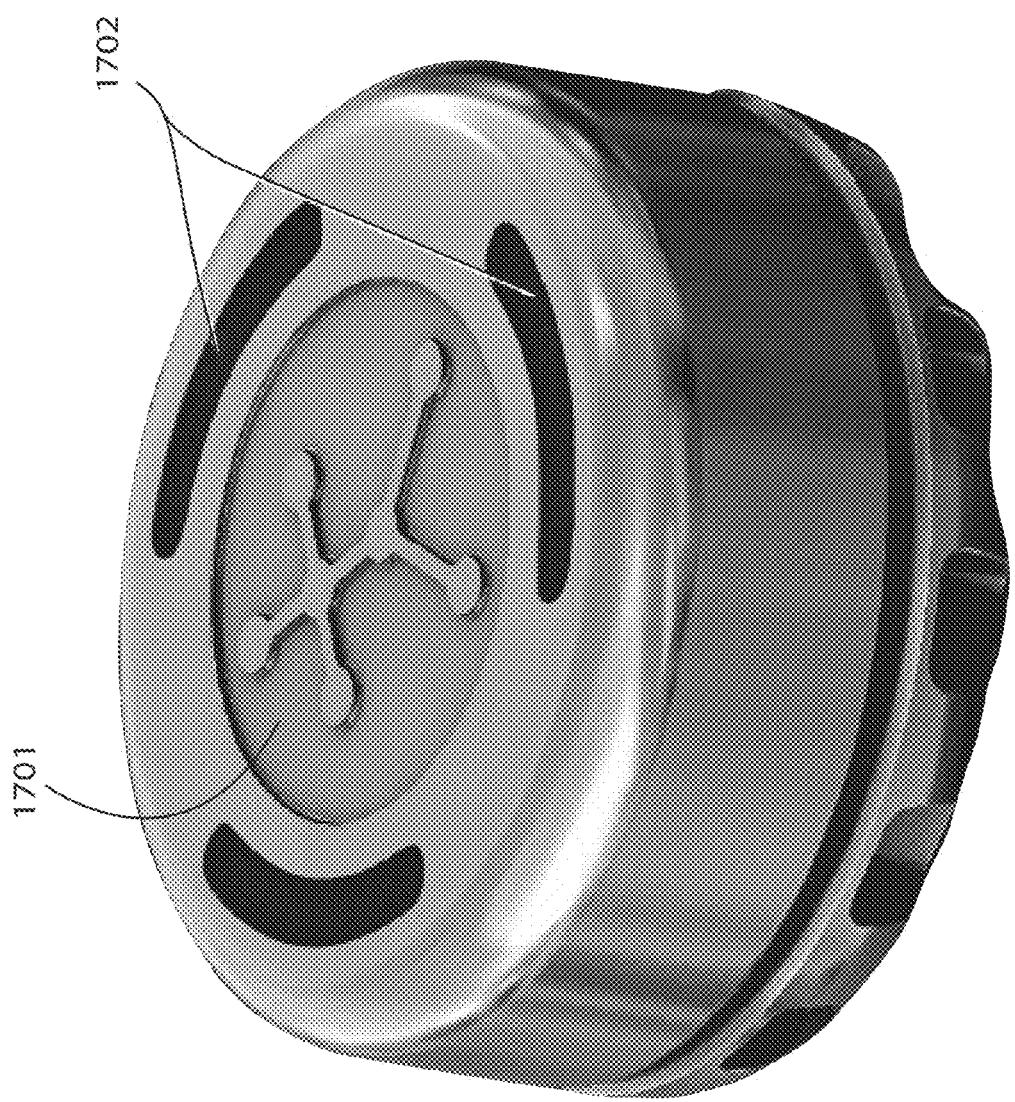
FIG. 17 illustrates another handle-based embodiment of the invention.

FIG. 17 illustrates another handle-based embodiment of the invention. As shown, uncovered portion 1701 may be utilized to house an antenna external to the inside portion of the enclosure. In one or more embodiments, areas 1702 may be made from any material that enables radio frequency waves to emanate from the internal volume of the enclosure. Alternatively, or in combination, the uncovered portion may provide an area for a small antenna that is then covered for protection as is shown in the next figure.

Figure 18:
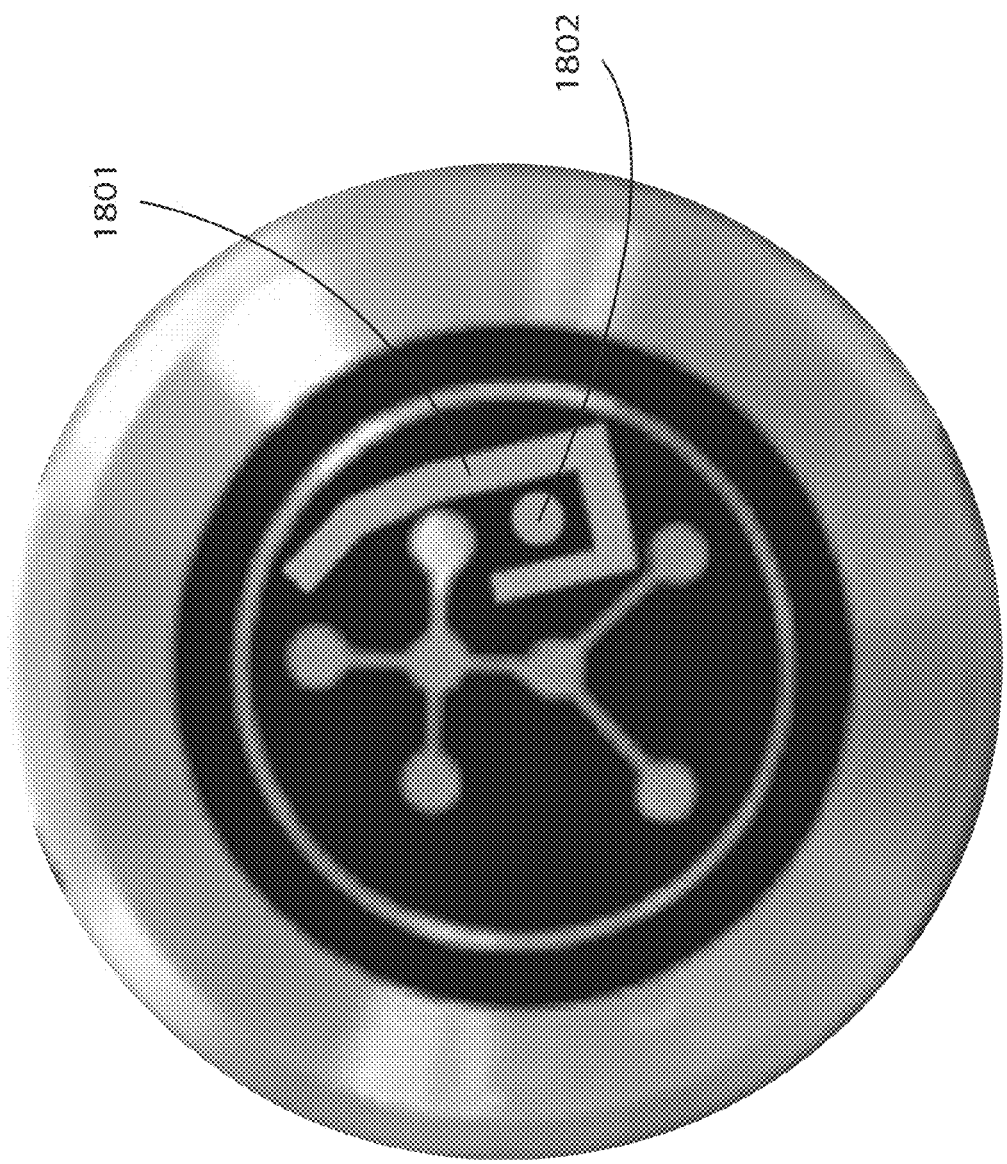
FIG. 18 illustrates the handle-based embodiment of the invention of FIG. 17 showing the location of the antenna on the outer portion of the enclosure.

FIG. 18 illustrates the handle-based embodiment of the invention of FIG. 17 showing the location of the antenna on the outer portion of the enclosure. As shown, antenna 1801 may be placed in the uncovered portion 1701 as shown in FIG. 17, which is shown in this figure partially filled with epoxy. Two holes may be drilled through the cap to provide feed lines for antenna 1801 and also for ground point 1802. The antenna and ground point may be covered as is shown in the next figure. Embodiments of the enclosure that are metallic and for example behave as an electromagnetic shield may utilize this type of antenna and provide for an extremely durable enclosure and exceptional antenna coverage for example.

Figure 19:
FIG. 19 illustrates the embodiment of FIG. 17 with the antenna shown in FIG. 18 covered with non-conductive material.

FIG. 19 illustrates the embodiment of FIG. 17 with the antenna shown in FIG. 18 covered with non-conductive material. As shown, the uncovered portion shown in FIG. 17 is covered at 1901 for example, and flush with the other portions of the cap to provide a finished cap for the enclosure that provides maximal antenna covered, while still providing a visual marker for bot electronic and visual motion capture sensing capabilities.

Figure 20:
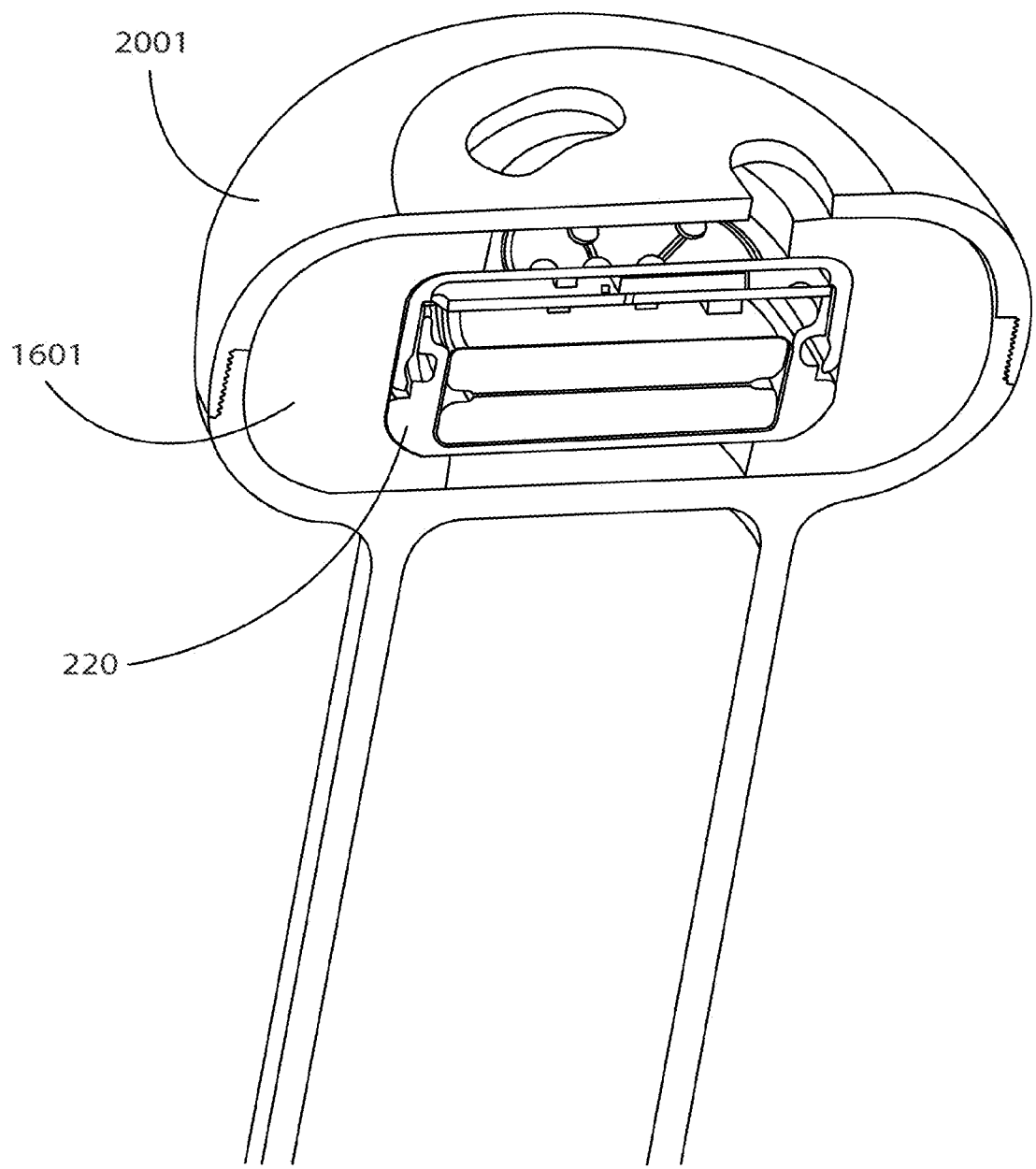
FIG. 20 illustrates a cutaway view of an embodiment of the invention coupled with a piece of equipment having a handle.

FIG. 20 illustrates a cutaway view of an embodiment of the invention coupled with a piece of equipment having a handle. As shown, shock puck 1601 surrounds enclosure 220 to provide high G-force shock protection to the internal components of the motion capture sensor. One or more embodiments of the invention may be covered with an outer protective area 2001, which may be transparent in one or more embodiments.

Figure 21:
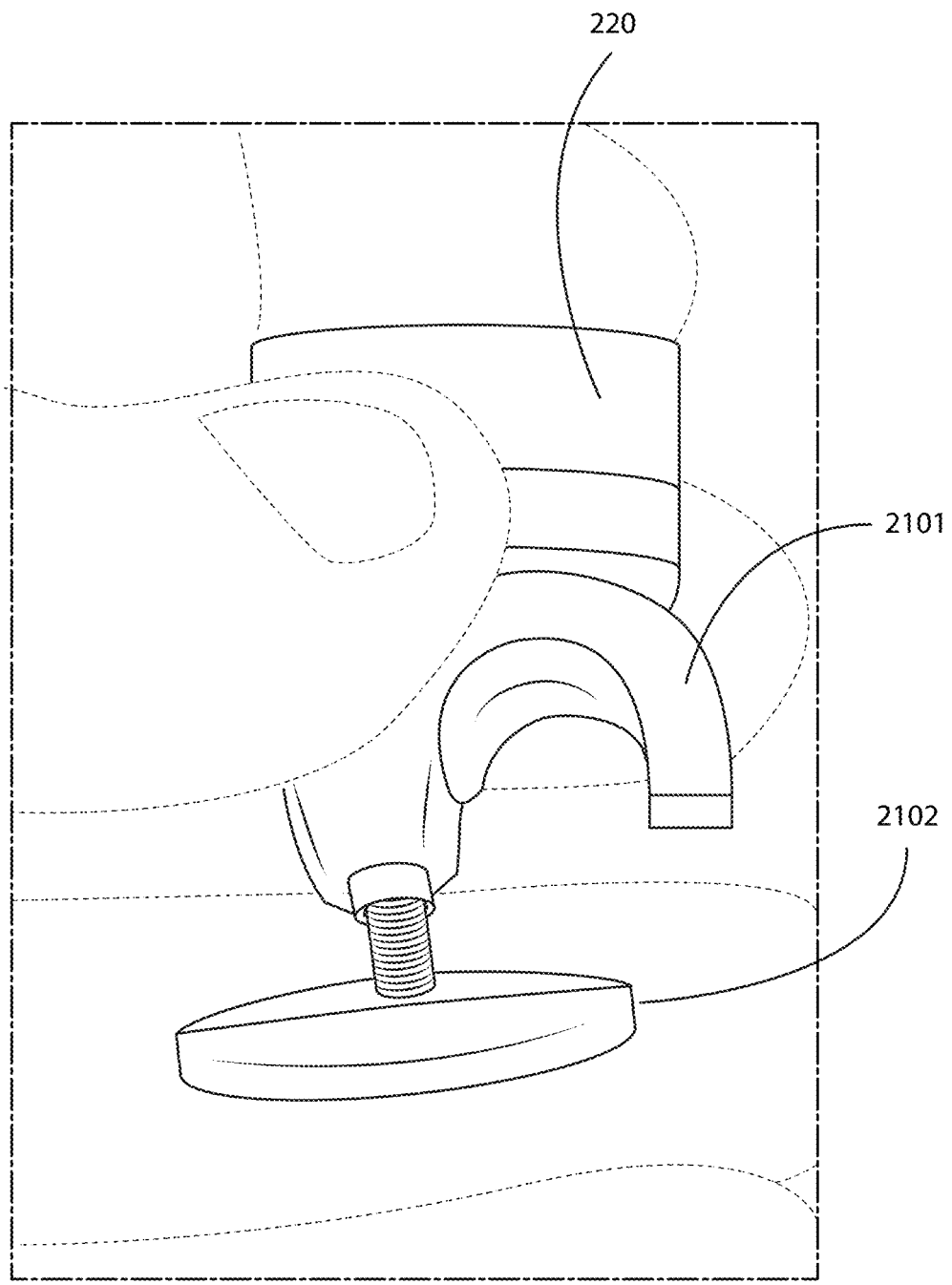
FIG. 21 illustrates an embodiment of the invention configured to couple with a helmet.

FIG. 21 illustrates an embodiment of the invention configured to couple with a helmet. As shown, enclosure 220 couples with mount 2101 that includes a half circle opening for example that may be fit around a helmet facemask tube or grill. Screw 2102 may be tightened to close the gap between the mount and the screw backing to couple enclosure 220 to a helmet.

Figure 22:
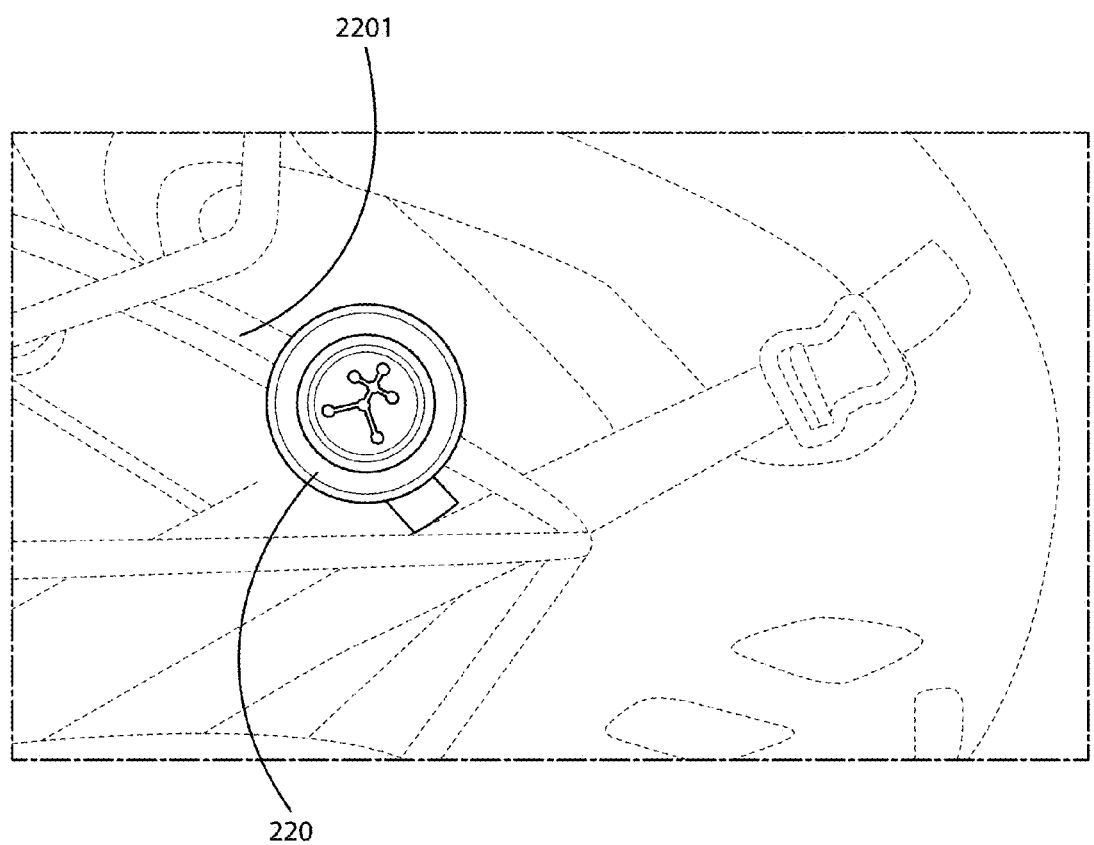
FIG. 22 illustrates the embodiment shown in FIG. 21 coupled with the helmet.

FIG. 22 illustrates the embodiment shown in FIG. 21 coupled with the helmet. As shown, enclosure 220 is coupled with helmet via facemask tube or grill 2201 as per the elements shown in FIG. 21. Any other method of coupling the enclosure with a helmet is in keeping with the spirit of the invention.

Figure 23:
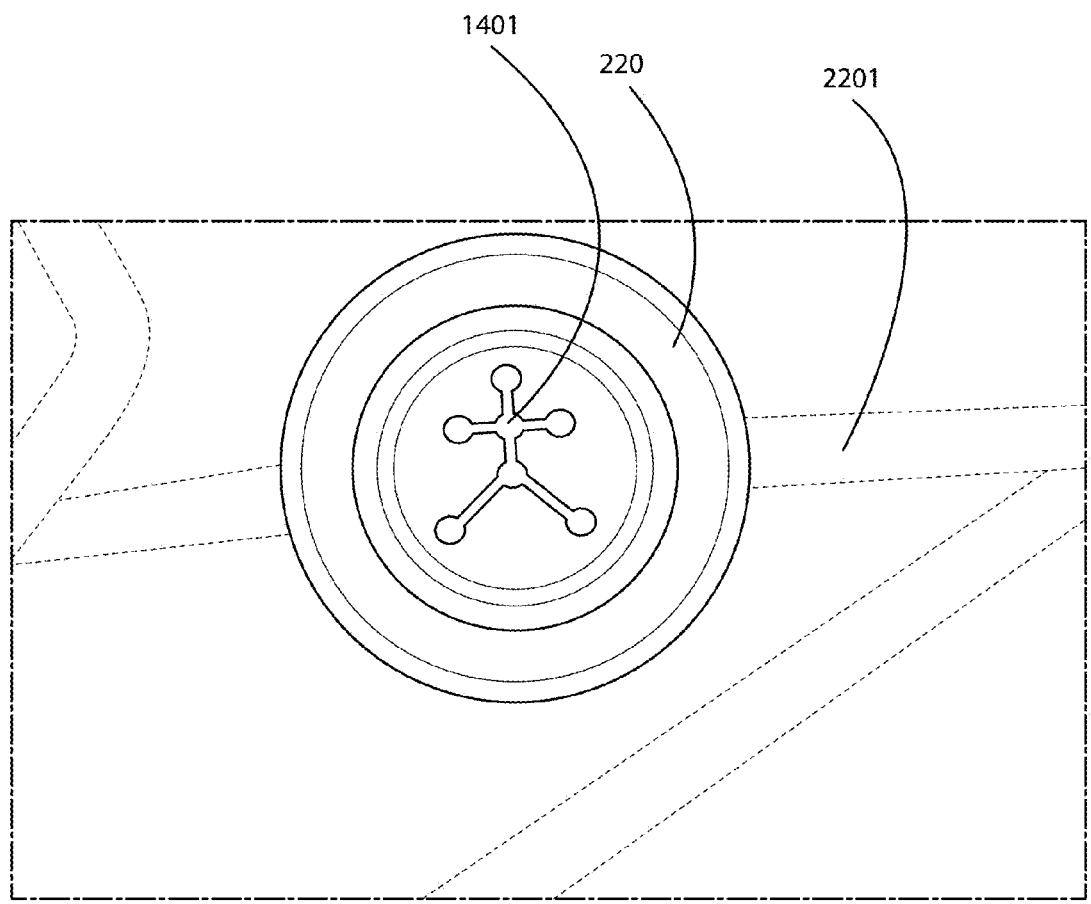
FIG. 23 illustrates a close-up of the embodiment shown in FIG. 22.

FIG. 23 illustrates a close-up of the embodiment shown in FIG. 22. Visual marker 1401 is shown on the outside portion of the helmet for use in capturing motion with an external camera for example.

Figure 24:
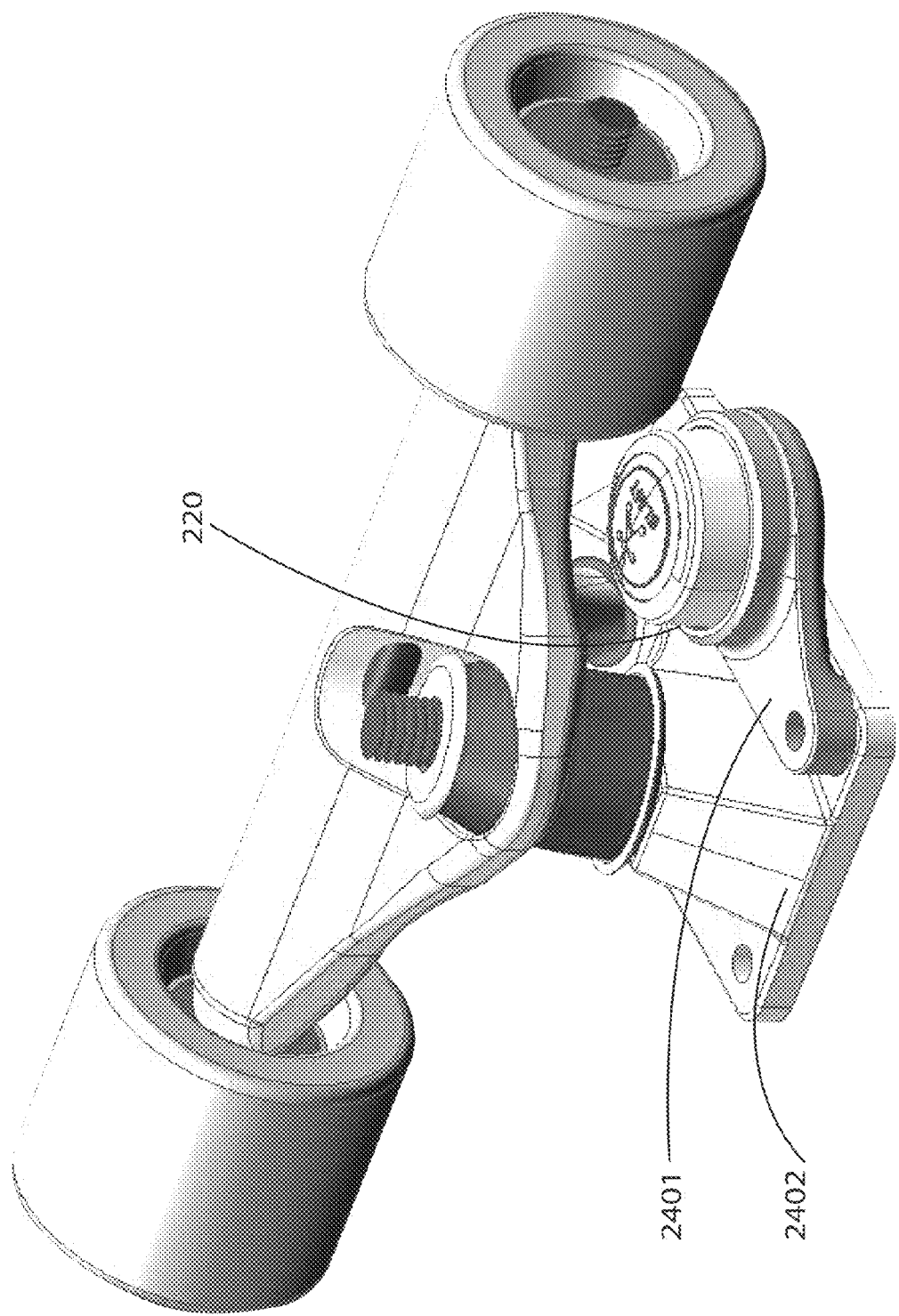
FIG. 24 illustrates a perspective view of an embodiment of the invention coupled with a skateboard truck.

FIG. 24 illustrates a perspective view of an embodiment of the invention coupled with a skateboard truck. As shown, enclosure 220 couples with or otherwise includes mount 2401 that is configured to couple with the existing screws of a skateboard truck mount 2402. Thus no extra holes are required for mounting an embodiment of the invention to a skateboard. The same configuration may be reshaped to fit holes associated with a snowboard binding or other planar oriented piece of equipment including skis as is shown in the next figure.

Figure 25:
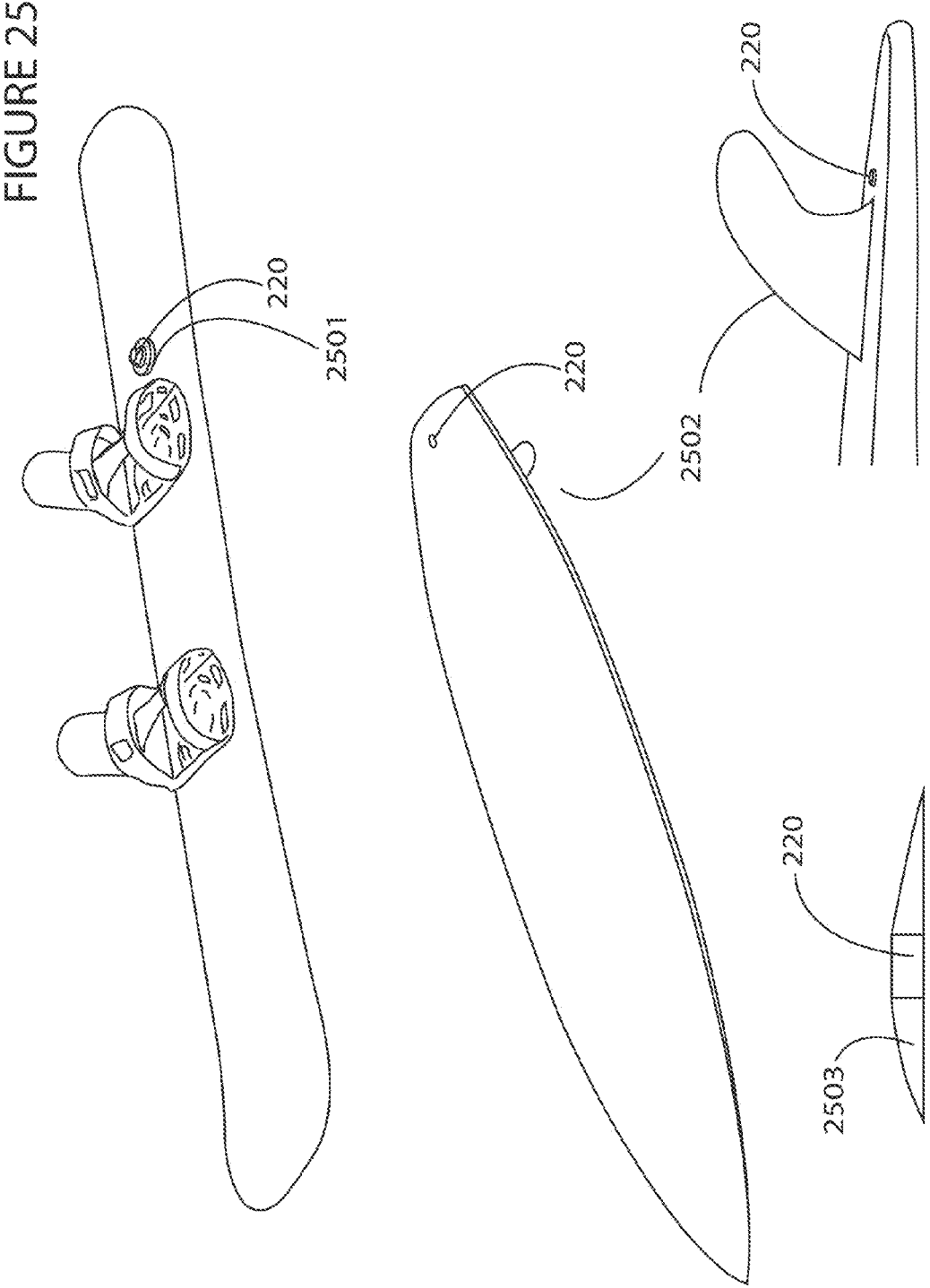
FIG. 25 illustrates an embodiment coupled with planar equipment.

FIG. 25 illustrates an embodiment coupled with planar equipment. As shown, enclosure 220 may be mounted along with the snowboard binding 2501 of a snowboard. In one or more embodiments, the enclosure may be coupled with the snowboard mount itself, or utilize a flat version of mount 2401 to couple with an existing screw used to mount the binding. As shown in the lower portion of the figure, enclosure 220 may mount on or near the top of the surfboard or on the underside of the surfboard near the skeg 2502 since surfboards may be made from materials that enable the transmission of electromagnetic waves. In one or more embodiments enclosure 220 may be housed in streamlined mount 2503 and adhesively mounted to any planar equipment, for example the snowboard, surfboard or skis. Streamlined mounts provide low wind or water drag and minimize interference with external objects for example.

Figure 26:
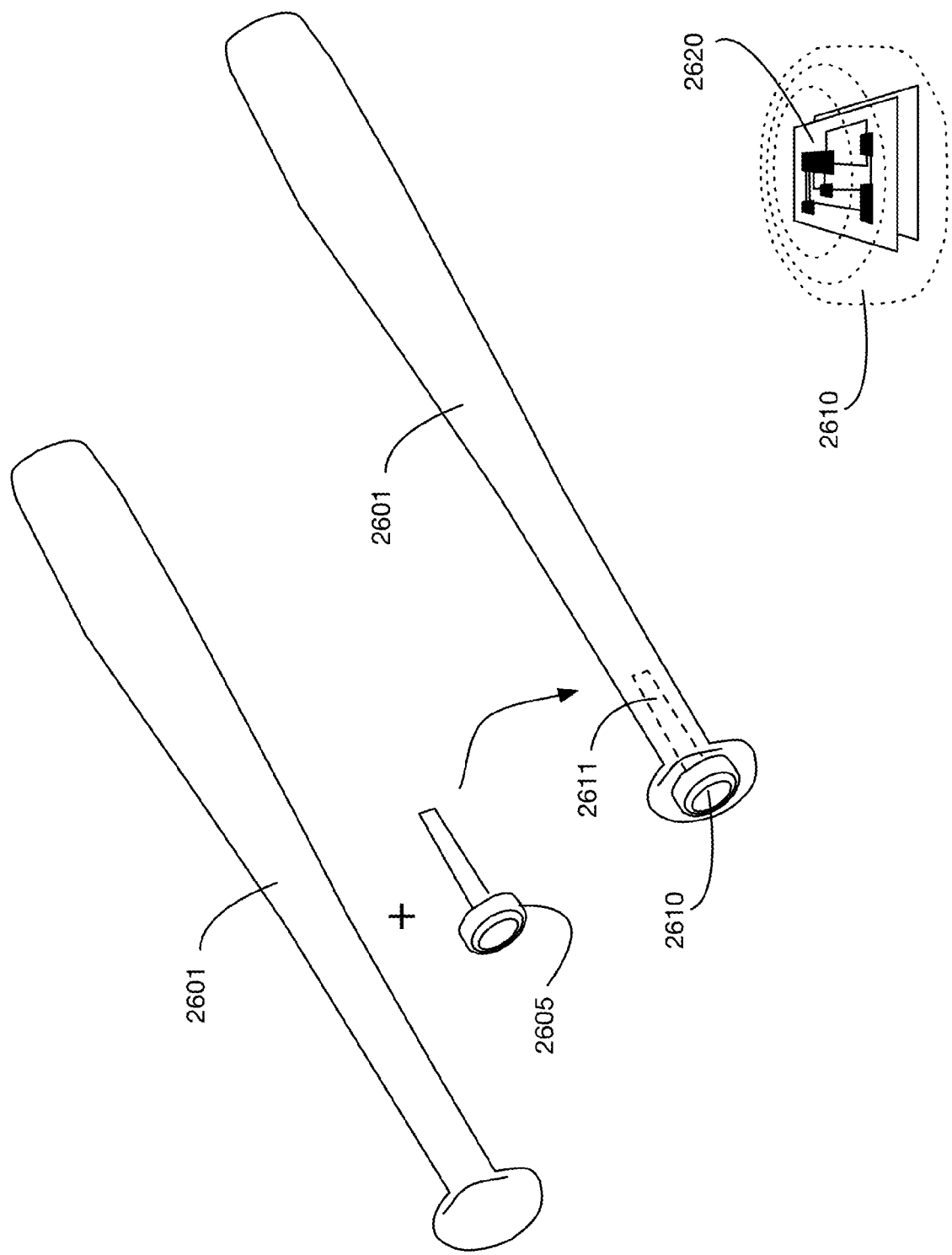
FIG. 26 illustrates an embodiment of the invention configured to couple with a baseball bat.

FIG. 26 illustrates an embodiment coupled with a baseball bat. Sensor mount and enclosure 2605 is installed on baseball bat 2601. The sensor and mount 2605 has an external portion or enclosure 2610 that protrudes from the knob of the bat, and an internal portion or mount 2611 that is coupled with the bat, for example inside the bat. The external portion or enclosure 2610 of the mount encloses electronics 2620, which may for example include circuit boards, a battery, integrated circuits, and an antenna.

Figure 27:
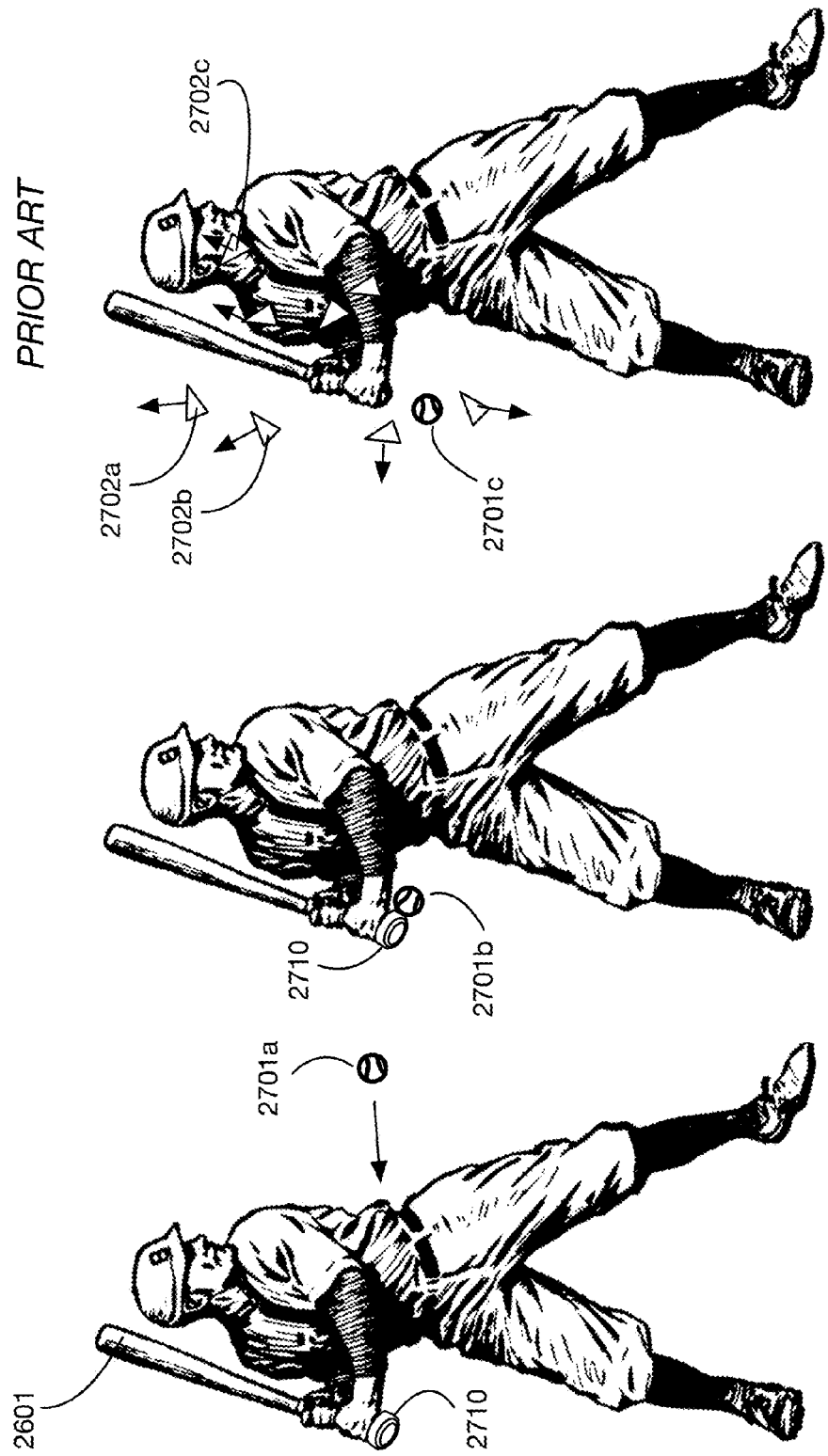
FIG. 27 illustrates prior art that is subject to shattering when the mount experiences an impact.

FIG. 27 illustrates a risk with the prior art when an enclosure experiences an impact event. In FIG. 27, enclosure 2710 is attached to bat 2601, as illustrated in FIG. 26. However, the mount 2710 is not designed to be shatter proof. Baseball 2701a approaches the bat and impacts the enclosure 2710 at location 2701b. The impact force shatters the enclosure 2710, and potentially the mount internal to the bat, and fragments such as 2702a, 2702b, and 2702c generally move away from the impact area rapidly. These fragments may pose a safety risk; for example, fragment 2702c may hit the eye of the batter.

Figure 28:
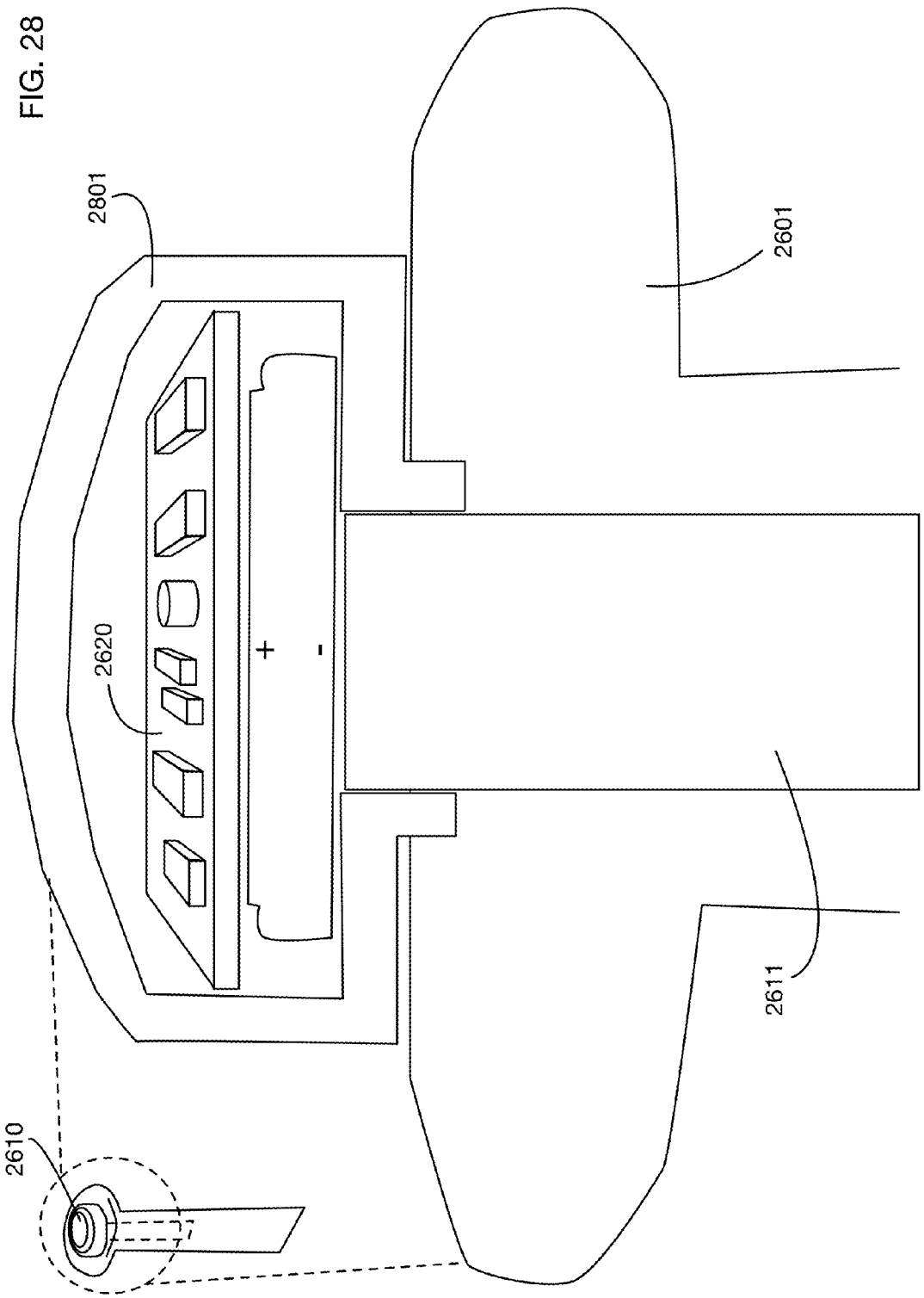
FIG. 28 illustrates an embodiment of a shatter proof mount, shown coupled to a baseball bat, that uses an enclosure comprising a shatter proof or shatter resistant material surrounding the sensor.

FIG. 28 illustrates an embodiment with a shatter proof enclosure and mount. As in FIG. 26, the mount is shown attached to baseball bat 2601. This example is for illustration; one or more embodiments may be attached to any type of equipment. The exposed enclosure 2610 is covered with a protective layer 2801. This layer may for example include materials that are designed to flex rather than break, or materials that are sufficiently strong that they will not shatter under impact. Materials in protective layer 2801 may include for example, without limitation, rubber, silicone rubber, plastics, thermoplastics, polycarbonates, acrylics, reinforced glass, metals, and carbon fiber reinforced polymers. One or more embodiments may use multiple protective layers. One or more embodiments may use protective layers of any size, thickness, and shape.

Figure 29:
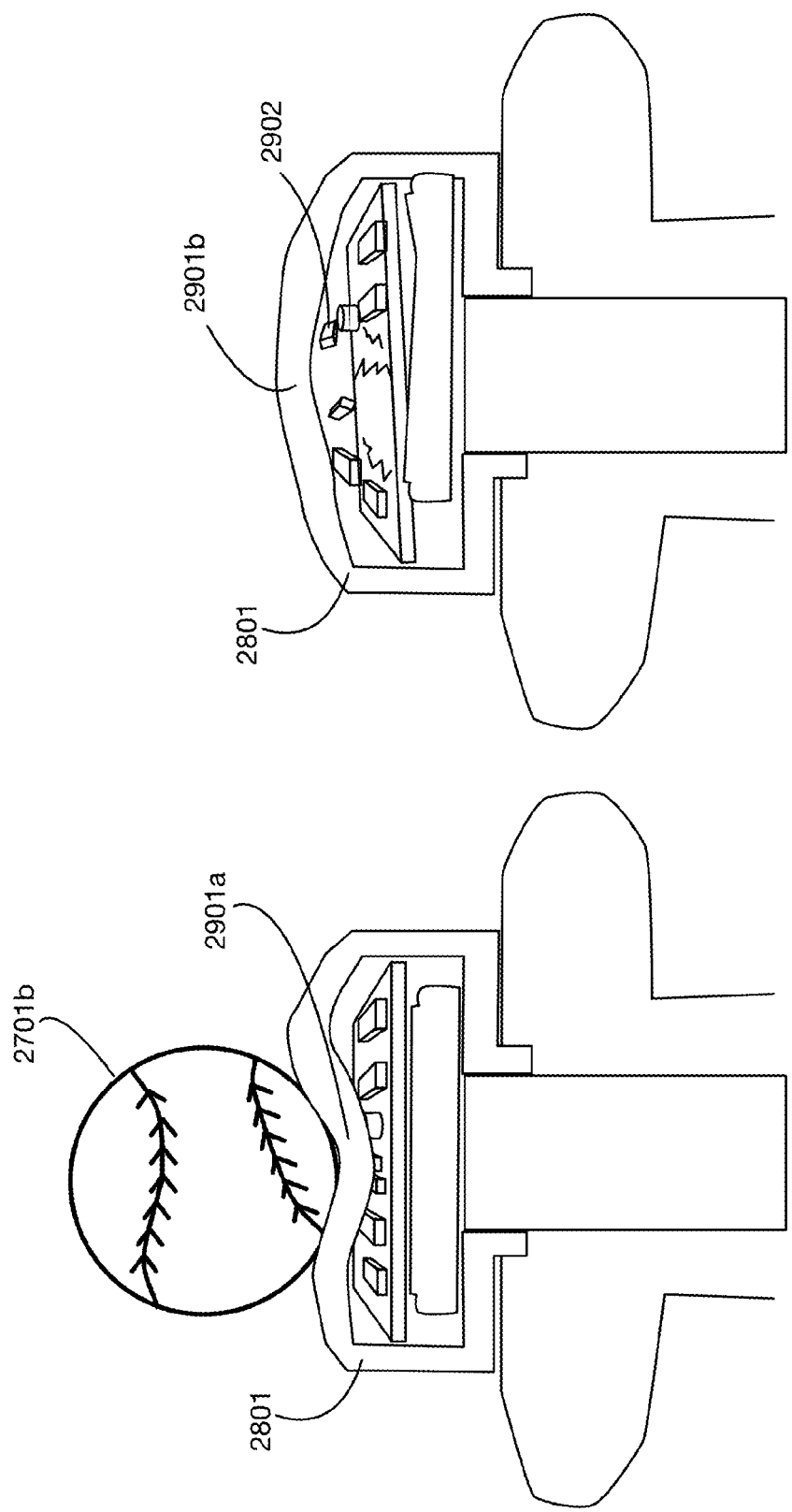
FIG. 29 illustrates how an embodiment shown in FIG. 28 handles an impact: the enclosure may for example flex instead of breaking, and it prevents components from exiting the enclosure.

FIG. 29 illustrates an impact event with the mount of FIG. 28. Baseball 2701b impacts the enclosure, and protective layer 2801 deforms at location 2901a; however, the protective layer does not break. After impact, the impacted location 2901b maintains integrity and prevents internal components such as 2902 from exiting the enclosure. Although the internal components may be damaged, the protective layer 2801 prevents components or fragments from exiting the enclosure, mitigating the potential safety risk.

Figure 30:
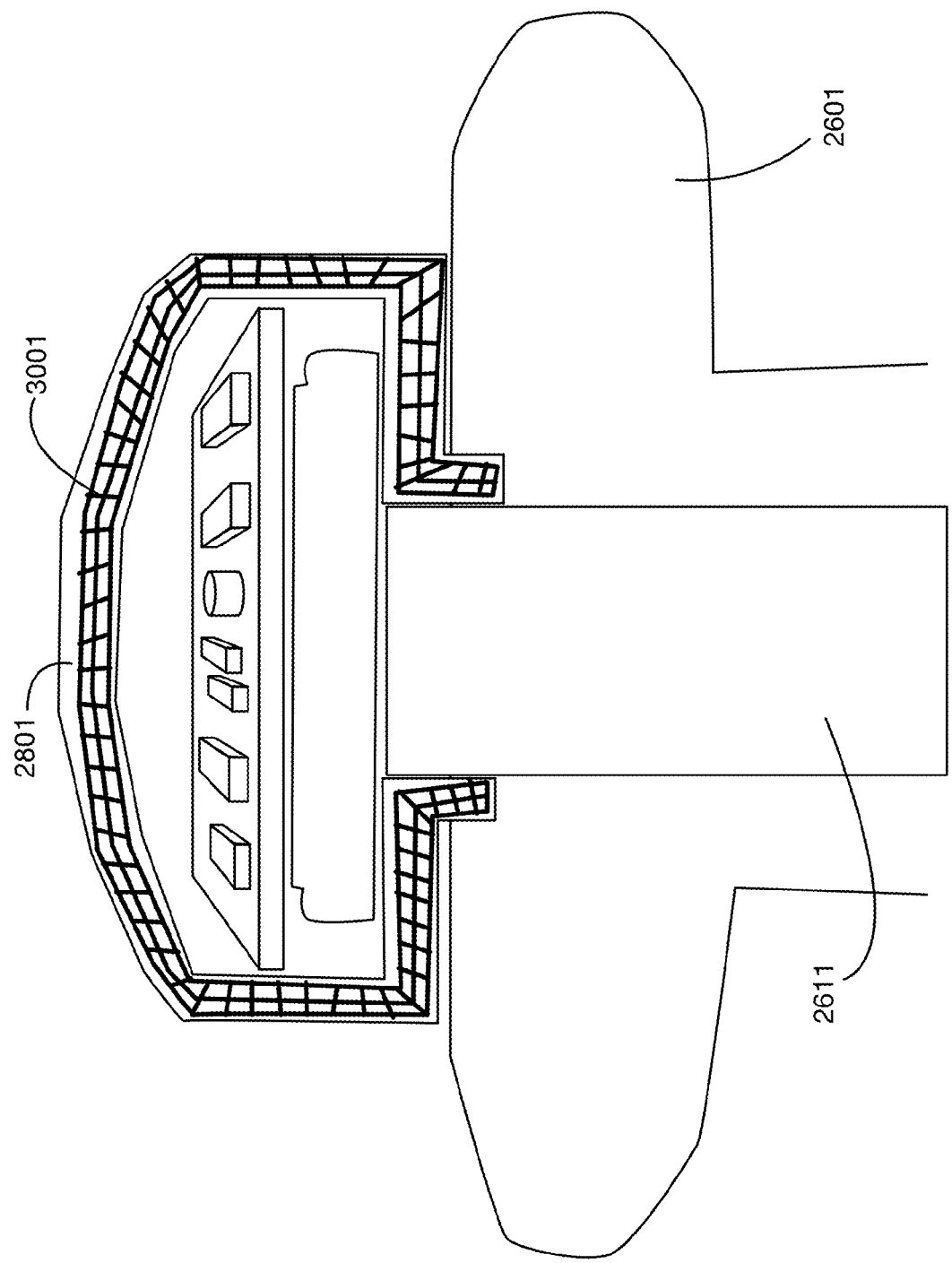
FIG. 30 illustrates an embodiment of a shatter proof mount with a mesh embedded into or surrounding the enclosure.

One or more embodiments may use a mesh structure or composite structure instead of or in addition to materials that flex or resist shattering. The mesh may be for example embedded into the protective layer or the enclosure. FIG. 30 illustrates an example with mesh 3001 integrated into protective layer 2801. The mesh may for example prevent components from exiting the enclosure even if the layer 2801 experiences tears or breaking.

Figure 31:
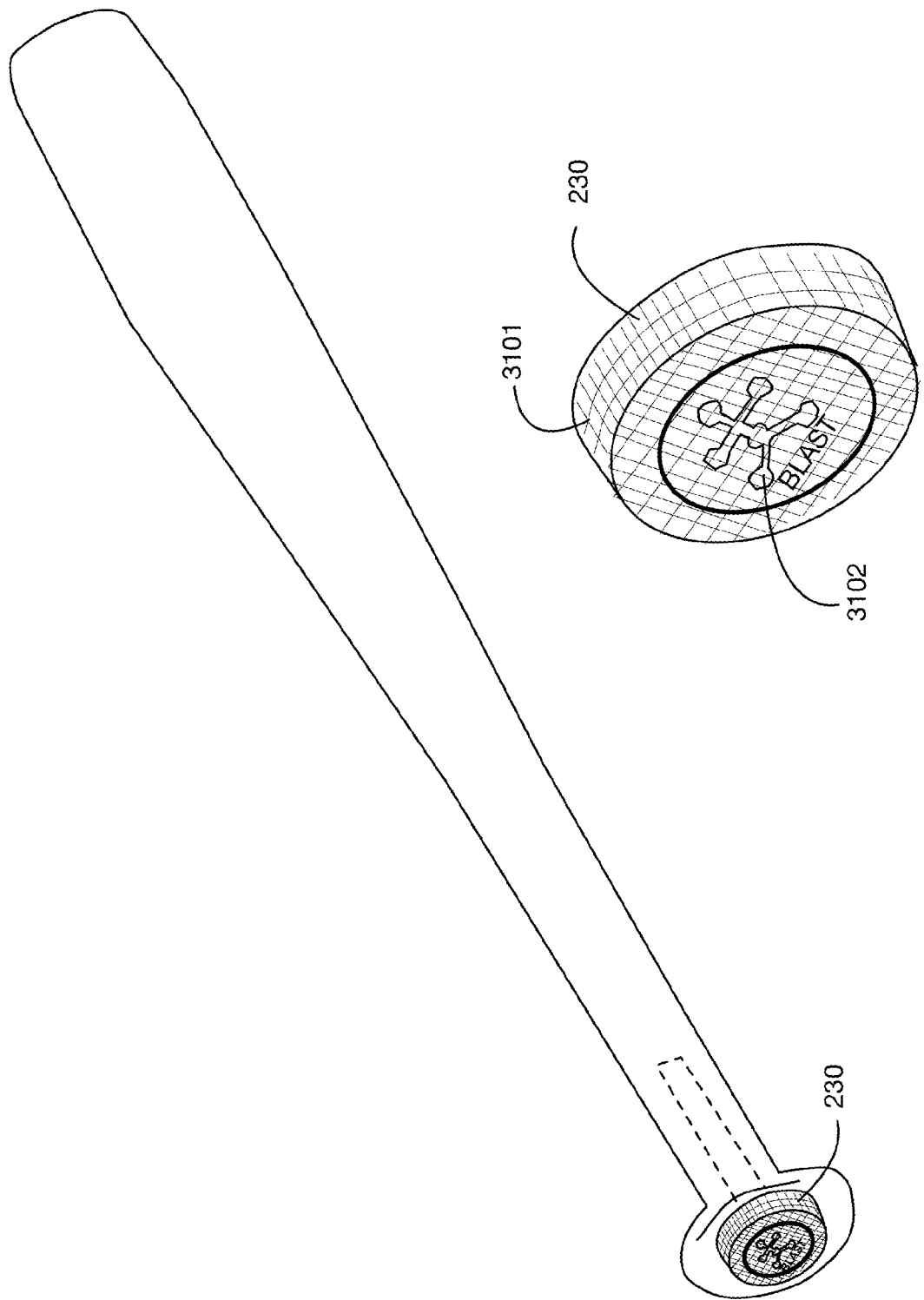
FIG. 31 illustrates an embodiment with a mesh embedded into a cap that has a visual marker.

FIG. 31 illustrates a mesh installed on the outside of an enclosure. Mount 230 has a mesh 3101 added to the external surface, which prevents fragments of the enclosure or internal components from exiting the mesh. The mount 230 has a visual marker 3102 which remains visible through the mesh.

Embodiments of the invention may be mounted on any type of equipment to prevent shattering for example. Thus any mount described herein for any type of equipment may couple with an enclosure that utilizes or includes materials or layers as described in FIGS. 28-31.

Figure 32:
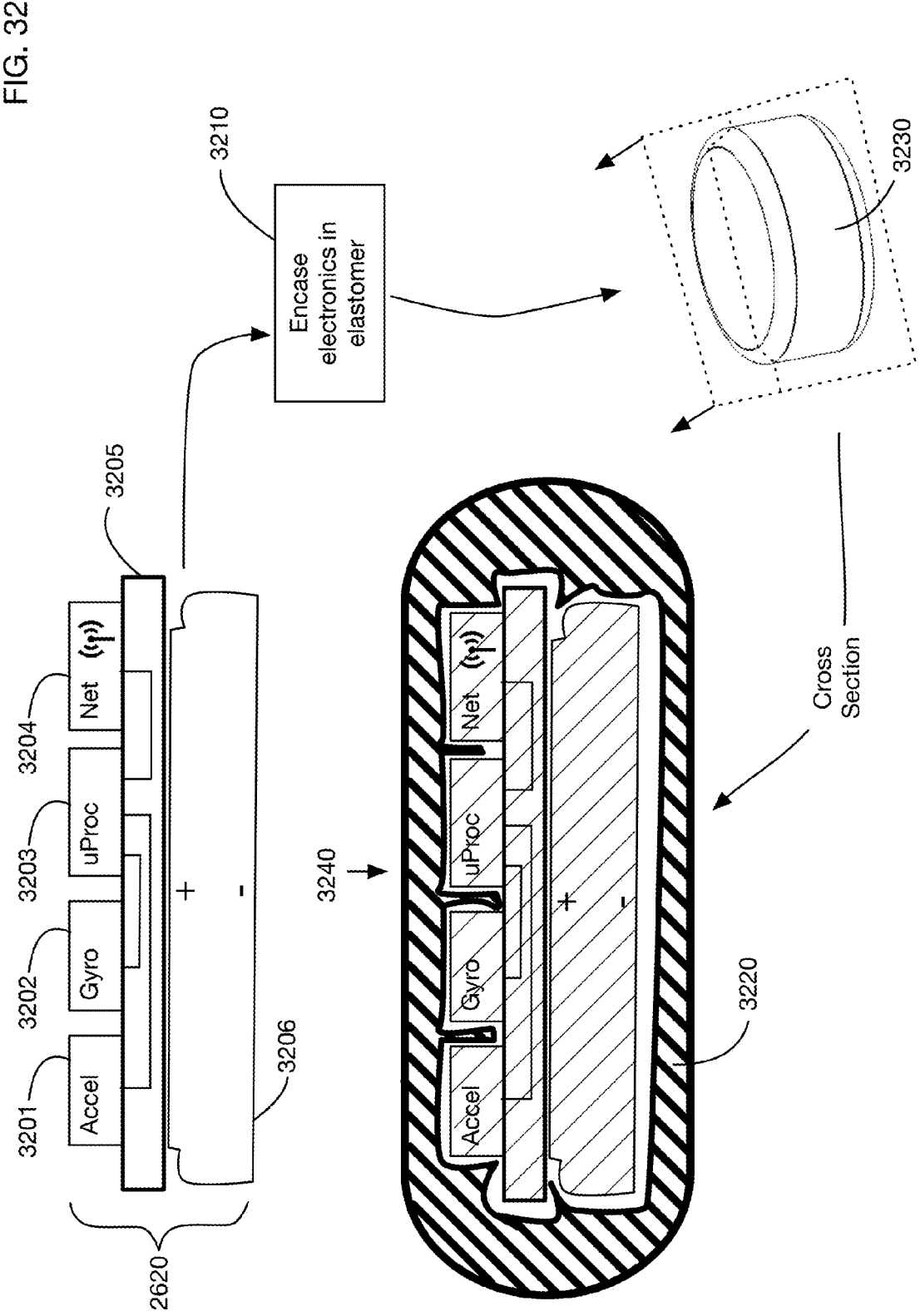
FIG. 32 illustrates an embodiment of an elastomer encased motion sensor package, with internal electronics encased in a layer of elastomer that surrounds and protects the electronics.

FIG. 32 illustrates an embodiment that encases motion sensor electronics in a layer of elastomer. Sensor electronics 2620 may include for example motion sensors such as accelerometer 3201 and gyroscope 3202. One or more embodiments may incorporate any type or types of motion sensors, including for example, without limitation, any sensor that measures one or more aspects of a position, orientation, linear velocity, angular velocity, linear acceleration, or angular acceleration. Electronics 2620 may also include one or more processors such as microprocessor 3203. Electronics 2620 may also include one or more network interfaces, such as network interface 3204; network interfaces may be wired or wireless, and may use any desired communications protocols. Wireless network interfaces may include one or more antennas. Electronics 2620 may also include one or more power sources, such as for example battery 3206. Electronic components may be mounted on or connected via one or more printed circuit boards, such as for example circuit board 3205.

The electronic components 2620 may be encased in an elastomer using any desired manufacturing process 3210. For example, an elastomeric casing may be molded or cast, or applied directly around electronics 2620. One or more embodiments may use any elastomeric material or materials, including for example, without limitation, silicone rubber, natural rubber, synthetic rubber, or polyurethane.

Encased sensor package 3230 may for example be surrounded on all sides with an elastomer layer, with all of the electronics 2620 fully encased by the elastomer. FIG. 32 shows a cross section view 3240 of the encased sensor package 3230. The elastomer layer 3220 is shaped to fully surround the enclosed electronic components. In one or more embodiments the elastomer layer may comprise multiple sections, which may for example be joined together using glues, press fits, snaps, or any other attachment mechanism.

Figure 33:
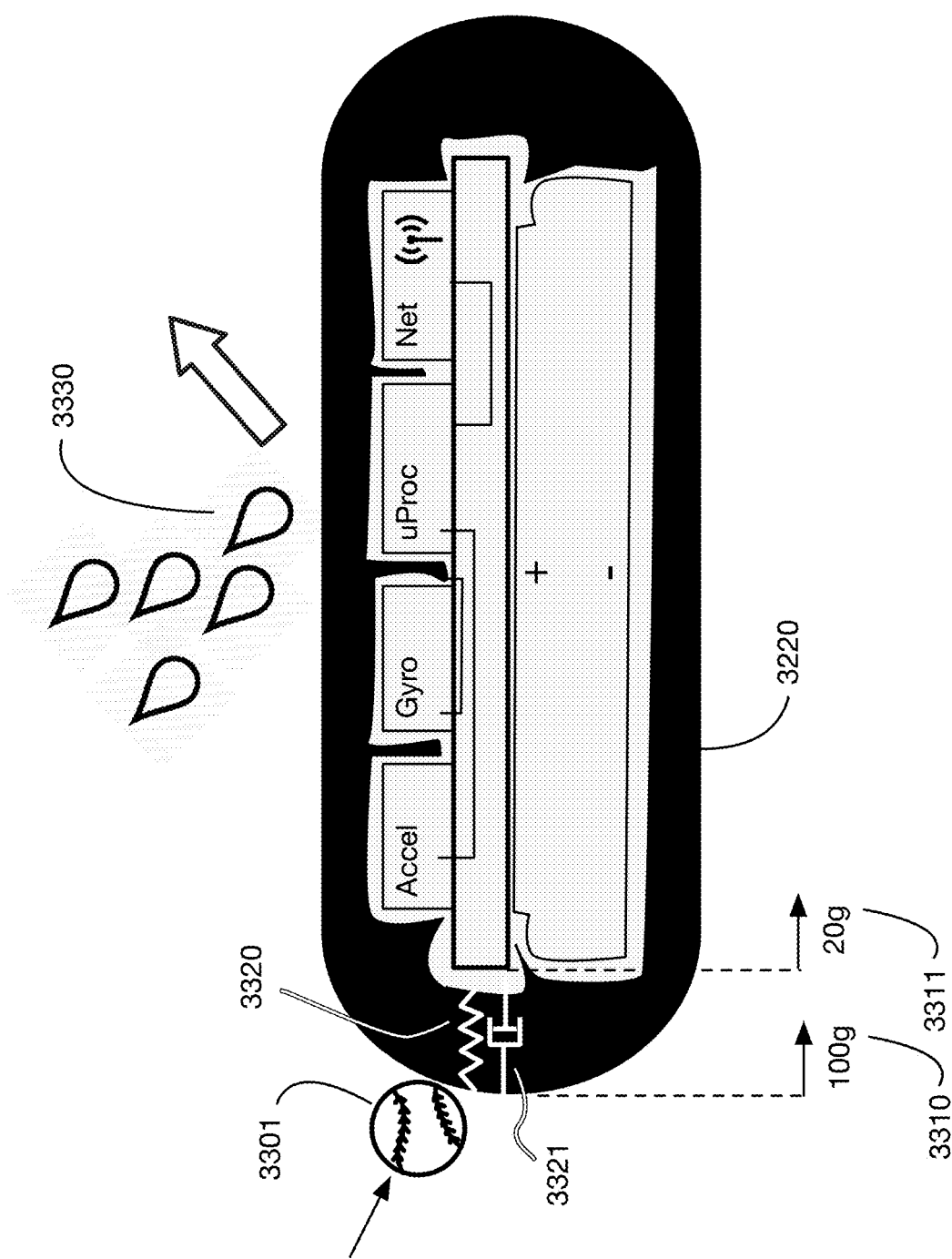
FIG. 33 illustrates two features of the elastomer encased package of FIG. 32: shock isolation and water resistance.

FIG. 33 illustrates two benefits of the elastomer encasing: shock isolation, and water resistance. Impact with an object such as ball 3301 can generate very large shock forces on the sensor package. For example, the outer edge of the elastomer layer 3220 may experience a very large acceleration such as 3310. However, the elastomer layer provides shock isolation to reduce the shock forces on the enclosed electronics. For example, the elastomer layer may be modeled as a spring-damper system equivalent to a spring 3320 and a viscous damper 3321. As is known in the art, a spring-damper system can substantially reduce the impact shock felt by the enclosed components; for example, the acceleration of the electronic components may be reduced to level 3311, far below the external acceleration 3310. One or more embodiments may select a desired level of shock isolation, and configure the shape, thickness, and materials of the elastomer layer 3220 accordingly to achieve this level of shock isolation. As illustrated in FIG. 33, the elastomer layer 3220 may also provide resistance to water 3330, by reflecting some or all of the water from the outer surface of the layer. One or more embodiments may provide additional water sealing layers to further enhance water resistance.

In one or more embodiments the elastomer encased sensor package may have a size and shape that matches a component of an item of sports equipment, allowing the sensor package to be installed into the sports equipment as a direct replacement for the component. FIG. 34 illustrates an example with the sensor package integrated into a skateboard riser. View A shows a skateboard truck with a riser, and view B is an exploded view. Skateboard truck 3401 has riser 3402 attached to the truck; the riser fits between the skateboard truck and the board. A riser may provide shock absorption in addition to raising the level of the board. One or more embodiments may integrate the sensor package and the elastomer layer directly into a skateboard riser. As shown in FIG. 34, the elastomer encased package 3430 may be placed directly into riser 3402. In one or more embodiments the entire riser may function as the elastomer layer, and the electronics may be encased in the riser.

Figure 35:
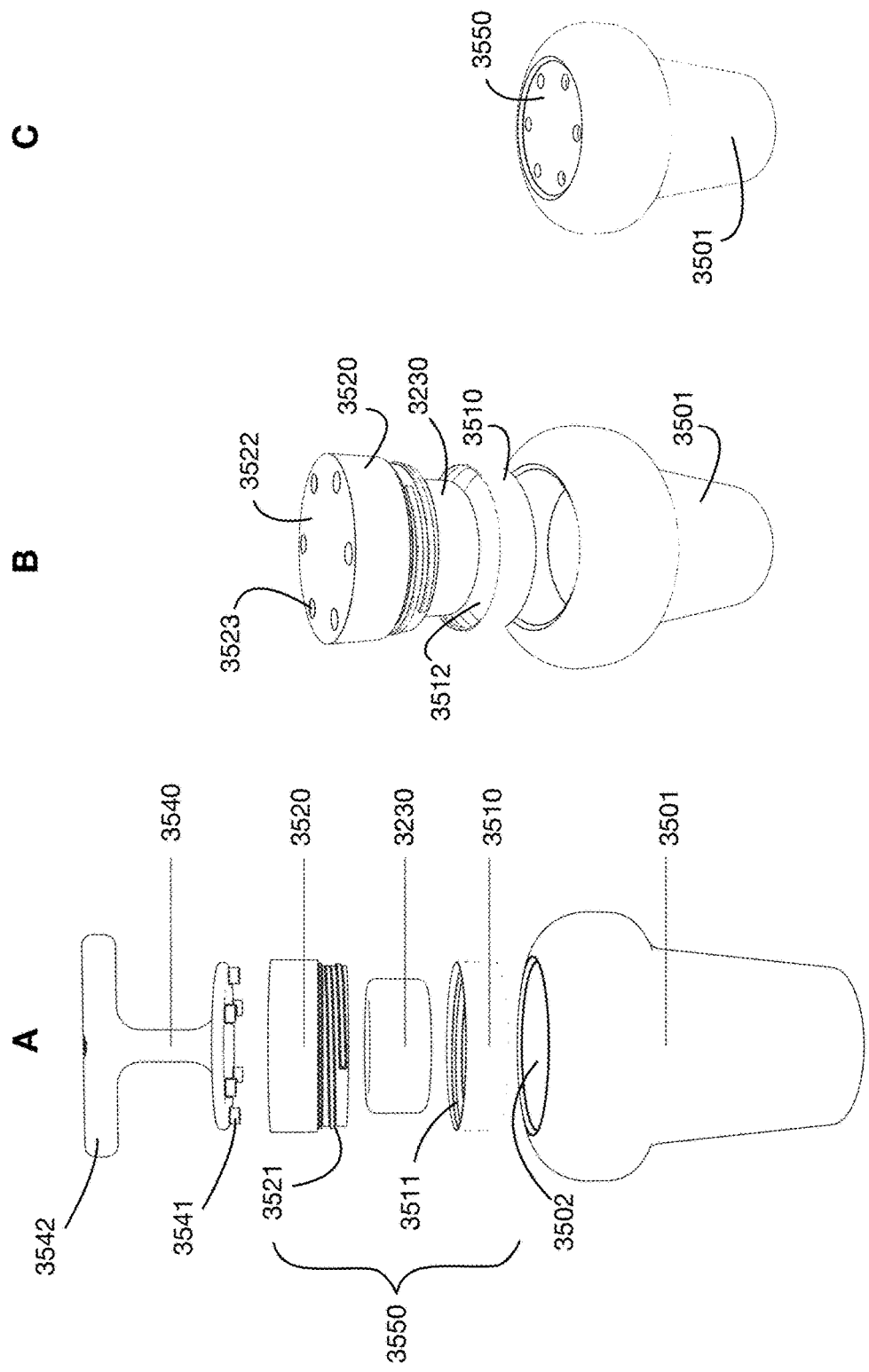
FIG. 35 illustrates an embodiment that includes an elastomer encased motion sensor package installed into an outer housing that has a threaded receiver portion and a threaded lid portion; in the example shown, the sensor package and the outer housing are installed into a cavity in the knob of a baseball bat.

In one or more embodiments the elastomer encased sensor package may be placed inside an outer housing. FIG. 35 illustrates an embodiment that includes an outer housing. Views A and B are exploded views. Elastomer encased sensor package 3230 is placed inside an outer housing comprising a receiver portion 3510 and a lid portion 3520. The receiver and lid portions of the outer housing may be of any desired size and shape, and may be made of any desired material. In one or more embodiments the outer housing may also provide additional shock isolation or water resistance. The outer housing may also be made of an elastomer, or it may be formed from hard plastic, metal, or any other material. In the embodiment illustrated in FIG. 35, the receiver 3510 and lid 3520 are cylindrical in shape. The receiver 3510 has a closed lower surface 3512 and an open top surface; the lid 3520 has a closed top surface 3522 and an open lower surface. In this embodiment the receiver and lid are threaded so that they screw together to close the outer housing. Receiver 3510 has threads 3511 on its inner surface, and lid 3520 has matching threads 3521 on its outer surface. Use of threads to attach the components of the outer housing is illustrative; one or more embodiments may use any attachment mechanism or material to join the receiver and the lid to close or seal the outer housing.

In one or more embodiments the outer housing may be configured to fit into a cavity or other location in an item of sports equipment. In the embodiment shown in FIG. 35, the outer housing 3550 containing the elastomer encased electronics 3230 is shaped and sized to fit into a hole 3502 in the knob 3501 of a baseball bat. View C shows the complete package 3550 (which includes components 3230, 3510, and 3520) installed into knob 3501 of the bat.

One or more embodiments may include a tool or tools that may be used to open or close the outer housing. For example, FIG. 35 illustrates tool 3540. In this embodiment the tool is rotated to screw the lid 3520 onto or off of the receiver 3510. Handles 3542 provide leverage for the turning force. This illustrative tool has protrusions 3541 that fit into holes 3523 on the surface 3522 of lid 3520. Any tool that assists a user in opening or closing the outer housing is in keeping with the spirit of the invention.

Figure 36:
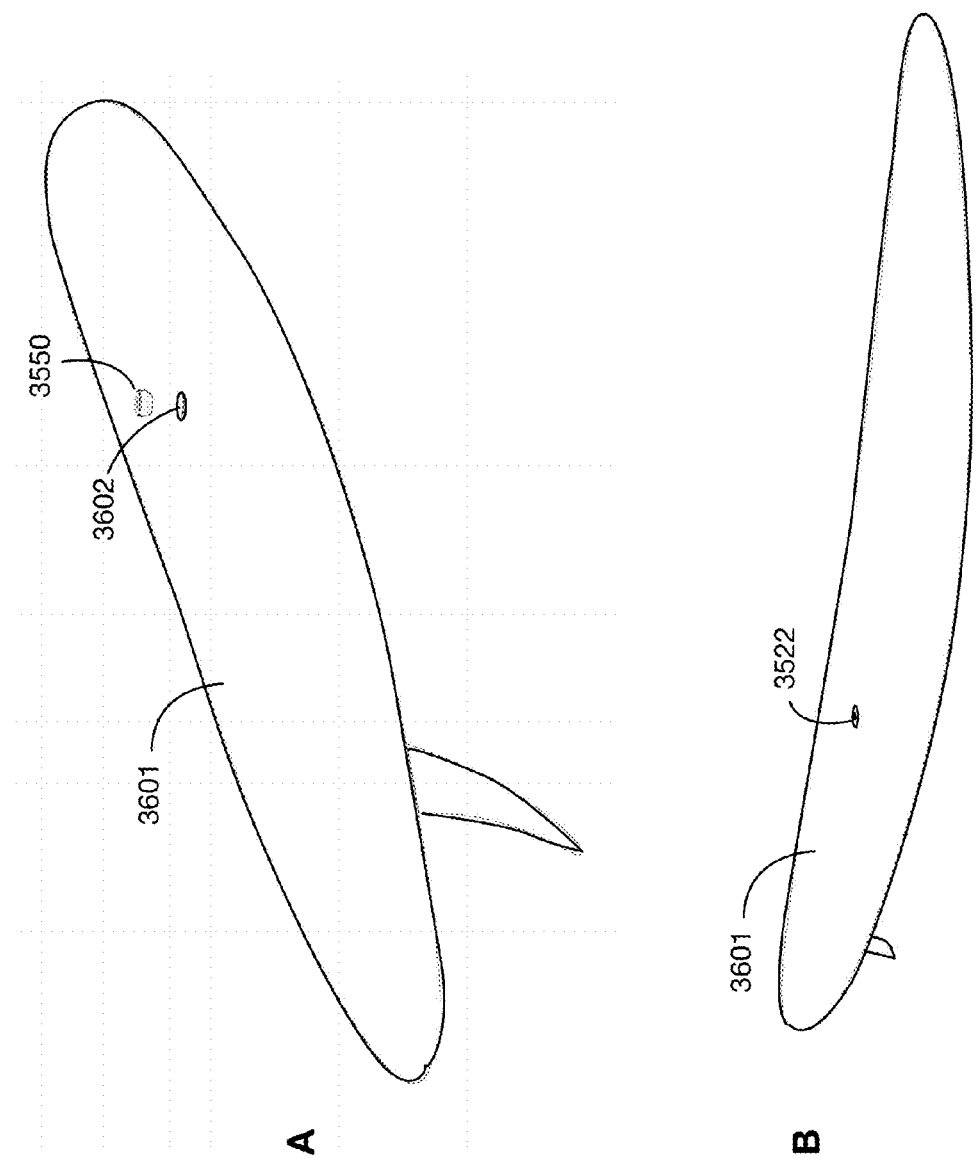
FIG. 36 illustrates an elastomer encased motion sensor package installed into a cavity in a surfboard.

FIG. 35 illustrates a sensor package configured to fit into a cavity in a baseball bat. FIG. 36 illustrates a sensor package configured to fit into a cavity in a surfboard. In view A, surfboard 3601 has cavity 3602 installed into its top surface. Sensor package 3550 is configured to fit into this cavity 3602. In view B, the sensor package 3550 is fully installed into surfboard 3601, and the top surface 3522 of the lid is approximately flush with the upper surface of the surfboard.

Figure 37:
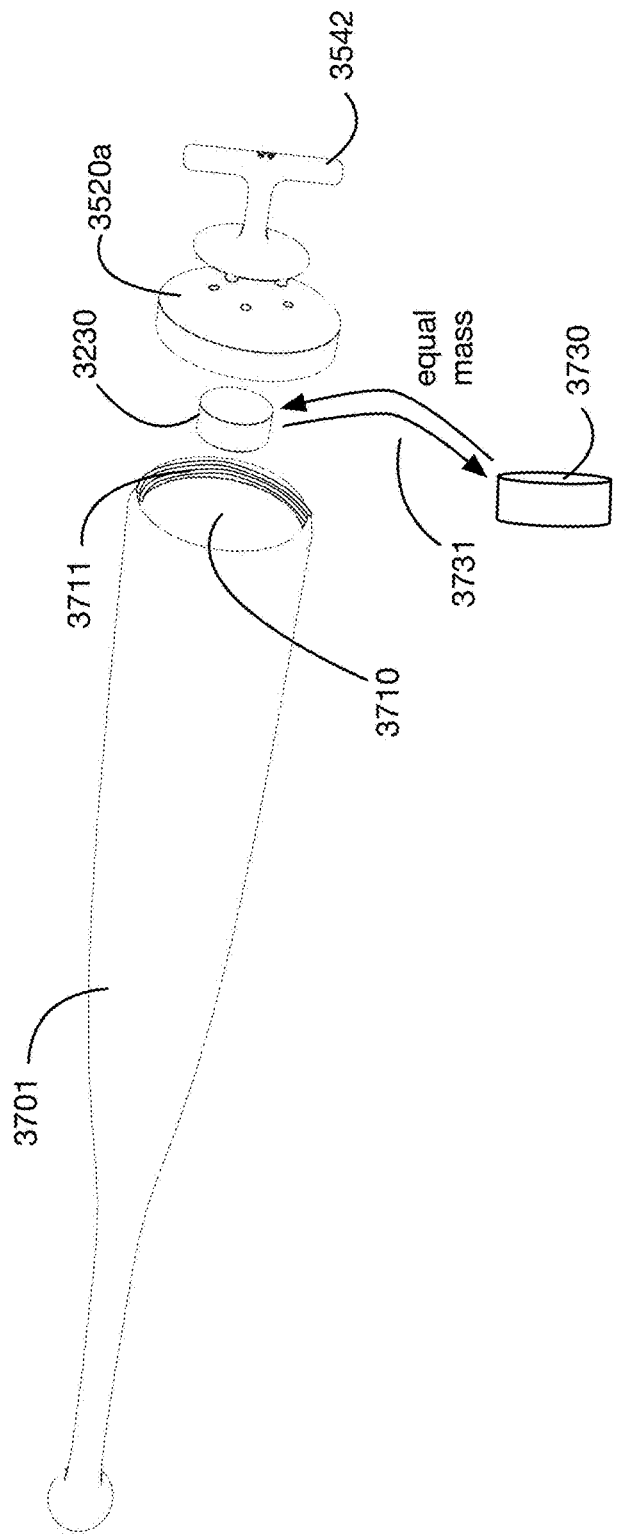
FIG. 37 illustrates an embodiment that integrates the receiver of the outer housing into the tip of a baseball bat. This embodiment also includes a dummy weight that can be installed in the bat as a replacement for the sensor package.

In one or more embodiments the receiver, the lid, or both, may be integrated into an item of sports equipment. FIG. 37 illustrates an example with the receiver integrated into a cavity in the tip of baseball bat 3701. The bat tip has cavity 3710 with threads 3711 along the edges. These features may for example be machined into the bat itself. Elastomer encased sensor package 3230 fits into cavity 3710. Lid 3520a fits onto the top of the bat; it has threads (not shown) that match the threads 3711. Tool 3542 may be used to open and close the lid 3520a. In this embodiment the elastomer encased sensor package 3230 may be replaced 3731 with dummy weight 3730, if it is desired to remove the sensor for certain applications (such as for example for official games). The dummy weight 3730 may have approximately equal mass as the elastomer encased sensor package 3230, so that the bat feels the same with either the sensor installed or the dummy weight installed.

FIG. 38 illustrates an embodiment that includes a golf club grip adapter that may be used for mounting a sensor package onto the grip of a golf club. The adapter may for example be configured to fit into any size golf club grip. In the embodiment shown in view A, the adapter has a cylindrical tube 3810 with a spike 3811; the spike is designed to push through the top 3802 of the grip 3801 of a golf club. At the top end of the tube 3810 is flange 3812 that rests on the top of the grip 3802 when the adapter is fully installed. View B shows the adapter installed into the grip; only the top of the flange 3812 is visible. Outer housing 3550 includes a protrusion 3820 on the receiver portion 3510 that fits into the tube 3810 of the adapter. An illustrative procedure for installing a motion sensor package onto a golf club may for example include (1) inserting the spike 3811 of the grip adapter into the top 3802 of the grip; (2) securing the adapter until only the flange 3812 is visible; (3) attaching the receiver 3510 to the adapter; (4) placing the elastomer enclosed sensor package 3230 into the receiver 3510; (5) attaching lid 3520 to receiver 3510 to close the outer housing.

While the ideas herein disclosed has been described by means of specific embodiments and applications thereof, numerous modifications and variations could be made thereto by those skilled in the art without departing from the scope of the invention set forth in the claims.

What is claimed is:

1. An elastomer encased motion sensor package comprising:
   an enclosure, wherein said enclosure
      is shatter proof, and
      is at least partially exposed and at least partially protrudes from an outside portion of an outer surface of an item of sports equipment and comprises
      electronic components comprising
         one or more motion sensors, wherein each of said one or more motion sensors are configured to measure one or more of a position, an orientation, a linear velocity, an angular velocity, a linear acceleration, and an angular acceleration;
         a processor coupled to said one or more motion sensors;
         a wireless antenna coupled to said processor; and,
         a battery coupled to said processor;
   a layer of elastomer surrounding said enclosure and encasing said electronic components, wherein said layer of elastomer is configured to
      provide shock isolation for said electronic components;
      provide a water resistant barrier around said electronic components;
      flex instead of break; and,
      prevent shattered components of said enclosure from exiting said enclosure under impact; and,
   an outer housing that at least partially surrounds said layer of elastomer and said enclosure with said electronic components,
      wherein said outer housing is an elastomer;
      wherein said outer housing comprises
         a receiver portion having a cavity into which said layer of elastomer and said electronic components are placed; and, a lid portion configured to be detachably coupled to said receiver portion, thereby closing said outer housing;

wherein said outer housing surrounds an outer surface of said elastomer layer when said outer housing is closed; and, wherein said outer housing provides additional shock isolation and water resistance; and, wherein said elastomer encased motion sensor package comprising said enclosure with said electronic components, said layer of elastomer encasing said electronic components and said outer housing that at least partially surrounds said layer of elastomer and said electronic components is configured to be attached on an outside portion of said item of sports equipment.

2. The system of claim 1, wherein said layer of elastomer comprises one or more of silicone, natural rubber, synthetic rubber, and polyurethane.

3. The system of claim 1, wherein
said elastomer encased motion sensor package further comprises a size and shape that matches a component of said item of sports equipment; and,
said component of said item of sports equipment is configured to be replaced by said elastomer encased motion sensor package without limiting the functionality of said item of sports equipment.

4. The system of claim 3, wherein said component of said item of sports equipment is a riser pad of a skateboard.

5. The system of claim 1, wherein
said receiver portion is shaped substantially as a right circular cylinder with a closed bottom end and an open top end, comprising receiver threads along a portion of its inner circular surface or its outer circular surface;
said lid portion is shaped substantially as a right circular cylinder with an open bottom end and a closed top end, comprising lid threads along a portion of its inner circular surface or its outer circular surface; and,
said lid threads mate with said receiver threads to close said outer housing.

6. The system of claim 5, further comprising
an installation and removal tool configured to be detachably coupled to said lid portion, wherein a user turns said installation and removal tool to screw said lid portion onto or off of said receiver portion.

7. The system of claim 1, wherein said receiver portion is configured to be installed into a hole that exists in or that is configured to be created in said item of sports equipment.

8. The system of claim 7, wherein
said item of sports equipment is a surfboard;
said hole is a cavity in said surfboard; and,
said lid portion is substantially flush with an upper surface of said surfboard when said outer housing is closed.

9. The system of claim 7, wherein
said item of sports equipment is a baseball bat; and,
said hole is a cavity in the knob of said baseball bat.

10. The system of claim 1, further comprising
a dummy weight having a mass substantially equal to a mass of said layer of elastomer and said electronic components;
wherein
said dummy weight is configured to be detachably placed into said receiver portion instead of said layer of elastomer and said electronic components; and,
said lid portion is configured to be detachably coupled to said receiver portion when said dummy weight is placed in said receiver portion, thereby closing said outer housing.

11. The system of claim 1, further comprising
a golf club grip adapter comprising
a tube configured to be inserted through a top surface of a grip of a golf club, having a threaded inner surface; and,
a flange coupled to a top edge of said tube, and configured to rest on said top surface of said grip of said golf club when said tube is inserted through said top surface of said grip of said golf club; and,
a threaded protrusion coupled to said receiver portion and configured to mate with said threaded inner surface to detachably couple said receiver portion to said golf club grip adapter.

* * * * *